(12) United States Patent
Johansen et al.

(10) Patent No.: US 9,884,094 B2
(45) Date of Patent: Feb. 6, 2018

(54) METHOD OF TREATING DIABETES MELLITUS

(71) Applicant: Novo Nordisk A/S, Bagsvaerd (DK)

(72) Inventors: Thue Johansen, Koebenhavn (DK); Henriette Mersebach, Hellerup (DK); Mads Axelsen, Virum (DK); Martin Lange, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/398,018

(22) PCT Filed: May 1, 2013

(86) PCT No.: PCT/EP2013/059073
§ 371 (c)(1),
(2) Date: Oct. 30, 2014

(87) PCT Pub. No.: WO2013/164375
PCT Pub. Date: Nov. 7, 2013

(65) Prior Publication Data
US 2015/0126439 A1 May 7, 2015

Related U.S. Application Data

(60) Provisional application No. 61/641,540, filed on May 2, 2012, provisional application No. 61/641,544, filed on May 2, 2012.

(30) Foreign Application Priority Data

May 1, 2012 (EP) ..................................... 12166251
May 1, 2012 (EP) ..................................... 12166252

(51) Int. Cl.
*A61K 38/28* (2006.01)

(52) U.S. Cl.
CPC ..................................... *A61K 38/28* (2013.01)

(58) Field of Classification Search
CPC ..................................................... A61K 38/28
See application file for complete search history.

(56) References Cited

FOREIGN PATENT DOCUMENTS

| EP | 925792 A2 | 6/1999 |
|---|---|---|
| EP | 2264066 A2 | 12/2010 |
| WO | 95/07931 A1 | 3/1995 |
| WO | 2005/012347 A2 | 2/2005 |
| WO | 2010/049488 A1 | 5/2010 |
| WO | 2012055967 A2 | 5/2012 |

OTHER PUBLICATIONS

Anthony H. Barnett, A review of basal insulins, "Diabetic Medicine" Year 2003, vol. 20, No. 11, pp. 873-885.
Cuddihy R et al. Once-daily use of a new generation ultra-long acting basal insulin with a bolus boost in insulin-naive people with type 2 diabetes: comparison with insulin glargine, "46th Annual Meeting of the European Association for the Study of Diabetes (EASD)" Year 2010, vol. 53, pp. 975.
Garber A J et al. Attainment of glycaemic goals in type 2 diabetes with once-,twice-, or thrice-daily dosing with biphas insulin aspart 70/30(The 1-2-3 study) "Diabetes, Obesity and Metabolism" Year 2006, vol. 8, No. 1, pp. 58-66.
Heise T et al. A New-Generation Ultra-Long-Acting Basal Insulin With a Bolus Boost Compared With Insulin Glargine in Insulin-Naïve People With Type 2 Diabetes, "Diabetes Care" Year 2011, vol. 34, No. 3, pp. 669-674.
Inzucchi S E et al. ManagementofHyperglycemiainType2 Diabetes: A Patient-Centered Approach, "Diabetes Care" Year 2012, vol. 35, pp. 1364-1379.
Krzysztof Strojek et al. Once-daily initiation with biphasic insulin aspart 30 versus insulin glargine in patients with type 2diabetes inadequately controlled with oral drugs: an open-label, multinational RCT, "Current Medical Research & Opinion" Year 2009, vol. 25, No. 12, pp. 2887-2894.
Niskanen L et al. Comparison of a soluble co-formulation of insulin degludec/insulin aspart vs biphasic insulin aspart 30 in type 2 diabetes: a randomised trial, "European Journal of Endocrinology" Year 2012, vol. 167, No. 2, pp. 287-294.
T. Heise et al. Towards peakless, reproducible and long-acting insulins. An assessment of the basal analogues based on isoglycaemic clamp studies, "Diabetes, Obesity and Metabolism" Year 2007, vol. 9, No. 5, pp. 648-659.
IDF Clinical Guidelines Task Force, Guideline for Management of Postmeal Glucose. "International Diabetes Federation" Year 2007.
Ma Z et al. IDegAsp: a novel soluble insulin analogs combination, "Expert Opin. Biol. Ther" Year 2012, vol. 12, No. 11, pp. 1533-1540.
"Insulin Degludecplus Provides a Better Glycaemic Control Compared to Insulin Glargine," International Endocrinological Journal, 7 (39), of Nov. 30, 2011, Web-based media, found in the Internet: http://www.mif-ua.com/archive/article/22989.

*Primary Examiner* — Gyan Chandra
(74) *Attorney, Agent, or Firm* — Rosemarie R. Wilk-Orescan

(57) ABSTRACT

A combination comprising at least a first insulin-like compound and a second insulin-like compound for treating a condition or a disease in a subject in need thereof where administration of insulin would be of benefit to said subject is described. The combination is administered in an amount to achieve a beneficial glycaemic control in said subject as determined by the levels of $HbA_{1c}$ in said subject after administration of said combination at the largest meal of the day for said subject; wherein said beneficial glycaemic control by said combination is superior to any glycaemic control achieved by an equivalent dose of IGlar in said subject as determined by the levels of $HbA_{1c}$ in said subject after administration of IGlar for said subject and/or wherein said beneficial glycaemic control by said combination comprises decreasing the levels of $HbA_{1c}$ in said subject to about 7 or less after administration of said combination at the largest meal of the day; wherein said first insulin-like compound is longer acting than the second insulin-like compound; wherein said combination is administered at the largest meal of the day for said subject; wherein said first insulin-like compound is at least a long acting insulin, preferably an ultra long acting insulin; wherein said first insulin-like compound is a derivative of a naturally occurring insulin or is an insulin analog; and wherein said first insulin-like compound has a side chain attached to the a-amino group of the N-terminal amino acid residue of the B chain or to the ε-amino group of a Lys residue present in the B chain of the parent insulin, the side chain being of the general formula (I): —W—X—Y—Z.

5 Claims, 1 Drawing Sheet

METHOD OF TREATING DIABETES MELLITUS

CROSS-REFERENCE TO RELATED APPLICATIONS

This application is a 35 U.S.C. §371 National Stage application of International Application PCT/EP2013/059073 (WO2013/164375), filed May 1, 2013, which claimed priority of European Patent Application 12166252.2, filed May 1, 2012 and European Patent Application 12166251.4, filed May 1, 2012; this application claims priority under 35 U.S.C. §119 of U.S. Provisional Application 61/641,540; filed May 2, 2012 and U.S. Provisional Application 61/641,544, filed May 2, 2012; all of which are incorporated by reference.

FIELD OF THE INVENTION

The present invention relates to a pharmaceutical composition and a novel administration scheme.

The present invention is useful in treatment of conditions like diabetes mellitus and hyperglycaemia, in particular of insulin-dependent diabetes mellitus.

BACKGROUND OF THE INVENTION

Diabetes mellitus often requires insulin treatment to establish proper metabolic control (comprising mainly glycaemic control, but also other metabolic parameters benefit from insulin treatment). The established practice of insulin treatment is to administer the insulin product once or more often per day, optionally in combination with other treatment modalities, as described in available treatment guidelines. Intravenous and subcutaneous insulin infusion is also used in clinical practice.

One widely used insulin treatment option is to administer a long acting insulin product, also referred to as basal insulin, to cover the insulin need of the patient wholly or partially. The long acting insulin is administered once or more often per day, at the same time every day, and is used on both type 1 diabetes and type 2 diabetes as well as for other forms of insulin requiring disease states (hyperglycaemia of any cause).

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin, given at the same time every day, to cover the basal insulin requirement supplemented by bolus injections of a rapid acting insulin to cover the insulin requirement related to meals.

The current practice in management of diabetes and hyperglycaemia is set forth in for example:

IDF Clinical Guidelines Task Force. Guideline for Management of PostMeal Glucose. *Brussels: International Diabetes Federation,* 2007, http://www.idf.org/webdata/docs/Guideline PMG final.pdf S. E. Inzucchi, R. M. Bergenstal, J. B. Buse, M. Diamant, E. Ferrannini, M. Nauck, A. L. Peters, A. Tsapas, R. Wender, and D. R. Matthews. Management of Hyperglycemia in Type 2 Diabetes: A Patient-Centered Approach: Position Statement of the American Diabetes Association (ADA) and the European Association for the Study of Diabetes (EASD). Diabetes care, 2012.

Reviews relating to basal insulin analogues and their characteristics and current clinical use can for example be found in:

T. Heise and T. R. Pieber. Towards peakless, reproducible and long-acting insulins. An assessment of the basal analogues based on isoglycaemic clamp studies. *Diabetes Obes Metab* 9 (5):648-659, 2007, and A. H. Barnett. A review of basal insulins. *Diabet Med* 20 (11):873-885, 2003.

Human insulin has three primary amino groups: the N-terminal group of the A-chain and of the B-chain and the $\epsilon$-amino group of $Lys^{B29}$. Several insulin derivatives which are substituted in one or more of these groups are known in the prior art.

In addition, long acting insulin compositions are known in the art. One main type of long acting insulin compositions comprises injectable aqueous suspensions of insulin crystals or amorphous insulin. In these compositions, the insulin compounds utilized typically are protamine insulin, zinc insulin or protamine zinc insulin.

WO 2005/012347 (Novo Nordisk A/S) discloses acylated insulin derivatives comprising additional negatively charge compared to the acylated insulins disclosed in WO 95/07931. The pharmaceutical formulation of these acylated insulins are given as 2, 3 or 4 zinc atoms per hexamer insulin.

WO 2010/049488 discloses an insulin derivative for the treatment of a condition or disease where administration of insulin will be of benefit, comprising administering, to a patient in need thereof, effective dosages of the insulin derivative, wherein said insulin derivative exhibits a prolonged profile of action and wherein said dosages are administered at intervals longer than 24 hours.

DESCRIPTION OF THE INVENTION

The present invention is based on the surprising finding that it is possible to treat a condition or a disease where administration of insulin would be of benefit, such as diabetes or hyperglycaemia, by administration of a pharmaceutical combination that comprises differently acting insulin-like compounds at a particular event in the day. In this respect, the combination is administered at the largest meal of the day for said subject.

According to the present invention, the combination comprises at least a first insulin-like compound and a second insulin-like compound.

The term "insulin-like compound" includes naturally occurring insulins, insulin analogues, insulin derivatives and insulin mimetics. Sometimes the insulin-like compounds are referred to as "insulin compounds", or the like.

According to the present invention, the first insulin-like compound is longer acting than the second insulin-like compound. In this respect, the first insulin-like compound has a longer insulin action than the second insulin-like compound.

According to the present invention, the combination is administered in an amount to achieve a beneficial glycaemic control in said subject.

According to the present invention, the beneficial glycaemic control in said subject is determined by at least the levels of $HbA_{1c}$ (glycosylated haemoglobin) in said subject after administration of said combination at the largest meal of the day for said subject.

The term "administration of said combination at the largest meal of the day for said subject" means that the combination is administered during or around—typically from a short while before, such as about 30 minutes before, or up to a short while afterwards, such as about 30 minutes afterwards—the largest meal of the day over a period of more than one day. As used herein, "at", "with" or "in relation to" the largest meal of the day equally include "during" the meal itself as well as a short time before and after said meal, e.g. up to about 30 minutes before first food ingestion and up to about 30 minutes after last food ingestion of said meal.

In other words, and for example, the combination is administered during or around (typically from a short while before, such as about 30 minutes before, or up to a short while afterwards, such as about 30 minutes afterwards) the largest meal of the day for every day (or at least substantially every day) for a period of at least about 1 week, or at least about 2 weeks, or at least about 3 weeks, or at least about 4 weeks, or at least about 5 weeks, or at least about 6 weeks, or at least about 7 weeks, or at least about 8 weeks, or at least about 9 weeks, or at least about 10 weeks, or at least about 15 weeks, or at least about 20 weeks, or at least about 25 weeks, or even longer.

In one aspect, the largest meal of the day is determined by said patient. In one aspect, said patient is instructed to determine which meal is the largest meal of the day. The largest meal of the day is not necessarily the same meal for each patient, i.e. not at the same time of the day. It may vary from patient to patient e.g. depending on patients' life style, culture, time constraints e.g due to work etc. For a given patient, the largest meal of the day is not necessarily the same meal every day, i.e. not at the same time of the day everyday. It may vary from day to day.

According to the present invention, the $HbA_{1c}$ levels are an important target. Up until now, it has proven to be difficult to achieve improvements in levels of $HbA_{1c}$ in patients suffering from a condition or a disease in a subject in need thereof where administration of insulin would be of benefit, such as type 1 diabetes, type 2 diabetes as well as for other forms of insulin requiring disease states (hyperglycaemia of any cause).

By use of the combination of the present invention it is possible to achieve improvements in levels of $HbA_{1c}$ in patients suffering from a condition or a disease in a subject in need thereof where administration of insulin would be of benefit, such as type 1 diabetes, type 2 diabetes as well as for other forms of insulin requiring disease states (hyperglycaemia of any cause). This is an important finding and has huge therapeutic value in the treatment of such conditions or diseases.

Hence, the combination comprising at least a first insulin-like compound and a second insulin-like compound according to the present invention can be used to treat a condition or a disease in a subject in need thereof where administration of insulin would be of benefit to said subject. Thus, diseases and conditions which are the primary targets for the use or method of the present invention are diabetes mellitus (type 1 or 2) or other conditions characterized by hyperglycaemia, and also metabolic diseases and conditions in general where the metabolic effects of insulin has a clinical relevance are of interest, such as pre-diabetes, impaired glucose tolerance, metabolic syndrome, obesity, cachexia, in vivo beta-cell loss/death, excessive appetite, and inflammation. All these types of conditions are known to or believed to benefit from a stable metabolic state in the subject who has the disease/condition.

Accordingly, any therapeutic regimen where administration of insulin or insulin compounds is included may be modified by implementing the present invention.

In one aspect, the beneficial glycaemic control by said combination is superior to any glycaemic control achieved by an equivalent dose of IGlar in said subject as determined by the levels of $HbA_{1c}$ in said subject after administration of IGlar for said subject.

The term "said combination is superior to any glycaemic control achieved by an equivalent dose of IGlar in said subject as determined by the levels of $HbA_{1c}$ in said subject after administration of IGlar for said subject" means that the combination is superior to an equivalent dose of IGlar under an administration regime according to the label of IGlar in achieving a better glycaemic control as determined by the levels of $HbA_{1c}$ in said subject after administration of either the combination or the IGlar.

IGlar (insulin glargine) is a basal insulin marketed by the company Sanofi Aventis under the tradename Lantus®. According to the leaflet in the Lantus packages, IGlar should be given once a day and at the same time every day.

In one aspect, the beneficial glycaemic control by said combination comprises decreasing the levels of $HbA_{1c}$ in said subject to about 7 or less after administration of said combination at the largest meal of the day. The decrease in the levels of $HbA_{1c}$ in said subject to about 7 can be achieved at about 26 weeks, or even less.

In one aspect, the beneficial glycaemic control by said combination is defined both as being superior to any glycaemic control achieved by an equivalent dose of IGlar in said subject as determined by the levels of $HbA_{1c}$ in said subject after administration of IGlar for said subject and comprising decreasing the levels of $HbA_{1c}$ in said subject to about 7 or less after administration of said combination at the largest meal of the day.

In addition to having a beneficial effect on the level of HbA1c, the combination of the present invention may also have a beneficial effect on the levels of blood glucose.

The combination of the present invention is administered at the largest meal of the day for said subject. This means that the combination of the present invention is administered with, or around the same time as, the largest meal of the day for said subject, typically from a short while before, such as about 30 minutes before, or up to a short while afterwards, such as about 30 minutes afterwards.

It is advantageous that the combination of the present invention achieves the beneficial glycaemic control as it provides flexibility to the subject. A number of advantages directly follow from such a flexible treatment regimen.

For example, convenience is improved for patients by the possibility for flexible administration. For example patients can adapt the administration to their life style rather than being dependent on dosage at fixed time points, which can be advantageous in cases of in compliance or distraction where a dose is administered earlier or later than the intended time of injection; if the patient is, e.g., travelling, a child or a teenager, doing sports or a shift worker; or for any other reason has an irregular lifestyle or for whom irregularities in daily routines occur or cannot be avoided. Another example where flexible administration is advantageous is if the patient lives in a nursing home or if the patient is otherwise dependent on assisted administration of insulin compounds. Improved convenience potentially improves patient compliance ultimately improving the long term outcome for the patient.

The patient has even further flexibility when compared to the use of basal insulins, like IGlar, that have to be injected at the same time every day.

Hence, we have surprisingly found that a beneficial glycaemic control (as defined herein) can be achieved by administering the combination of the present invention during or around the time of the largest meal, typically from a short while before, such as about 30 minutes before, or up to a short while afterwards, such as about 30 minutes afterwards.

In our experimental studies presented herein, IDegAsp was administered to patients with Type 2 diabetes at the largest meal of the day. The results presented herein were from a randomized controlled, Phase 3 Trial. In the Examples Section data are provided for the combination of IDegAsp—a soluble combination of ultra-long-acting insulin degludec (70%) and insulin aspart (30%)—that provides both mealtime and basal insulin coverage. This 26-week, open-label, treat-to-target trial investigated the efficacy and safety of IDegAsp in insulin-nave subjects with type 2 diabetes. In these studies, the participants (mean: 60.5 yrs; A1C 8.4%; FPG 162 mg/dL; BMI 25.1 kg/m$^2$; duration of diabetes 11.7 yrs) were randomized to once-daily (OD) injections of IDegAsp (n=147) or insulin glargine (IGlar; n=149), both ± up to 2 OADs (excluding SUs, DPP-4 inhibitors and glinides). IDegAsp was given before the largest meal of the day at the discretion of each participant (and maintained throughout the trial); IGlar was dosed as per label. Both insulins were titrated to FPG<90 mg/dL. After 26 weeks, mean HbA$_{1C}$ was 7.0% with IDegAsp and 7.3% with IGlar. The superiority of IDegAsp to IGlar was demonstrated (estimated treatment difference (ETD) IDegAsp-IGlar: −0.28%-points [−0.46; −0.10], p<0.001). Mean FPG was similar for IDegAsp and IGlar (103 vs. 100 mg/dL; ETD IDegAsp-IGlar: 2.7 mg/dL [−5.2; 10.8], p=NS). Confirmed hypoglycemia (PG<56 mg/dL) was reported for 44% of subjects in both groups. Also, IDegAsp was associated with numerically lower rates of overall confirmed (27%) and nocturnal confirmed hypoglycemia (25%) vs. IGlar (estimated rate ratio IDegAsp/IGlar: 0.73 [0.50; 1.08] p=NS and 0.75 [0.34; 1.64], p=NS, respectively). Mean daily insulin doses were similar between groups at end-of-trial (IDegAsp: 0.41 U/kg; IGlar: 0.41 U/kg) as were increases in body weight from baseline (0.7 kg both groups). Overall rates of adverse events were similar between groups with no treatment-specific pattern or clustering. In conclusion, the results show that IDegAsp dosed once daily with the largest meal of the day provided superior long-term glycemic control with a similar FPG to IGlar at a numerically lower rate of overall and nocturnal hypoglycemia. Thus, in summary, a once-daily administration of IDegAsp is superior to IGlar in subjects with Type 2 diabetes.

Hence, in our experimental studies presented herein, we found that the combination of LysB29(Nε-hexadecandioyl-γ-Glu) des(B30) human insulin and IAsp when given with the largest meal resulted in beneficial levels of HbA$_{1c}$, which levels were superiod to the levels achieved by the administration of IGlar (data not shown).

Our results are surprising when one considers the findings of Strojek et al (2009) Current Medical Research & Opinion vol 25 pages 2887 to 2894. Here, the authors studied once-daily initiation with biphasic insulin as part 30 versus IGlar in patients with type 2 diabetes inadequately controlled with oral drugs. At the end of the treatment, the authors found that the mean HbA1c level was 7.1% and 7.3% for BIAsp 30 and insulin glargine, respectively. The authors also found that the relative risk (RR) of experiencing a nocturnal hypoglycemic episode (00:00-06.00 a.m.) was significantly higher with BIAsp 30 than with insulin glargine (1.1 versus 0.5 episodes/year, RR ¼ 2.41, 95% CI [1.34; 4.34], p ¼ 0.003). The authors also reported on three major hypoglycemic episodes in each group.

Our findings are surprising as, in our background studies, we found that the combination of LysB29(Nε-hexadecandioyl-γ-Glu) des(B30) human insulin and IAsp when given with meal that was not the largest meal—such as breakfast—resulted in levels of HbA$_{1c}$ comparable to the levels achieved by the administration of IGlar (data not shown).

Diabetes

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by B-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

Other Indications

In one embodiment, the combination according to the present invention is used for the preparation of a medicament for the treatment or prevention of hyperglycemia including stress induced hyperglycemia, type 2 diabetes, impaired glucose tolerance, type 1 diabetes, burns, operation wounds, other diseases or injuries where an anabolic effect is needed in the treatment, myocardial infarction, stroke, coronary heart disease, other cardiovascular disorders, treatment of critically ill diabetic and non-diabetic patients and polyneuropathy.

In another embodiment, the combination according to the present invention is used as a medicament for delaying or preventing disease progression in type 2 diabetes.

In one embodiment of the invention, the combination according to the present invention is for use as a medicament for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, stroke, coronary heart disease and other cardiovascular disorders.

In a further embodiment the invention is related to a method for the treatment or prevention of hyperglycemia including stress induced hyperglycemia, type 2 diabetes, impaired glucose tolerance, type 1 diabetes, and burns, operation wounds and other diseases or injuries where an anabolic effect is needed in the treatment, myocardial infarction, coronary heart disease and other cardiovascular disorders, stroke, the method comprising administering to a patient in need of such treatment an effective amount for such treatment the combination according to the present invention.

Specific Combination Treatment

The treatment with the combination according to the present invention may also be combined with a second or more pharmacologically active substances, e.g., selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity.

The components of the combination according to the present invention may be administered simultaneously or sequentially. The factors may be supplied in single-dosage form wherein the single-dosage form contains both compounds, or in the form of a kit-of-parts comprising a preparation of the combination according to the present invention as a first unit dosage form and a preparation of the combination according to the present invention as a second unit dosage form. Whenever a first or second or third, etc., unit dose is mentioned throughout this specification this does not indicate the preferred order of administration, but is merely done for convenience purposes.

By "simultaneous" dosing of a preparation of the combination according to the present invention is meant administration of the compounds in single-dosage form, or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

Preferably the combination according to the present invention comprises the first insulin-like compound and the second insulin-like compound in the same formulation—i.e. in the same composition.

Insulin

The term "human insulin" as used herein means the human insulin hormone whose structure and properties are well-known. Human insulin has two polypeptide chains, named the A-chain and the B-chain. The A-chain is a 21 amino acid peptide and the B-chain is a 30 amino acid peptide, the two chains being connected by disulphide bridges: a first bridge between the cysteine in position 7 of the A-chain and the cysteine in position 7 of the B-chain, and a second bridge between the cysteine in position 20 of the A-chain and the cysteine in position 19 of the B-chain. A third bridge is present between the cysteines in position 6 and 11 of the A-chain.

In the human body, the hormone is synthesized as a single-chain precursor proinsulin (preproinsulin) consisting of a prepeptide of 24 amino acids followed by proinsulin containing 86 amino acids in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

An "insulin" according to the invention is herein to be understood as human insulin or an insulin from another species such as porcine or bovine insulin.

The term "insulin peptide" as used herein means a peptide which is either human insulin or an analog or a derivative thereof with insulin activity.

The term "parent insulin" as used herein is intended to mean an insulin before any modifications have been applied thereto.

Insulin Analogues

The term "insulin analogue" as used herein means a modified human insulin wherein one or more amino acid residues of the insulin have been substituted by other amino acid residues and/or wherein one or more amino acid residues have been deleted from the insulin and/or wherein one or more amino acid residues have been added and/or inserted to the insulin.

In one embodiment an insulin analogue comprises less than 10 amino acid modifications (substitutions, deletions, additions (including insertions) and any combination thereof) relative to human insulin, alternatively less than 9, 8, 7, 6, 5, 4, 3, 2 or 1 modification relative to human insulin.

Modifications in the insulin molecule are denoted stating the chain (A or B), the position, and the one or three letter code for the amino acid residue substituting the native amino acid residue.

By "desB30" or "B(1-29)" is meant a natural insulin B chain or an analogue thereof lacking the B30 amino acid and "A(1-21)" means the natural insulin A chain. Thus, e.g., A21Gly, B28Asp, desB30 human insulin is an analogue of human insulin where the amino acid in position 21 in the A chain is substituted with glycine, the amino acid in position 28 in the B chain is substituted with aspartic acid, and the amino acid in position 30 in the B chain is deleted.

Herein terms like "A1", "A2" and "A3" etc. indicates the amino acid in position 1, 2 and 3 etc., respectively, in the A chain of insulin (counted from the N-terminal end). Similarly, terms like B1, B2 and B3 etc. indicates the amino acid in position 1, 2 and 3 etc., respectively, in the B chain of insulin (counted from the N-terminal end). Using the one letter codes for amino acids, terms like A21A, A21G and A21Q designates that the amino acid in the A21 position is A, G and Q, respectively. Using the three letter codes for amino acids, the corresponding expressions are A21Ala, A21Gly and A21Gln, respectively.

Herein the terms "A(0)" or "B(0)" indicate the positions of the amino acids N-terminally to A1 or B1, respectively. The terms A(−1) or B(−1) indicate the positions of the first amino acids N-terminally to A(0) or B(0), respectively. Thus A(−2) and B(−2) indicate positions of the amino acids N-terminally to A(−1) and B(−1), respectively, A(−3) and B(−3) indicate positions of the amino acids N-terminally to A(−2) and B(−2), respectively, and so forth. The terms A22 or B31 indicate the positions of the amino acids C-terminally to A21 or B30, respectively. The terms A23 or B32 indicate the positions of the first amino acids C-terminally to A22 or B31, respectively. Thus A24 and B33 indicate positions of the amino acids C-terminally to A23 and B32, respectively, and so forth.

Herein, the term "amino acid residue" is an amino acid from which, formally, a hydroxy group has been removed from a carboxy group and/or from which, formally, a hydrogen atom has been removed from an amino group.

Examples of insulin analogues are such wherein Pro in position 28 of the B chain is substituted with Asp, Lys, Leu, Val, or Ala and/or Lys at position B29 is substituted with Pro, Glu or Asp. Furthermore, Asn at position B3 may be substituted with Thr, Lys, Gln, Glu or Asp. The amino acid residue in position A21 may be substituted with Gly. Also one or more amino acids may be added to the C-terminal of the A-chain and/or B-chain such as, e.g., Lys. The amino acid in position B1 may be substituted with Glu. The amino acid in position B16 may be substituted with Glu or His. Further examples of insulin analogues are the deletion analogues, e.g., analogues where the B30 amino acid in human insulin has been deleted (des(B30) human insulin), insulin analogues wherein the B1 amino acid in human insulin has been deleted (des(B1) human insulin), des(B28-B30) human insulin and des(B27) human insulin. Insulin analogues wherein the A-chain and/or the B-chain have an N-terminal extension and insulin analogues wherein the A-chain and/or the B-chain have a C-terminal extension such as with two arginine residues added to the C-terminal of the B-chain are also examples of insulin analogues. Further examples are insulin analogues comprising combinations of the mentioned mutations. Insulin analogues wherein the amino acid in position A14 is Asn, Gln, Glu, Arg, Asp, Gly or His, the amino acid in position B25 is His and which optionally further comprises one or more additional mutations are further examples of insulin analogues. Insulin analogues of human insulin wherein the amino acid residue in position A21 is Gly and wherein the insulin analogue is further extended in the C-terminal with two arginine residues are also examples of insulin analogues.

Further examples of insulin analogues include:

DesB30 human insulin; AspB28 human insulin; AspB28, desB30 human insulin; LysB3, GluB29 human insulin; LysB28, ProB29 human insulin; GlyA21, ArgB31, ArgB32 human insulin; GluA14, HisB25 human insulin; HisA14, HisB25 human insulin; GluA14, HisB25, desB30 human insulin; HisA14, HisB25, desB30 human insulin; GluA14, HisB25, desB27, desB28, desB29, desB30 human insulin; GluA14, HisB25, GluB27, desB30 human insulin; GluA14, HisB16, HisB25, desB30 human insulin; HisA14, HisB16, HisB25, desB30 human insulin; HisA8, GluA14, HisB25, GluB27, desB30 human insulin; HisA8, GluA14, GluB1, GluB16, HisB25, GluB27, desB30 human insulin; and HisA8, GluA14, GluB16, HisB25, desB30 human insulin.

Hence, the insulin analogue for use in the present invention can include a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues For example, the insulin analogues may be such wherein position 28 of the B chain may be modified from the natural Pro residue to one of Asp, Lys, or Ile. In another embodiment Lys at position B29 is modified to Pro. In one embodiment B30 may be Lys and then B29 can be any codable amino acid except Cys, Met, Arg and Lys.

For example, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly.

For example, Asn at position B3 may be modified to Lys or Asp.

Further examples of insulin analogues are des(B30) human insulin; des(B30) human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

The expression "a codable amino acid" or "a codable amino acid residue" is used to indicate an amino acid or amino acid residue which can be coded for by a triplet ("codon") of nucleotides.

Further examples of insulin analogues include those that have an amino acid residue having a carboxylic acid group in the side chain. The expression "an amino acid residue having a carboxylic acid group in the side chain" designates amino acid residues like Asp, Glu and hGlu. The amino acids can be in either the L- or D-configuration. If nothing is specified it is understood that the amino acid residue is in the L configuration.

Further examples of insulin analogues include those that have an amino acid residue having an amino acid residue having a neutral side chain. The expression "an amino acid residue having a neutral side chain" designates amino acid residues like Gly, Ala, Val, Leu, Ile, Phe, Pro, Ser, Thr, Cys, Met, Tyr, Asn and Gln.

Insulin Derivatives

The term "insulin derivative" as used herein means a chemically modified parent insulin or an analogue thereof, wherein the modification(s) are in the form of attachment of amides, carbohydrates, alkyl groups, acyl groups, esters, PEGylations, and the like. Examples of derivatives of human insulin according to the invention are LysB29(Nε-hexadecandioyl-γ-Glu) des(B30) human insulin, $N^{\epsilon B29}$-ω-carboxy-pentadecanoyl-γ-L-glutamylamide desB30 human insulin, $N^{\epsilon B29}$-ω-carboxy-pentadecanoyl-γ-amino-butanoyl desB30 human insulin, $N^{\epsilon B29}$-(Nα-(Sar-OC(CH2)13CO)-γ-Glu) desB30 human insulin, $N^{\epsilon}$B29-hexadecandioyl-γ-amino-butanoyl desB30 human insulin, $N^{\epsilon}$B29-hexadecandioyl-γ-L-Glu-amide desB30 insulin.

To effect covalent attachment of the polymer molecule(s) to the polypeptide, the hydroxyl end groups of the polymer molecule are provided in activated form, i.e. with reactive functional groups. Suitable activated polymer molecules are commercially available, e.g. from Shearwater Corp., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Corp. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. No. 5,932,462 and U.S. Pat. No. 5,643,575.

The conjugation of the polypeptide and the activated polymer molecules is conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfydryl, succinimidyl, maleimide, vinysulfone or haloacetate).

Hence, the insulin derivative of the present invention can include a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or acylating a free amino group or a hydroxy group.

Pharmaceutical Protein Formulations

Injectable compositions containing the combination of the present invention can be prepared using the conventional techniques of the pharmaceutical industry which involve dissolving and mixing the ingredients as appropriate to give the desired end product. Thus, according to one procedure, the combination of the present invention is dissolved in an amount of water which is somewhat less than the final volume of the composition to be prepared. An isotonic agent, a preservative and a buffer is added as required and the pH value of the solution is adjusted, if necessary, using an acid, for example, hydrochloric acid, or a base, for example, aqueous sodium hydroxide, as needed. Finally, the volume of the solution is adjusted with water to give the desired concentration of the ingredients.

More precisely, an insulin preparation of this invention, for example a solution or suspension, may be prepared by dissolving the combination of the present invention in an aqueous medium at slightly acidic conditions, for example, in a concentration in the range from about 240 to about 2400 nmole/ml. The aqueous medium is made isotonic, for example, with sodium chloride or glycerol. Furthermore, the aqueous medium may contain buffers such as acetate or citrate, preservatives such as m-cresol or phenol and zinc ions, for example, zinc can be present in a concentration of above 4 zinc atoms per 6 molecules of the insulin derivatives, such as 4.5 zinc atoms per 6 molecules of the insulin derivatives, 5 zinc atoms per 6 molecules of the insulin derivatives, 6 zinc atoms per 6 molecules of the insulin derivatives or up to 12 zinc atoms per 6 molecules of the insulin derivatives. The pH value of the solution is adjusted towards neutrality without getting too close to the isoelectric point of the compound of this invention in order to avoid potential precipitation. The pH value of the final insulin preparation depends upon which compounds of this invention are used, the concentration of zinc ions and the concentration of the compound of this invention. The insulin preparation is made sterile, for example, by sterile filtration.

First Insulin-Like Compound

The combination of the present invention comprises a first insulin-like compound that is longer acting than the second insulin-like compound.

In one embodiment, the first and/or the second insulin-like compound exhibits in physiological conditions, at least in part, the insulin receptor binding and/or activation (potency) of the naturally occurring insulin, preferably, at least 0.01% of the insulin receptor binding and/or activation (potency) of the naturally occurring insulin, for example, at least 0.1%, at least, 1%, at least 5%, at least 10%, at least 15%, at least 20%, at least 25% at least 50%, at least 65%, at least 75%, at least 85%, at least 95%, at least 100%, at least 110%, at least 120%, at least 130%, at least 140% or at least 150% of the insulin receptor binding and/or activation (potency) of the naturally occurring insulin Insulin receptor binding may be determined by any suitable means known in the art. However preferably, insulin receptor binding is determined using the method provided in the foregoing examples (assay (I)—Insulin receptor binding).

Insulin receptor activation (potency) may be determined by any suitable means known in the art. However preferably, insulin receptor binding is determined using the method provided in the foregoing examples (assay (II)—Potency).

In one embodiment, the first and/or second insulin compound has a half-life of at least 18 hours, such as at least 24 hours, wherein the half-life may be determined as described in Clinical Example 1 herein. In one embodiment the first and/or second insulin compound has a half-life of at least 12 hours, such as at least 12 hours and less than 24 hours, wherein the half-life may be determined as described in Clinical Example 1 herein.

In this respect, for some embodiments the first insulin-like compound is at least long acting insulin.

In one embodiment, the term "long acting insulin" means that the insulin-like compound has an insulin action or prolonged profile of action (e.g. keeps blood sugar levels at a steady and stable level) for up to 24 hours.

In one embodiment, a long lasting insulin exhibits a half life of at least 10 hours in physiological conditions when injected subcutaneously, for example, at least 12.5 hours, at least 15 hours, at least 17.5 hours, at least 20 hours, at least 22.5 hours, at least 25 hours, at least 27.5 hours, at least 30 hours, at least 32.5, at least 35 hours, at least 37.5 hours or at least 40 hours. Preferably, a long lasting insulin also exhibits a half life of less than or equal to 24 hr in physiological conditions when injected subcutaneously, for example, less than or equal to 22 hr, less than or equal to 20 hr, less than or equal to 18 hr, less than or equal to 16 hr or less than or equal to 14 hr.

Insulin half life may be determined by any suitable means known in the art (for example, see Gough S C, Harris S, Woo V, Davies M, 2013, 'Insulin degludec: overview of a novel ultra long-acting basal insulin' *Diabetes Obes Metab.*, 15(4): 301-9; and/or Heise T, Nosek L, Bøttcher S G, Hastrup H, Haahr H, 2012, 'Ultra-long-acting insulin degludec has a flat and stable glucose-lowering effect in type 2 diabetes' *Diabetes Obes Metab.*, 14(10):944-50, the disclosures of which are incorporated herein by reference). Insulin half-life may also be determined as described in Clinical Example 1 herein. Preferably, insulin half-life is determined using the method provided in Assay (III) herein.

In this respect, for some embodiments the first insulin-like compound is an ultra long acting insulin.

In one embodiment, the term "ultra long acting insulin" means that the insulin-like compound has an insulin action or prolonged profile of action (e.g. keeps blood sugar levels at a steady and stable level) for over 24 hours.

In one embodiment, a ultra long lasting insulin exhibits a half life of greater than 18 hr in physiological conditions when injected subcutaneously, for example, greater than 20 hr, greater than 22 hr or greater than 24 hr.

For some embodiments the first insulin-like compound has a prolonged profile of action.

In one embodiment "prolonged profile of action" is defined as an average time to loss of glucose control of at least 20 hours, wherein the average time to loss of glucose control may be determined as described in Clinical Example 1 herein.

In one embodiment the insulin-like compound used in the present invention has 1) a sufficiently prolonged profile of action and/or half-life in most subjects and optionally 2) a relatively flat and stable shape of the activity profile in order not to cause undue increase in insulin action when used with a short dosing interval. An indication of the duration of action in clinical use may be obtained under experimental conditions such as by use of the euglycaemic glucose clamp procedure (L. Heinemann and J. H. Anderson-Jr. Measurement of insulin absorption and insulin action. *Diabetes Technol Ther* 6 (5):698-718, 2004), which is used in Clinical Example 1. An indication of the flatness of the activity profile in clinical use may be obtained under experimental conditions as described in Clinical Example 1 or Clinical Example 2. An indication of the stability of the activity profile in clinical use may be obtained under experimental conditions as described in Clinical Example 1 or Clinical Example 2.

In one embodiment, the first insulin-like compound does not have a relatively high peak activity profile. This peak is defined as the maximum in a curve when glucose infusion is plotted against time since administration of the drug. An indication of the peak of the activity profile in clinical use may be obtained under experimental conditions as described in Clinical Example 1 or Clinical Example 2.

Preferably, the first and/or second insulin-like insulin induce in a subject a maximum deviation from mean insulin concentration (AUCF %) over a 24 hour period of ≤±18, for example, ≤±17, ≤±16, ≤±15, ≤±14, ≤±13, ≤±12, ≤±11, ≤±10, ≤±9, ≤±8, ≤±7, ≤±6, ≤±5, ≤±4, ≤±3, ≤±2, ≤±1, ≤±0.5, ≤±0.1.

Maximum deviation from mean insulin concentration (AUCF %) may be determined by any suitable means known in the art (see, for example, Heise et al., Poster EASD 2011).

In one embodiment, the first and/or second insulin-like insulin preferably provide a stable and evenly distributed glucose-lowering effect over the dosing interval. For example, glucose infusion rate (GIR) over a 24-h dosing interval (tau) quantified by estimating the ratio of AUC for sub-areas under the GIR profiles for all four 6-hour measurement intervals (proportion of GIR AUC: $AUC_{GIR,0-6h,SS}/AUC_{GIR,\tau,SS}$; $AUC_{GIR,6-12h,SS}/AUC_{GIR,\tau,SS}$; $AUC_{GIR,12-18h,SS}/AUC_{GIR,\tau,SS}$; $AUC_{GIR,18-24h,SS}/AUC_{GIR,\tau,SS}$) should be close to 25:25:25:25% distribution (preferably ±8%, for example, ±4%, ±3%, ±2%, ±1%, ±0.5% or ±0.1%).

In addition, the fluctuation in GIR across a dosing interval is preferably as small as possible. Fluctuation in GIR can be evaluated by $AUC_{FGIR,\tau}$: which estimates how much an individual's GIR profile deviates from his/her mean GIR over 24 h). Preferably, $AUC_{FGIR,\tau}$ is ≤58 (for example, ≤57, ≤56, ≤55, ≤54, ≤53, ≤52, ≤51 or ≤50). Fluctuation in GIR ($AUC_{FGIR,\tau}$) can be evaluated by any suitable method known in the art. However, in one embodiment GIR ($AUC_{FGIR,\tau}$) is evaluated according to the method described in Heise et al., 2012, *Diabetes, Obesity and Metabolism*, 14(9):859-64.

In one preferred embodiment, the first insulin-like compound is any one or more of the compounds disclosed in WO 2005/012347. In some instances, these compounds are referred as being "the '347 derivatives".

The present invention includes embodiments where the first insulin-like compound is a '347 derivative, i.e. a derivative of a naturally occurring insulin or an insulin analogue has a side chain attached either to the α-amino group of the N-terminal amino acid residue of the B chain or to the ε-amino group of a Lys residue present in the B chain of the parent insulin, the side chain being of the general formula (I):

—W—X—Y—Z wherein W is:
an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;
a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to the α-amino group of the N-terminal amino acid residue of the B chain or to the ε-amino group of a Lys residue present in the B chain of the parent insulin;

wherein X is:
—CO—;
—COCH(COOH)C̲O—;
—CON(CH₂COOH)CH₂C̲O—;
—CON(CH₂COOH)CH₂CON(CH₂COOH)CH₂C̲O—;
—CON(CH₂CH₂COOH)CH₂CH₂C̲O—;
—CON(CH₂CH₂COOH)CH₂CH₂CON(CH₂CH₂COOH)CH₂CH₂C̲O—;
—CONHCH(COOH)(CH₂)₄NHC̲O—;
—CON(CH₂CH₂COOH)CH₂C̲O—; or
—CON(CH₂COOH)CH₂CH₂C̲O—.
that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

wherein Y is:
—(CH₂)ₘ— where m is an integer in the range of 6 to 32;
a divalent hydrocarbon chain comprising 1, 2 or 3 —CH=CH— groups and a number of —CH₂— groups sufficient to give a total number of carbon atoms in the chain in the range of 10 to 32;
a divalent hydrocarbon chain of the formula —(CH₂)ᵥC₆H₄(CH₂)w— wherein v and w are integers or one of them is zero so that the sum of v and w is in the range of 6 to 30; and wherein Z is:
—COOH;
—CO-Asp;
—CO-Glu;
—CO-Gly;
—CO-Sar;
—CH(COOH)₂;
—N(CH₂COOH)₂;
—SO₃H; or
—PO₃H;
and any Zn²⁺ complexes thereof, provided that when W is a covalent bond and X is —CO—, then Z is different from —COOH.

In one embodiment the side chain —W—X—Y—Z is attached to the α-amino group of the N-terminal amino acid residue of the B chain of the parent insulin.

In another embodiment of the invention, side chain —W—X—Y—Z is attached to the ε-amino group of a Lys residue present in the B chain of the parent insulin.

In one more specific aspect of this embodiment, the side chain —W—X—Y—Z is attached to the ε-amino group of a Lys residue present in position 28 of the B chain.

In a further more specific aspect of this embodiment, the side chain —W—X—Y—Z is attached to the ε-amino group of a Lys residue present in position 29 of the B chain.

In a further more specific aspect of this embodiment, the side chain —W—X—Y—Z is attached to the ε-amino group of a Lys residue present in position 30 of the B chain.

The substructure W of the side chain —W—X—Y—Z can be a covalent bond. Alternatively, W can be a residue of an α-amino acid having a carboxylic acid group in the side chain and comprising a total of from 4 to 10 carbon atoms. Specifically, W can be the residue of an α-amino acid, that can be coded for by the genetic code. Thus, W can, for example, be selected from the group consisting of α-Asp, β-Asp, α-Glu, and γ-Glu. Further options for W are for example α-hGlu and δ-hGlu.

In a further embodiment, W is a chain composed of two α-amino acid residues of which one has from 4 to 10 carbon atoms and a carboxylic acid group in the side chain while the other has from 2 to 11 carbon atoms but no free carboxylic acid group. The α-amino acid residue with no free carboxylic acid group can be a neutral, codable α-amino acid residue. Examples of W according to this embodiment are: α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

In a further embodiment, W is a chain composed of two α-amino acid residues, independently having from 4 to 10 carbon atoms, and both having a carboxylic acid group in the side chain. One of these α-amino acid residues or both of them can be codable α-amino acid residues. Examples of W according to this embodiment are: α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

In a further embodiment, W is a chain composed of three α-amino acid residues, independently having from 4 to 10 carbon atoms, the amino acid residues of the chain being selected from the group of residues having a neutral side chain and residues having a carboxylic acid group in the side chain so that the chain has at least one residue which has a carboxylic acid group in the side chain. In one embodiment, the amino acid residues are codable residues.

In a further embodiment, W is a chain composed of four α-amino acid residues, independently having from 4 to 10 carbon atoms, the amino acid residues of the chain being selected from the group having a neutral side chain and residues having a carboxylic acid group in the side chain so that the chain has at least one residue which has a carboxylic acid group in the side chain. In one embodiment, the amino acid residues are codable residues.

In one embodiment W can be connected to the ε-amino group of the Lys residue in the B-chain via an urea derivative.

The substructure X of the side chain —W—X—Y—Z can be a group of the formula —$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —COCH(COOH)$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$COOH)CH$_2$CON(CH$_2$COOH)CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

In a further embodiment, the substructure X of the side chain can be a group of the formula —CON(CH$_2$CH$_2$COOH)CH$_2$CH$_2$CON(CH$_2$CH$_2$COOH)CH$_2$CH$_2$$\underline{C}$O— that, via a bond from the underscored carbonyl carbon, forms an amide bond with an amino group in W or, when W is a covalent bond, with the N-terminal α-amino group in the B chain or with the ε-amino group of a Lys residue present in the B chain of the parent insulin.

The substructure Y of the side chain —W—X—Y—Z can be a group of the formula —(CH$_2$)$_m$— where m is an integer in the range of from 6 to 32, from 8 to 20, from 12 to 20, or from 12-16.

In another embodiment, Y is a divalent hydrocarbon chain comprising 1, 2 or 3 —CH═CH— groups and a number of —CH$_2$— groups sufficient to give a total number of carbon atoms in the chain in the range of from 6 to 32, from 10 to 32, from 12 to 20, or from 12-16.

In another embodiment, Y is a divalent hydrocarbon chain of the formula —(CH$_2$)$_v$C$_6$H$_4$(CH$_2$)$_w$— wherein v and w are integers or one of them is zero so that the sum of v and w is in the range of from 6 to 30, from 10 to 20, or from 12-16.

In one embodiment, the substructure Z of the side chain —W—X—Y—Z is —COOH provided that when W is a covalent bond and X is —CO—, then Z is different from —COOH. In one embodiment Z is —COOH. In another embodiment, Z is —CO-Asp. In another embodiment, Z is —CO-Glu. In another embodiment, Z is —CO-Gly. In another embodiment, Z is —CO-Sar. In another embodiment, Z is —CH(COOH)$_2$. In another embodiment, Z is —N(CH$_2$COOH)$_2$. In another embodiment, Z is —SO$_3$H. In another embodiment, Z is —PO$_3$H.

In a further embodiment W is selected from the group consisting of α-Asp, β-Asp, α-Glu, and γ-Glu; X is —CO— or —COCH(COOH)CO; Y is —(CH$_2$)$_m$— where m is an integer in the range of 12-18 and Z is —COOH or —CH(COOH)$_2$.

The insulin moiety—in the present text also referred to as the parent insulin—of a '347 derivative can be a naturally occurring insulin such as human insulin or porcine insulin. Alternatively, the parent insulin can be an insulin analogue.

In one group of parent insulin analogues, the amino acid residue at position A21 is Asn.

In another group of parent insulin analogues, the amino acid residue at position A21 is Gly. Specific examples from this group of analogues are Gly$^{A21}$ human insulin, Gly$^{A21}$ des(B30) human insulin; and Gly$^{A21}$Arg$^{B31}$Arg$^{B32}$ human insulin.

In another group of parent insulin analogues, the amino acid residue at position B1 has been deleted. A specific example from this group of parent insulin analogues is des(B1) human insulin.

In another group of parent insulin analogues, the amino acid residue at position B30 has been deleted. A specific example from this group of parent insulin analogues is des(B30) human insulin.

In another group of parent insulin analogues, the amino acid residue at position B28 is Asp. A specific example from this group of parent insulin analogues is Asp$^{B28}$ human insulin) or otherwise stated as AspB28).

In another group of parent insulin analogues, the amino acid residue at position B28 is Lys and the amino acid residue at position B29 is Pro. A specific example from this group of parent insulin analogues is Lys$^{B28}$Pro$^{B29}$ human insulin.

In another group of parent insulin analogues the amino acid residue in position B30 is Lys and the amino acid residue in position B29 is any codable amino acid except Cys, Met, Arg and Lys. An example is an insulin analogue where the amino acid residue at position B29 is Thr and the amino acid residue at position B30 is Lys. A specific example from this group of parent insulin analogues is Thr$^{B29}$Lys$^{B30}$ human insulin.

In another group of parent insulin analogues, the amino acid residue at position B3 is Lys and the amino acid residue at position B29 is Glu. A specific example from this group of parent insulin analogues is Lys$^{B3}$Glu$^{B29}$ human insulin.

In one embodiment the parent insulin is selected from the group consisting of human insulin; des(B1) human insulin; des(B30) human insulin; GlyA21 human insulin; GlyA21 des(B30)human insulin; AspB28 human insulin; porcine insulin; LysB28ProB29 human insulin; GlyA21ArgB31ArgB32 human insulin; and LysB3GluB29 human insulin.

In one embodiment the first insulin-like compound in the invention has a sufficient prolonged profile of action in most subjects and optionally a relatively flat and stable shape of the activity profile.

In one embodiment the first insulin-like compound has a sufficient prolonged profile of action in most subjects defined as an average time to loss of glucose control of at least 20 hours, such between 20 and 50 hours, 20 and 45 hours, 24 and 45 hours, 26 and 45 hours, 30 and 50 hours, 35 and 50 hours, at least 26 hours, more than 26 hours, more than 26 hours and up to 50 hours, more than 26 hours and up to 50 hours, at least 28 hours, between 28 and 50 hours, at least 30 hours, between 30 and 45 hours, at least 35 hours, between 35 and 45 hours, at least 38 hours, at least about 40 hours up to about 45 hours, or of about 40 hours after administration of said insulin, wherein the prolonged profiled of action maybe determined as described in Clinical Example 1 herein.

In one embodiment the first insulin-like compound has a sufficient prolonged profile of action in most subjects defined as a mean terminal half-life of at least 12 hours, at least 14 hours, at least 16 hours, at least 18 hours, at least 20 hours, at least 22 hours, at least 24 hours, between 12 and 50 hours, 14 and 50 hours, 16 and 50 hours, 18 and 50 hours, 20 and 50 hours, 22 and 50 hours, 24 and 50 hours, 12 and 40 hours, 14 and 40 hours, 16 and 40 hours, 18 and 40 hours, at least 20 hours, at least 24 hours and up to 50 hours, between 18 and 36 hours, 20 and 36 hours, 22 and 36 hours, 24 and 36 hours, 25 and 36 hours, 26 and 36 hours, wherein the mean terminal half-life may be determined as described in Clinical Example 1 herein.

In another embodiment the first insulin-like compound in the invention has a prolonged profile of action and a relatively flat and stable shape of the activity profile.

Examples of '347 derivatives useful as the first insulin-like compound in the invention are the following compounds:

N$^{εB29}$—(N$^α$—(HOOC(CH$_2$)$_{14}$CO)-γ-Glu) des(B30) human insulin; O454

N$^{εB29}$—(N$^α$—(HOOC(CH$_2$)$_{15}$CO)-γ-Glu) des(B30) human insulin; O467

N$^{εB29}$—(N$^α$—(HOOC(CH$_2$)$_{16}$CO)-γ-Glu) des(B30) human insulin; O456

N$^{εB29}$—(N$^α$—(HOOC(CH$_2$)$_{17}$CO)-γ-Glu) des(B30) human insulin; No number yet N$^{εB29}$—(N$^α$—(HOOC(CH$_2$)$_{18}$CO)-γ-Glu) des(B30) human insulin; O458

N$^{εB29}$—(N$^α$—(HOOC(CH$_2$)$_{16}$CO)-γ-Glu-N-(γ-Glu)) des(B30) human insulin; O459

N$^{εB29}$—(N$^α$-(Asp-OC(CH$_2$)$_{16}$CO)-γ-Glu) des(B30) human insulin; O460

N$^{εB29}$—(N$^α$-(Glu-OC(CH$_2$)$_{14}$CO)-γ-Glu) des(B30) human insulin; O461

N$^{εB29}$—(N$^α$-(Glu-OC(CH$_2$)$_{14}$CO—) des(B30) human insulin; O462

N$^{εB29}$—(N$^α$-(Asp-OC(CH$_2$)$_{16}$CO—) des(B30) human insulin; O463

N$^{εB29}$—(N$^α$—(HOOC(CH$_2$)$_{16}$CO)-α-Glu-N-(β-Asp)) des(B30) human insulin; O466

N$^{εB29}$—(N$^α$-(Gly-OC(CH$_2$)$_{13}$CO)-γ-Glu) des(B30) human insulin; O468

N$^{εB29}$—(N$^α$-(Sar-OC(CH$_2$)$_{13}$CO)-γ-Glu) des(B30) human insulin;

N$^{εB29}$—(N$^α$—(HOOC(CH$_2$)$_{13}$CO)-γ-Glu) des(B30) human insulin;

(N$^{εB29}$—(N$^α$—(HOOC(CH$_2$)$_{13}$CO)-β-Asp) des(B30) human insulin; O454

N$^{εB29}$—(N$^α$—(HOOC(CH$_2$)$_{13}$CO)-α-Glu) des(B30) human insulin; O454

N$^{εB29}$—(N$^α$—(HOOC(CH$_2$)$_{16}$CO)-γ-D-Glu) des(B30) human insulin; O454

$N^{\epsilon B29}$—($N^\alpha$—(HOOC(CH$_2$)$_{14}$CO)-β-D-Asp) des(B30) human insulin; O454

$N^{\epsilon B29}$—(N—HOOC(CH$_2$)$_{16}$CO-β-D-Asp) des(B30) human insulin;

$N^{\epsilon B29}$—(N—HOOC(CH$_2$)$_{14}$CO-IDA) des(B30) human insulin;

$N^{\epsilon B29}$—[N—(HOOC(CH$_2$)$_{16}$CO)—N-(carboxyethyl)-Gly] des(B30) human insulin;

$N^{\epsilon B29}$—[N—(HOOC(CH$_2$)$_{14}$CO)—N-(carboxyethyl)-Gly] des(B30) human insulin; and $N^{\epsilon B29}$—[N—(HOOC(CH$_2$)$_{14}$CO)—N-(carboxymethyl)-β-Ala] des(B30) human insulin.

In one embodiment the first insulin-like compound is $N^{\epsilon B29}$—($N^\alpha$—(HOOC(CH$_2$)$_{14}$CO)-γ-Glu) des(B30) human insulin.

In one embodiment the first insulin-like compound is $N^{\epsilon B29}$—($N^\alpha$—(HOOC(CH$_2$)$_{15}$CO)-γ-Glu) des(B30) human insulin.

In one embodiment the first insulin-like compound is $N^{\epsilon B29}$—($N^\alpha$—(HOOC(CH$_2$)$_{16}$CO)-γ-Glu) des(B30) human insulin.

In one embodiment the first insulin-like compound is $N^{\epsilon B29}$—($N^\alpha$—(HOOC(CH$_2$)$_{17}$CO)-γ-Glu) des(B30) human insulin.

In one embodiment the first insulin-like compound is $N^{\epsilon B29}$—($N^\alpha$—(HOOC(CH$_2$)$_{18}$CO)-γ-Glu) des(B30) human insulin.

In one embodiment the first insulin-like compound is $N^{\epsilon B29}$—($N^\alpha$—(HOOC(CH$_2$)$_{16}$CO)-γ-Glu-N-(γ-Glu)) des(B30) human insulin.

In one embodiment the first insulin-like compound is $N^{\epsilon B29}$—($N^\alpha$-(Asp-OC(CH$_2$)$_{16}$CO)-γ-Glu) des(B30) human insulin.

In one embodiment the first insulin-like compound is $N^{\epsilon B29}$—($N^\alpha$-(Glu-OC(CH$_2$)$_{14}$CO)-γ-Glu) des(B30) human insulin.

In one embodiment the first insulin-like compound is $N^{\epsilon B29}$—($N^\alpha$-(Glu-OC(CH$_2$)$_{14}$CO—) des(B30) human insulin.

In one embodiment the first insulin-like compound is $N^{\epsilon B29}$—($N^\alpha$-(Asp-OC(CH$_2$)$_{16}$CO—) des(B30) human insulin.

In one embodiment the first insulin-like compound is $N^{\epsilon B29}$—($N^\alpha$—(HOOC(CH$_2$)$_{16}$CO)-α-Glu-N-(β-Asp)) des(B30) human insulin.

In one embodiment the first insulin-like compound is $N^{\epsilon B29}$—($N^\alpha$-(Gly-OC(CH$_2$)$_{13}$CO)-γ-Glu) des(B30) human insulin.

In one embodiment the first insulin-like compound is $N^{\epsilon B29}$—($N^\alpha$-(Sar-OC(CH$_2$)$_{13}$CO)-γ-Glu) des(B30) human insulin.

In one embodiment the first insulin-like compound is $N^{\epsilon B29}$—($N^\alpha$—(HOOC(CH$_2$)$_{13}$CO)-γ-Glu) des(B30) human insulin.

In one embodiment the first insulin-like compound is ($N^{\epsilon B29}$—($N^\alpha$—(HOOC(CH$_2$)$_{13}$CO)-β-Asp) des(B30) human insulin.

In one embodiment the first insulin-like compound is $N^{\epsilon B29}$—($N^\alpha$—(HOOC(CH$_2$)$_{13}$CO)-α-Glu) des(B30) human insulin.

In one embodiment the first insulin-like compound is $N^{\epsilon B29}$—($N^\alpha$—(HOOC(CH$_2$)$_{16}$CO)-γ-D-Glu) des(B30) human insulin.

In one embodiment the first insulin-like compound is $N^{\epsilon B29}$—($N^\alpha$—(HOOC(CH$_2$)$_{14}$CO)-β-D-Asp) des(B30) human insulin.

In one embodiment the first insulin-like compound is $N^{\epsilon B29}$—($N^\alpha$—(HOOC(CH$_2$)$_{14}$CO)-β-D-Asp) des(B30) human insulin.

In one embodiment the first insulin-like compound is $N^{\epsilon B29}$—(N—HOOC(CH$_2$)$_{16}$CO-β-D-Asp) des(B30) human insulin.

In one embodiment the first insulin-like compound is $N^{\epsilon B29}$—(N—HOOC(CH$_2$)$_{14}$CO-IDA) des(B30) human insulin.

In one embodiment the first insulin-like compound is $N^{\epsilon B29}$—[N—(HOOC(CH$_2$)$_{16}$CO)—N-(carboxyethyl)-Gly] des(B30) human insulin.

In one embodiment the first insulin-like compound is $N^{\epsilon B29}$—[N—(HOOC(CH$_2$)$_{14}$CO)—N-(carboxyethyl)-Gly] des(B30) human insulin.

In one embodiment the first insulin-like compound is $N^{\epsilon B29}$—[N—(HOOC(CH$_2$)$_{14}$CO)—N-(carboxymethyl)-β-Ala] des(B30) human insulin.

O469

When zinc complexes of a '347 derivative are provided, above four Zn$^{2+}$ ions, five Zn$^{2+}$ ions six Zn$^{2+}$ ions or up to 12 Zn$^{2+}$ ions will be present per 6 molecules of the '347 derivative. In one embodiment the insulin derivative is in the form of a zinc complex, wherein 6 molecules of the '347 derivative binds two zinc ions, three zinc ions, four zinc ions, five zinc ions, six zinc ions, seven zinc ions, eight zinc ions, nine zinc ions or ten zinc ions. Solutions of zinc complexes of the insulin derivatives will contain mixtures of such species.

Details pertaining to the preparation, formulation, pharmacology and other characteristics of relevance for the '347 derivatives are set forth in WO 2005/012347, which is hereby incorporated by reference herein.

The first insulin-like compound may be any one of the compounds disclosed in WO 2007/128817, which is are incorporated by reference herein.

For some embodiments the first insulin-like compound is a basal insulin compound.

The combination of the present invention may also comprise one or more additional first insulin-like compound(s).

The one or more additional first insulin-like compound(s) may be any one or more of the first insulin-like compounds presented above.

Second Insulin-Like Compound

The combination of the present invention comprises a second insulin-like compound that is faster acting than the second insulin-like compound.

In this respect, for some embodiments the second insulin-like compound is a rapid acting insulin.

The term "rapid acting insulin" means that the insulin-like compound has an insulin action that takes affect in a very short time frame—i.e. the onset of the action is within 30 minutes and the maximum effect is within 1-3 hours.

In a preferred embodiment, the rapid acting insulin is selected from the rapid acting insulin analogues described in WO2007/074133, which is hereby incorporated by reference.

In a preferred embodiment, the rapid acting insulin is selected from the group consisting of Asp$^{B28}$ human insulin; Lys$^{B28}$Pro$^{B29}$ human insulin and Lys$^{B3}$Glu$^{B29}$ human insulin.

In a preferred embodiment, the rapid acting insulin is IAsp. IAsp is a human insulin in which the natural occurring amino acid in position B28 is replaced with Asp (Asp$^{B28}$ human insulin). IAsp is sold under the trade name of NovoRapid® (Novo Nordisk A/S).

For some embodiments the second insulin-like compound is a bolus insulin compound.

The combination of the present invention may also comprise one or more additional second insulin-like compound(s).

The one or more additional first insulin-like compound(s) may be any one or more of the second insulin-like compounds presented above.

Hydrophobicity

For some embodiments, the first insulin-like compound has an overall hydrophobicity which is essentially similar to that of human insulin.

For some embodiments, the first insulin-like compound has a hydrophobic index, $k'_{rel}$, which is in the range from about 0.02 to about 10, from about 0.1 to about 5; from about 0.5 to about 5; or from about 0.5 to about 2.

Solubility

For some embodiments, the first insulin-like compound is soluble at physiological pH values.

For some embodiments, the second insulin-like compound is soluble at physiological pH values.

When an insulin-like compound according to the invention is stated to be "soluble at physiological pH values" it means that the insulin derivative can be used for preparing injectable insulin compositions that are fully dissolved at physiological pH values. Such favourable solubility may either be due to the inherent properties of the insulin-like compound alone or a result of a favourable interaction between the insulin derivative and one or more ingredients contained in the vehicle.

Hence, in one embodiment, the invention relates to a pharmaceutical composition comprising a first insulin-like compound which is soluble at physiological pH values and/or a second insulin-like compound which is soluble at physiological pH values.

Hence, in one embodiment, the invention relates to a pharmaceutical composition comprising a first insulin-like compound which is soluble at physiological pH values and a second insulin-like compound which is soluble at physiological pH values.

In another embodiment, the invention relates to a pharmaceutical composition comprising a first insulin-like compound which is soluble at pH values in the interval from about 6.5 to about 8.5 and/or a second insulin-like compound which is soluble at pH values in the interval from about 6.5 to about 8.5.

Some Preferred Embodiments

For some embodiments of the present invention, the combination of the present invention is used in conjunction other one or more other pharmaceutically active agent(s).

For some embodiments of the present invention, the combination of the present invention is used in conjunction with one or more other antidiabetic drug(s), such as one or more orally administered antidiabetic drugs For some embodiments of the present invention, the combination of the present invention is used to treat a subject that is at least 20 years.

For some embodiments of the present invention, the combination of the present invention is used to treat a subject whose body mass index is no greater than 35 kg/m$^2$.

For some embodiments of the present invention, the combination of the present invention is used to treat a subject whose body mass index is about 25 kg/m$^2$.

For some embodiments of the present invention, the combination of the present invention is used to treat a subject whose baseline HbA$_{1c}$ level before treatment is greater than 7, such as about 8 or 9.

For some embodiments of the present invention, the combination of the present invention is used to treat a subject that has been suffering from diabetes duration for at least 1 year, such as at least 5 years, such as at least 10 years.

For some embodiments of the present invention, the combination of the present invention is capable of achieving a baseline HbA$_{1c}$ level for the subject being no more than 7 after 26 weeks of treatment.

For some embodiments of the present invention, the combination of the present invention is capable of achieving a PG (plasma glucose) increment being lowered more than with the equivalent dosage use of IGlar.

For some embodiments of the present invention, the combination of the present invention is capable of achieving a PG (plasma glucose) increment being lowered more than about 50%.

For some embodiments of the present invention, the combination of the present invention is capable of achieving a long acting basal coverage with additional prandial coverage of one daily meal.

For some embodiments of the present invention, the combination of the present invention is capable of achieving a superior control of postprandial glucose excursions compared with an equivalent dose of IGlar without compromising the FPF (fasting plasma glucose) control.

For some embodiments of the present invention, the combination of the present invention is capable of achieving an improvement in glycaemic control and lowers prandial plasma glucose increment at dinner.

For some embodiments of the present invention, the combination of the present invention is superior to IGlar at an equivalent dose in achieving a larger proportion of subjects to an HbA1c target <7% without confirmed hypoglycaemia.

For some embodiments of the present invention, with the combination of the present invention, the first insulin-like compound and the second insulin-like compound are delivered together.

For some embodiments of the present invention, with the combination of the present invention, the first insulin-like compound and the second insulin-like compound are delivered together in the same formulation.

For some embodiments of the present invention, with the combination of the present invention, the first insulin-like compound and/or the second insulin-like compound are delivered by injection.

For some embodiments of the present invention, with the combination of the present invention, the first insulin-like compound and the second insulin-like compound are delivered by injection.

For some embodiments of the present invention, with the combination of the present invention, the first insulin-like compound and the second insulin-like compound are delivered by injection together.

For some embodiments of the present invention, with the combination of the present invention, the first insulin-like compound and the second insulin-like compound are delivered by injection together and in the same formulation.

For some embodiments of the present invention, with the combination of the present invention, the first insulin-like compound and/or the second insulin-like compound are delivered by injection by use of insulin pen devices.

For some embodiments of the present invention, with the combination of the present invention, the first insulin-like compound and the second insulin-like compound are delivered by injection by use of insulin pen devices.

For some embodiments of the present invention, with the combination of the present invention, the first insulin-like compound and the second insulin-like compound are delivered by injection together by use of insulin pen devices.

For some embodiments of the present invention, with the combination of the present invention, the first insulin-like compound and the second insulin-like compound are delivered by injection together and in the same formulation by use of a insulin pen devices.

For some embodiments of the present invention, with the combination of the present invention, the first insulin-like compound and/or the second insulin-like compound are delivered by injection by use of FlexPen®(s) or FlexTouch®(s).

For some embodiments of the present invention, with the combination of the present invention, the first insulin-like compound and the second insulin-like compound are delivered by injection by use of FlexPen®(s) or FlexTouch®(s).

For some embodiments of the present invention, with the combination of the present invention, the first insulin-like compound and the second insulin-like compound are delivered by injection together by use of FlexPen®(s) or FlexTouch®(s).

For some embodiments of the present invention, with the combination of the present invention, the first insulin-like compound and the second insulin-like compound are delivered by injection together and in the same formulation by use of a FlexPen® or FlexTouch®.

FlexPen® and or FlexTouch® are trade marks of Novo Nordisk A/S.

In a preferred embodiment, the insulin derivative disclosed in WO2005/012347 (which is hereby incorporated by reference) can be formulated with rapid acting insulin analogues as described in WO2007/074133 (which is hereby incorporated by reference).

In a preferred embodiment, the first insulin-like compound is $N^{\epsilon B29}$—($N^\alpha$—(HOOC(CH$_2$)14CO)-γ-L-Glu) des(B30) human insulin and the second insulin-like compound is AspB28 human insulin, together with pharmaceutically acceptable carriers and additives.

In some instances herein, $N^{\epsilon B29}$—($N^\alpha$—(HOOC(CH$_2$)14CO)-γ-L-Glu) des(B30) human insulin is referred to as Degludec, insulin degludec, IDeg or LysB29(Nε-hexadecandioyl-γ-Glu) des(B30) human insulin.

In some instances herein, $N^{\epsilon B29}$—($N^\alpha$—(HOOC(CH$_2$)14CO)-γ-L-Glu) des(B30) human insulin and the second insulin-like compound is AspB28 human insulin is referred to as IDegAsp or DegludecPlus.

Other Combinations

In one embodiment, the combination of the present invention is used on its own in the treatment of the patient, or for the treatment of a specific condition of the patient, such as treating diabetes.

In one embodiment, the combination of the present invention is used in conjunction with one or more other combinations according to the present invention, or components thereof.

In one embodiment, the combination of the present invention is used in conjunction with one or more other pharmaceutically active agents.

In one embodiment, the combination of the present invention is used in conjunction with one or more anti-diabetic drugs.

In one embodiment, the combination of the present invention is used in conjunction with one or more orally administered anti-diabetic drugs.

In one embodiment, the combination of the present invention is used in conjunction with one or more anti-diabetic drugs, such as one or more of sulphonylurea, biguanide, alpha-glucosidase inhibitor, thiazolidinedione, DPP4 inhibitor, glinide, metforminanda GLP-1 agonist.

Formulations

The first insulin-like compound according to the present invention and the second insulin-like compound according to the present invention can if necessary be mixed in a ratio from about 90/10%; about 85/15%, about 80/20%, about 70/30%, about 60/40%, about 50/50%, about 40/60%, about 30/60% or about 10/90%.

In another embodiment, he first insulin-like compound according to the present invention and the second insulin-like compound according to the present invention can if necessary be mixed in a ratio from 40% or more of the first to 60% or less of the second insulin-like compound, from more than 50% or more of the first to less than 50% of the second insulin-like compound, or from about 70% or more of the first to about 30% or less of the second insulin-like compound, In another embodiment, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of a first insulin-like compound of the present invention and/or a second insulin-like compound.

In the combination of the present invention, each of the insulin-like compounds may be in an amount of from about 0.01 to about 5 U/Kg, typically from about 0.03 to about 3 U/Kg.

In one embodiment of the present invention the concentration of the pharmaceutical composition is 100 U/ml.

In one embodiment of the present invention the concentration of the pharmaceutical composition is 200 U/ml.

In one embodiment the naturally occurring insulin, insulin analogue or derivative is formulated together with a pharmaceutically acceptable carrier and/or vehicle and/or diluent and/or excipient.

A pharmaceutical composition containing a naturally occurring insulin, an insulin analogue, or a derivative of a naturally occurring insulin or insulin analogue is termed "an insulin composition" herein. In order to exercise the present invention an insulin composition may be administered parenterally to patients in need of such a treatment. Parenteral administration may be performed by injection, such as subcutaneous, intramuscular or intravenous injection, by means of a syringe, optionally a pen-like syringe. In one embodiment the administration is by s.c. injection. In one embodiment the administration is by i.m. injection. In one embodiment the administration is by i.v. injection. Alternatively, parenteral administration can be performed by means of an infusion pump. Further options are to administer the insulin composition nasally or pulmonally, preferably in compositions, powders or liquids, specifically designed for the purpose.

Injectable insulin compositions can be prepared using the conventional techniques of the pharmaceutical industry which involve dissolving and mixing the ingredients as appropriate to give the desired end product. Thus, according to one procedure, a natural insulin, analogue or derivative is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

The buffer is typically selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative useful in embodiments of the invention.

In a further embodiment of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19th edition, 1995.

In a further embodiment of the invention the formulation further comprises an isotonic agent which may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19th edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazine ethanesulfonic acid), TRIS (2-amino-2-hydroxymethyl-1,3-propandiol), and sodium phosphate.

A composition for nasal administration may, for example, be prepared as described in European Patent No. 272097 (to Novo Nordisk A/S).

Insulin compositions containing can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin, analogue or derivative employed, the age, body weight, physical activity, and diet of the patient, on a possible combination with other drugs, and on the severity of the state to be treated. It is recommended that the dosage regimen be determined for each individual patient by those skilled in the art in a similar way as for known insulin compositions, however taking into consideration the present teachings concerning dosage intervals.

Where expedient, the insulin compositions may be used in combination with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

In one embodiment the composition of the invention is as defined in WO 2007/074133 or WO2008/152106.

Use as a Medicament

In one embodiment the present invention is used in the disease or condition is selected from the group consisting of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation. In one embodiment the diabetes mellitus is type 1 or 2 diabetes. In one embodiment the diabetes mellitus is type 2 diabetes, which fails oral anti-diabetic treatment.

In one embodiment the present invention relates to a combination of the present invention as defined herein in the preparation of a pharmaceutical composition for treatment of diabetes mellitus or other conditions characterized by hyperglycaemia, pre-diabetes, impaired glucose tolerance, metabolic syndrome, obesity, cachexia, in vivo beta-cell loss/death, excessive appetite, and inflammation, wherein the treatment is as defined herein.

In one embodiment the invention relates to instructions for use comprising a description of a method as defined herein.

EMBODIMENTS OF THE INVENTION

Figure 1:
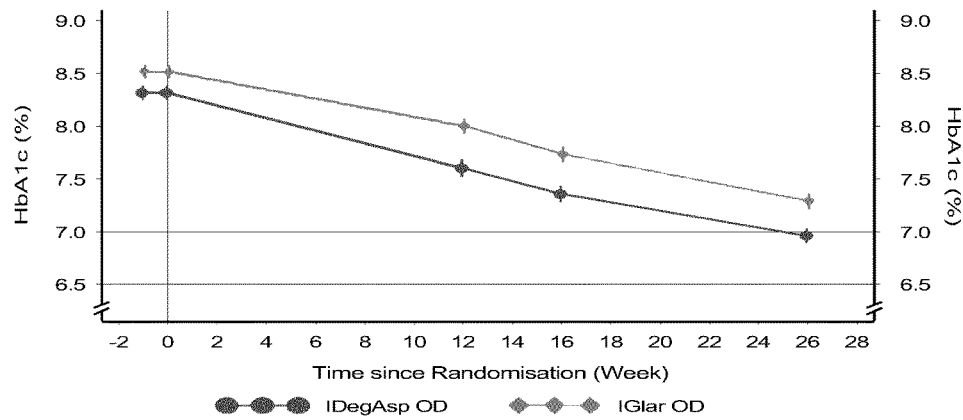
FIG. 1 shows a graph.

The invention will be further summarised in the paragraphs below:

1a. A combination comprising at least a first insulin-like compound and a second insulin-like compound for treating a condition or a disease in a subject in need thereof where administration of insulin would be of benefit to said subject; wherein said combination is administered in an amount to achieve a beneficial glycaemic control in said subject as determined by the levels of $HbA_{1c}$ in said subject after administration of said combination at the largest meal of the day for said subject; wherein said beneficial glycaemic control by said combination is superior to any glycaemic control achieved by an equivalent dose of IGlar in said subject as determined by the levels of $HbA_{1c}$ in said subject after administration of IGlar for said subject and/or wherein said beneficial glycaemic control by said combination comprises decreasing the levels of $HbA_{1c}$ in said subject to about 7 or less after administration of said combination at the largest meal of the day; wherein said first insulin-like compound is longer acting than the second insulin-like compound; and wherein said combination is administered at the largest meal of the day for said subject.

1b. A combination comprising at least a first insulin-like compound and a second insulin-like compound for treating a condition or a disease in a subject in need thereof where administration of insulin would be of benefit to said subject; wherein said combination is administered in an amount to achieve a beneficial glycaemic control in said subject as determined by the levels of $HbA_{1c}$ in said subject after administration of said combination at the largest meal of the day for said subject; wherein said beneficial glycaemic control by said combination is superior to any glycaemic control achieved by an equivalent dose of IGlar in said subject as determined by the levels of $HbA_{1c}$ in said subject after administration of IGlar for said subject and/or wherein said beneficial glycaemic control by said combination comprises decreasing the levels of $HbA_{1c}$ in said subject to about 7 or less after administration of said combination at the largest meal of the day; wherein said first insulin-like compound is longer acting than the second insulin-like compound; wherein said combination is administered at the largest meal of the day for said subject;

wherein said first insulin-like compound is at least a long acting insulin, preferably an ultra long acting insulin;

wherein said first insulin-like compound is a derivative of a naturally occurring insulin or is an insulin analogue; and wherein said first insulin-like compound has a side chain attached to the α-amino group of the N-terminal amino acid residue of the B chain or to the ε-amino group of a Lys residue present in the B chain of the parent insulin, the side chain being of the general formula (I):

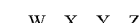

wherein W is:
an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;

a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the α-amino group of the N-terminal amino acid residue of the B chain or to the ε-amino group of a Lys residue present in the B chain of the parent insulin;

X is:
—CO—;
—COCH(COOH)C̲O—;
—CON(CH₂COOH)CH₂C̲O—;
—CON(CH₂COOH)CH₂CON(CH₂COOH)CH₂C̲O—;
—CON(CH₂CH₂COOH)CH₂CH₂C̲O—;
—CON(CH₂CH₂COOH)CH₂CH₂CON(CH₂CH₂COOH)CH₂CH₂C̲O—;
—CONHCH(COOH)(CH₂)₄NHC̲O—;
—CON(CH₂CH₂COOH)CH₂C̲O—; or
—CON(CH₂COOH)CH₂CH₂C̲O— that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

Y is:
—(CH₂)ₘ— where m is an integer in the range of 6 to 32;
a divalent hydrocarbon chain comprising 1, 2 or 3 —CH=CH— groups and a number of —CH₂— groups sufficient to give a total number of carbon atoms in the chain in the range of 10 to 32;
a divalent hydrocarbon chain of the formula —(CH₂)ᵥC₆H₄(CH₂)_w— wherein v and w are integers or one of them is zero so that the sum of v and w is in the range of 6 to 30; and Z is:
—COOH;
—CO-Asp;
—CO-Glu;
—CO-Gly;
—CO-Sar;
—CH(COOH)₂;
—N(CH₂COOH)₂;
—SO₃H; or
—PO₃H;
and any $Zn^{2+}$ complexes thereof, provided that when W is a covalent bond and X is —CO—, then Z is different from —COOH.

2a. A combination for achieving glycaemic control according to any one of the preceding paragraphs wherein the largest meal of the day is determined by said patient.

2b. A combination for achieving glycaemic control according to any one of the preceding paragraphs wherein the largest meal of the day is not necessarily dinner for said patient.

2c. A combination for achieving glycaemic control according to any one of the preceding paragraphs wherein at the largest meal comprises or consists of during said meal as well a sup to about 30 minutes before first food ingestion and up to about 30 minutes after last food ingestion of said meal.

3a. A combination for achieving glycaemic control according to any of previous paragraphs wherein said beneficial glycaemic control by said combination is superior to any glycaemic control achieved by an equivalent dose of IGlar in said subject as determined by the levels of $HbA_{1c}$ in said subject after administration of IGlar for said subject; and wherein said beneficial glycaemic control by said combination comprises decreasing the levels of $HbA_{1c}$ in said subject to about 7 or less after administration of said combination at the largest meal of the day.

3b. A combination for achieving glycaemic control according to paragraph 1a or 1b wherein said combination achieves long term glycaemic control in said subject.

4. A combination for achieving glycaemic control according to any one of the preceding paragraphs wherein the combination is capable of causing the subject to have has less nocturnal hypoglycaemia compared to an equivalent dose of IGlar.

5. A combination for achieving glycaemic control according to any one of the preceding paragraphs wherein the combination is capable of causing the subject to have less overall hypoglycaemia compared to an equivalent dose of IGlar.

6. A combination for achieving glycaemic control according to any one of the preceding paragraphs wherein said combination is administered once daily to said subject.

7. A combination for achieving glycaemic control according to any one of the preceding paragraphs wherein said subject suffers from a disease or condition selected from the group consisting of diabetes mellitus, such as type 1 diabetes or type 2 diabetes, or other conditions characterized by hyperglycaemia, pre-diabetes, impaired glucose tolerance, metabolic syndrome, obesity, cachexia, in vivo beta-cell loss/death, excessive appetite, and inflammation.

8. A combination for achieving glycaemic control according to any one of the preceding paragraphs wherein said subject suffers from type II diabetes.

9. A combination for achieving glycaemic control according to any one of the preceding paragraphs wherein said first insulin-like compound is present in said combination in an amount greater than the second insulin-like compound.

10a. A combination for achieving glycaemic control according to any one of the preceding paragraphs wherein said first insulin-like compound is present in said combination in a molar amount of more than about 55%, or more than about 60%, or more than about 65%, or more than about 70%, or more than about 75% or more than about 80% based on the molar amount of the second insulin-like compound in said combination.

10b. A combination for achieving glycaemic control according to any one of the preceding paragraphs wherein said first insulin-like compound is present in said combination in a molar amount of about 70% or more, based on the molar amount of the second insulin-like compound in said combination.

11a. A combination for achieving glycaemic control according to any one of the preceding paragraphs wherein said first insulin-like compound is present in said combination in a molar amount of about 70%, based on the molar amount of the second insulin-like compound in said combination.

11b. A combination for achieving glycaemic control according to any one of the preceding paragraphs wherein said first insulin-like compound is present in said combination in a molar amount of about 85%, based on the molar amount of the second insulin-like compound in said combination.

12a. A combination for achieving glycaemic control according to any one of the preceding paragraphs wherein said second insulin-like compound is present in said combination combination in a molar amount of less than about 55%, or less than about 40%, or less than about 35%, or less than about 30%, or less than about 25%, or less than about 20% based on the molar amount of the first insulin-like compound in said combination.

12b. A combination for achieving glycaemic control according to any one of the preceding paragraphs wherein said second insulin-like compound is present combination in a molar amount of about 30% or less, based on the molar amount of the first insulin-like compound in said combination.

12c. A combination for achieving glycaemic control according to any one of the preceding paragraphs wherein said second insulin-like compound is present combination in a molar amount of about 15%, based on the molar amount of the first insulin-like compound in said combination.

13. A combination for achieving glycaemic control according to any one of the preceding paragraphs wherein said second insulin-like compound is present combination in a molar amount of about 30%, based on the molar amount of the first insulin-like compound in said combination.

14a. A combination for achieving glycaemic control according to any one of the preceding paragraphs wherein said combination comprises a pharmaceutically acceptable carrier and/or vehicle and/or diluent and/or excipient.

14b. A combination for achieving glycaemic control according to any one of the preceding paragraphs wherein said first insulin-like compound is at least a long acting insulin.

14c. A combination for achieving glycaemic control according to any one of the preceding paragraphs wherein said first insulin-like compound is an ultra long acting insulin.

14d. A combination for achieving glycaemic control according to any one of the preceding paragraphs wherein said first insulin-like compound is a derivative of a naturally occurring insulin or is an insulin analogue.

15. A combination for achieving glycaemic control according to any one of the preceding paragraphs wherein said first insulin-like compound is selected from the group consisting of $N^{\epsilon B29}$—($N^{\alpha}$—(HOOC(CH$_2$)$_{14}$CO)-γ-Glu) des(B30) human insulin; $N^{\epsilon B29}$—($N^{\alpha}$—(HOOC(CH$_2$)$_{15}$CO)-γ-Glu) des(B30) human insulin; $N^{\epsilon B29}$—($N^{\alpha}$—(HOOC(CH$_2$)$_{16}$CO)-γ-Glu) des(B30) human insulin; $N^{\epsilon B29}$—($N^{\alpha}$—(HOOC(CH$_2$)$_{17}$CO)-γ-Glu) des(B30) human insulin; $N^{\epsilon B29}$—($N^{\alpha}$—(HOOC(CH$_2$)$_{18}$CO)-γ-Glu) des(B30) human insulin; $N^{\epsilon B29}$—($N^{\alpha}$—(HOOC(CH$_2$)$_{16}$CO)-γ-Glu-N-(γ-Glu)) des(B30) human insulin; $N^{\epsilon B29}$—($N^{\alpha}$-(Asp-OC(CH$_2$)$_{16}$CO)-γ-Glu) des(B30) human insulin; $N^{\epsilon B29}$—($N^{\alpha}$-(Glu-OC(CH$_2$)$_{14}$CO)-γ-Glu) des(B30) human insulin; $N^{\epsilon B29}$—($N^{\alpha}$-(Glu-OC(CH$_2$)$_{14}$CO—) des(B30) human insulin; $N^{\epsilon B29}$—($N^{\alpha}$-(Asp-OC(CH$_2$)$_{16}$CO—) des(B30) human insulin; $N^{\epsilon B29}$—($N^{\alpha}$—(HOOC(CH$_2$)$_{16}$CO)-α-Glu-N-(β-Asp)) des(B30) human insulin; $N^{\epsilon B29}$—($N^{\alpha}$-(Gly-OC(CH$_2$)$_{13}$CO)-γ-Glu) des(B30) human insulin; $N^{\epsilon B29}$—($N^{\alpha}$-

(Sar-OC(CH₂)₁₃CO)-γ-Glu) des(B30) human insulin; N^εB29—(N^α—(HOOC(CH₂)₁₃CO)-γ-Glu) des(B30) human insulin; N^εB29—(N^α—(HOOC(CH₂)₁₃CO)-β-Asp) des(B30) human insulin; N^εB29—(N^α—(HOOC(CH₂)₁₃CO)-α-Glu) des(B30) human insulin; N^εB29—(N^α—(HOOC(CH₂)₁₆CO)-γ-D-Glu) des(B30) human insulin; N^εB29—(N^α—(HOOC(CH₂)₁₄CO)-β-D-Asp) des(B30) human insulin; N^εB29—(N^α—(HOOC(CH₂)₁₄CO)-β-D-Asp) human insulin; N^εB29—(N—HOOC(CH₂)₁₆CO-β-D-Asp) des(B30) human insulin; N^εB29—(N—HOOC(CH₂)₁₄CO-IDA) des(B30) human insulin; N^εB29—[N—(HOOC(CH₂)₁₆CO)—N-(carboxyethyl)-Gly] des(B30) human insulin; N^εB29—[N—(HOOC(CH₂)₁₄CO)—N-(carboxyethyl)-Gly] des(B30) human insulin; and N^εB29—[N—(HOOC(CH₂)₁₄CO)—N-(carboxymethyl)-β-Ala] des(B30) human insulin.

16. A combination for achieving glycaemic control according to any one of the preceding paragraphs wherein said first insulin-like compound is LysB29(Nε-hexadecandioyl-γ-Glu) des(B30) human insulin.

17. A combination for achieving glycaemic control according to any one of the preceding paragraphs wherein said second insulin-like compound is a rapid acting insulin.

18. A combination for achieving glycaemic control according to any one of the preceding paragraphs wherein said second insulin-like compound is a derivative of a naturally occurring insulin or is an insulin analogue.

19. A combination for achieving glycaemic control according to any one of the preceding paragraphs wherein said second insulin-like compound comprises insulin wherein at least one of the amino acid residues has been substituted.

20. A combination for achieving glycaemic control according to any one of the preceding paragraphs wherein said second insulin-like compound is selected from the group consisting of Asp^B28 human insulin; Lys^B28Pro^B29 human insulin and Lys^B3Glu^B29 human insulin.

21. A combination for achieving glycaemic control according to any one of the preceding paragraphs wherein said second insulin-like compound is Asp^B28 human insulin.

22. A combination comprising at least a first insulin-like compound and a second insulin-like compound for treating a condition or a disease in a subject in need thereof where administration of insulin would be of benefit to said subject; wherein said combination is administered in an amount to achieve a beneficial glycaemic control in said subject as determined by the levels of HbA₁c in said subject after administration of said combination at the largest meal of the day for said subject; wherein said beneficial glycaemic control by said combination is superior to any glycaemic control achieved by an equivalent dose of IGlar in said subject as determined by the levels of HbA₁c in said subject after administration of IGlar for said subject and/or wherein said beneficial glycaemic control by said combination comprises decreasing the levels of HbA₁c in said subject to about 7 or less after administration of said combination at the largest meal of the day; wherein said first insulin-like compound is longer acting than the second insulin-like compound; wherein said combination is administered at the largest meal of the day for said subject;

wherein said first insulin-like compound is at least a long acting insulin, preferably an ultra long acting insulin;

wherein said first insulin-like compound is a derivative of a naturally occurring insulin or is an insulin analogue;

wherein said first insulin-like compound has a side chain attached to the α-amino group of the N-terminal amino acid residue of the B chain or to the ε-amino group of a Lys residue present in the B chain of the parent insulin, the side chain being of the general formula (I):

—W—X—Y—Z wherein W is:

an α-amino acid residue having a carboxylic acid group in the side chain which residue forms, with one of its carboxylic acid groups, an amide group together with the α-amino group of the N-terminal amino acid residue of the B chain or together with the ε-amino group of a Lys residue present in the B chain of the parent insulin;

a chain composed of two, three or four α-amino acid residues linked together via amide bonds, which chain—via an amide bond—is linked to the α-amino group of the N-terminal amino acid residue of the B chain or to the ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to the α-amino group of the N-terminal amino acid residue of the B chain or to the ε-amino group of a Lys residue present in the B chain of the parent insulin;

X is:
—CO—;
—COCH(COOH)C̲O—;
—CON(CH₂COOH)CH₂C̲O—;
—CON(CH₂COOH)CH₂CON(CH₂COOH)CH₂C̲O—;
—CON(CH₂CH₂COOH)CH₂CH₂C̲O—;
—CON(CH₂CH₂COOH)CH₂CH₂CON(CH₂CH₂COOH)CH₂CH₂C̲O—;
—CONHCH(COOH)(CH₂)₄NHC̲O—;
—CON(CH₂CH₂COOH)CH₂C̲O—; or
—CON(CH₂COOH)CH₂CH₂C̲O— that
a) when W is an amino acid residue or a chain of amino acid residues, via a bond from the underscored carbonyl carbon forms an amide bond with an amino group in W, or
b) when W is a covalent bond, via a bond from the underscored carbonyl carbon forms an amide bond with the N-terminal α-amino group in the B chain or with the ε-amino group of a Lys residue present in the B chain of the parent insulin;

Y is:
—(CH₂)ₘ— where m is an integer in the range of 6 to 32;
a divalent hydrocarbon chain comprising 1, 2 or 3 —CH=CH— groups and a number of —CH₂— groups sufficient to give a total number of carbon atoms in the chain in the range of 10 to 32;
a divalent hydrocarbon chain of the formula —(CH₂)ᵥC₆H₄(CH₂)ᵥᵥ— wherein v and w are integers or one of them is zero so that the sum of v and w is in the range of 6 to 30; and Z is:
—COOH;
—CO-Asp;
—CO-Glu;
—CO-Gly;
—CO-Sar;
—CH(COOH)₂;
—N(CH₂COOH)₂;
—SO₃H; or
—PO₃H;

and any $Zn^{2+}$ complexes thereof, provided that when W is a covalent bond and X is —CO—, then Z is different from —COOH; and wherein said second insulin-like compound is selected from the group consisting of $Asp^{B28}$ human insulin; $Lys^{B28}Pro^{B29}$ human insulin and $Lys^{B3}Glu^{B29}$ human insulin.

23. A combination for achieving glycaemic control according to paragraph 22 wherein said beneficial glycaemic control by said combination is superior to any glycaemic control achieved by an equivalent dose of IGlar in said subject as determined by the levels of $HbA_{1c}$ in said subject after administration of IGlar for said subject; and wherein said beneficial glycaemic control by said combination comprises decreasing the levels of $HbA_{1c}$ in said subject to about 7 or less after administration of said combination at the largest meal of the day.

24. A combination comprising at least a first insulin-like compound and a second insulin-like compound for treating a condition or a disease in a subject in need thereof where administration of insulin would be of benefit to said subject; wherein said combination is administered in an amount to achieve a beneficial glycaemic control in said subject as determined by the levels of $HbA_{1c}$ in said subject after administration of said combination at the largest meal of the day for said subject; wherein said beneficial glycaemic control by said combination is superior to any glycaemic control achieved by an equivalent dose of IGlar in said subject as determined by the levels of $HbA_{1c}$ in said subject after administration of IGlar for said subject and/or wherein said beneficial glycaemic control by said combination comprises decreasing the levels of $HbA_{1c}$ in said subject to about 7 or less after administration of said combination at the largest meal of the day; wherein said first insulin-like compound is longer acting than the second insulin-like compound; and wherein said combination is administered at the largest meal of the day for said subject;

wherein said first insulin-like compound is LysB29(Nε-hexadecandioyl-γ-Glu) des(B30) human insulin; and wherein said second insulin-like compound is $Asp^{B28}$ human insulin.

25. A combination for achieving glycaemic control according to paragraph 24 wherein said beneficial glycaemic control by said combination is superior to any glycaemic control achieved by an equivalent dose of IGlar in said subject as determined by the levels of $HbA_{1c}$ in said subject after administration of IGlar for said subject; and wherein said beneficial glycaemic control by said combination comprises decreasing the levels of $HbA_{1c}$ in said subject to about 7 or less after administration of said combination at the largest meal of the day.

26a. A combination comprising at least a first insulin-like compound and a second insulin-like compound for treating a condition or a disease in a subject in need thereof where administration of insulin would be of benefit to said subject; wherein said combination is administered in an amount to achieve a beneficial glycaemic control in said subject as determined by the levels of $HbA_{1c}$ in said subject after administration of said combination at the largest meal of the day for said subject; wherein said beneficial glycaemic control by said combination is superior to any glycaemic control achieved by an equivalent dose of IGlar in said subject as determined by the levels of $HbA_{1c}$ in said subject after administration of IGlar for said subject and/or wherein said beneficial glycaemic control by said combination comprises decreasing the levels of $HbA_{1c}$ in said subject to about 7 or less after administration of said combination at the largest meal of the day; wherein said first insulin-like compound is longer acting than the second insulin-like compound; and wherein said combination is administered at the largest meal of the day for said subject;

wherein said first insulin-like compound is LysB29(Nε-hexadecandioyl-γ-Glu) des(B30) human insulin;

wherein said second insulin-like compound is $Asp^{B28}$ human insulin;

wherein said first insulin-like compound is present in said combination in an amount of about 70%; and wherein said second insulin-like compound is present in said combination in an amount of about 30%.

26b. A combination comprising at least a first insulin-like compound and a second insulin-like compound for treating a condition or a disease in a subject in need thereof where administration of insulin would be of benefit to said subject; wherein said combination is administered in an amount to achieve a beneficial glycaemic control in said subject as determined by the levels of $HbA_{1c}$ in said subject after administration of said combination at the largest meal of the day for said subject; wherein said beneficial glycaemic control by said combination is superior to any glycaemic control achieved by an equivalent dose of IGlar in said subject as determined by the levels of $HbA_{1c}$ in said subject after administration of IGlar for said subject and/or wherein said beneficial glycaemic control by said combination comprises decreasing the levels of $HbA_{1c}$ in said subject to about 7 or less after administration of said combination at the largest meal of the day; wherein said first insulin-like compound is longer acting than the second insulin-like compound; and wherein said combination is administered at the largest meal of the day for said subject;

wherein said first insulin-like compound is LysB29(Nε-hexadecandioyl-γ-Glu) des(B30) human insulin;

wherein said second insulin-like compound is $Asp^{B28}$ human insulin;

wherein said first insulin-like compound is present in said combination in an amount of about wherein said first insulin-like compound is present in said combination in an amount of about 70% or more; and wherein said second insulin-like compound is present in said combination in an amount of about 30% or less.

27. A combination for achieving glycaemic control according to paragraph 26a or 26ba wherein said beneficial glycaemic control by said combination is superior to any glycaemic control achieved by an equivalent dose of IGlar in said subject as determined by the levels of $HbA_{1c}$ in said subject after administration of IGlar for said subject; and wherein said beneficial glycaemic control by said combination comprises decreasing the levels of $HbA_{1c}$ in said subject to about 7 or less after administration of said combination at the largest meal of the day.

28. A combination comprising at least a first insulin-like compound and a second insulin-like compound for treating a condition or a disease in a subject in need thereof where administration of insulin would be of benefit to said subject; wherein said combination is administered in an amount to achieve glycaemic control in said subject by decreasing the levels of HbA1c in said subject to about 7 or less after administration of said combination at the largest meal of the day for said subject; wherein said first insulin-like compound is longer acting than the second insulin-like compound.

29. A combination comprising at least a first insulin-like compound and a second insulin-like compound for treating a condition or a disease in a subject in need thereof where administration of insulin would be of benefit to said subject;

wherein said combination is administered in an amount to achieve superior glycaemic control compared to an equivalent dose of IGlar in said subject by affecting the levels of HbA1c in said subject after administration of said combination at the largest meal of the day for said subject; wherein said first insulin-like compound is longer acting than the second insulin-like compound; and wherein said combination is administered at the largest meal of the day for said subject.

30. A combination comprising at least a first insulin-like compound and a second insulin-like compound for treating a condition or a disease in a subject in need thereof where administration of insulin would be of benefit to said subject; wherein said combination is administered in an amount to achieve glycaemic control in said subject by decreasing the levels of HbA1c in said subject to about 7 or less after administration of said combination at the largest meal of the day for said subject; wherein said first insulin-like compound is longer acting than the second insulin-like compound; and wherein said combination is administered at the largest meal of the day for said subject.

31. A combination according to any of paragraphs 24 to 30 wherein the largest meal of the day is determined by said patient.

32. A combination according to any of paragraphs 24 to 30 wherein the largest meal of the day is determined by said patient and is not necessarily the evening meal.

33. A combination for achieving glycaemic control according to any one of the preceding paragraphs wherein said first insulin like compound has an insulin action for up to 24 hours.

34. A combination for achieving glycaemic control according to any one of the preceding paragraphs wherein said first insulin like compound has an insulin action for over 24 hours.

35. A combination for achieving glycaemic control according to any one of the preceding paragraphs wherein said first insulin like compound has a half-life of at least 12 hours, such as at least 12 hours and less than 24 hours, or of at least 18 hours, such as at least 24 hours, wherein the half-life may be determined as described in Clinical Example 1.

36. A combination for achieving glycaemic control according to any one of the preceding paragraphs wherein said first insulin like compound has a prolonged profile of action defined by an average time to loss of glucose control of at least 20 hours, wherein the average time to loss of glucose control may be determined as described in Clinical Example 1.

37. A combination for achieving glycaemic control according to any one of the preceding paragraphs wherein said first insulin like compound has a sufficient prolonged profile of action defined by an average time to loss of glucose control of at least 20 hours, such between 20 and 50 hours, 20 and 45 hours, 24 and 45 hours, 26 and 45 hours, 30 and 50 hours, 35 and 50 hours, at least 26 hours, more than 26 hours, more than 26 hours and up to 50 hours, more than 26 hours and up to 50 hours, at least 28 hours, between 28 and 50 hours, at least 30 hours, between 30 and 45 hours, at least 35 hours, between 35 and 45 hours, at least 38 hours, at least about 40 hours up to about 45 hours, or of about 40 hours after administration of said insulin, wherein the prolonged profiled of action maybe determined as described in Clinical Example 1 herein.

38. A combination for achieving glycaemic control according to any one of the preceding paragraphs wherein said first insulin like compound has a prolonged profile of action defined by a mean terminal half-life of at least 12 hours, at least 14 hours, at least 16 hours, at least 18 hours, at least 20 hours, at least 22 hours, at least 24 hours, between 12 and 50 hours, 14 and 50 hours, 16 and 50 hours, 18 and 50 hours, 20 and 50 hours, 22 and 50 hours, 24 and 50 hours, 12 and 40 hours, 14 and 40 hours, 16 and 40 hours, 18 and 40 hours, at least 20 hours, at least 24 hours and up to 50 hours, between 18 and 36 hours, 20 and 36 hours, 22 and 36 hours, 24 and 36 hours, 25 and 36 hours, 26 and 36 hours, wherein the mean terminal half-life may be determined as described in Clinical Example 1 herein.

39. A combination for achieving glycaemic control according to any one of the preceding paragraphs wherein said first insulin-like compound and second insulin-like compound are in the same formulation.

40. A combination for achieving glycaemic control according to any one of the preceding paragraphs wherein said beneficial glycaemic control by said combination comprises decreasing the levels of $HbA_{1c}$ in said subject to about 7 or less after administration of said combination at the largest meal of the day over a period of about 26 weeks.

50. A combination for achieving glycaemic control according to any one of the preceding paragraphs wherein said beneficial glycaemic control by said combination comprises decreasing the levels of $HbA_{1c}$ in said subject to about 7 or less after administration of said combination at the largest meal of the day over a period of less than about 26 weeks.

51. A method of treating a subject in need of same, comprising administering to said subject a combination as defined in any one of the preceding paragraphs to achieve a beneficial glycaemic control.

52. Use of a combination as defined in any one of the preceding paragraphs in the preparation of a medicament to achieve a beneficial glycaemic control in a subject.

53. A method according to paragraph 51 or a use according to paragraph 52 wherein said subject suffers from type II diabetes.

54. A combination or method or use for achieving glycaemic control according to any one of the preceding paragraphs wherein said combination is administered in an amount of about 0.4 U/kg.

Abbreviations

The following abbreviations have been used in the specification and examples:
Aad: Alpha-amino-adipic acid (homoglutamic acid)
Bzl: Bn: benzyl
DIEA: N,N-diisopropylethylamine
DMF: N,N-dimethylformamide
IDA: Iminodiacetic acid
Sar: Sarcosine (N-methyl-glycine)
tBu: tert-butyl
TSTU: O—(N-succinimidyl)-1,1,3,3-tetramethyluronium tetrafluoroborate
THF: Tetrahydrofuran
EtOAc: Ethyl acetate
DIPEA: Diisopropylethylamine
HOAt: 1-Hydroxy-7-azabenzotriazole
TEA: triethyl amine
Su: succinimidyl=2,5-dioxo-pyrrolidin-1-yl
TFA: trifluoracetic acid
DCM: dichloromethane
DMSO: dimethyl sulphoxide
TLC: Thin Layer Chromatography
RT: room temperature hGlu: homoglutamic acid
α-Asp: L-form of —HNCH(CO—)CH₂COOH
β-Asp: L-form of —HNCH(COOH)CH₂CO—
α-Glu: L-form of —HNCH(CO—)CH₂CH₂COOH
γ-Glu: L-form of —HNCH(COOH)CH₂CH₂CO—
α-hGlu: L-form of —HNCH(CO—)CH₂CH₂CH₂COOH
δ-hGlu: L-form of —HNCH(COOH)CH₂CH₂CH₂CO—
β-Ala: —NH—CH₂—CH₂—COOH
Sar: sarcosine (N-methylglycine)
Degludec: $N^{\epsilon B29}$—($N^{\alpha}$—(HOOC(CH₂)14CO)-γ-L-Glu) des(B30) human insulin
AspB28: human insulin analogue having Asp at position B28
IDegAsp: combination of $N^{\epsilon B29}$—($N^{\alpha}$—(HOOC(CH₂)14CO)-γ-L-Glu) des(B30) human insulin and AspB28
DegludecPlus: combination of $N^{\epsilon B29}$—($N^{\alpha}$—(HOOC(CH₂)14CO)-γ-L-Glu) des(B30) human insulin and AspB28
OAD: oral antidiabetic The present invention is further illustrated by the following examples which, however, are not to be construed as limiting the scope of protection.

EXAMPLES

Introduction

To investigate the clinical effect of any insulin product, a clinical trial has to be conducted under conditions representing the mode of use of the invention. Clinical trials investigating compounds for the treatment of diabetes with the purpose of obtaining approval and registration are subject to guidelines provided by regional authorities (the European guideline serves as an example: Note for Guidance on Clinical Investigations of Medicinal Products in the Treatment of diabetes Mellitus, EMEA, London, 2002).

An example of an insulin-like product with a long duration of action is LysB29(Nε-hexadecandioyl-γ-Glu) des(B30) human insulin corresponding to $N^{\epsilon B29}$—($N^{\alpha}$—(HOOC(CH₂)₁₄CO)-γ-L-Glu) des(B30) human insulin (Example 1 in WO 2005/012347). This compound is sometimes referred to as LysB29(Nε-hexadecandioyl-γ-Glu) des(B30) human insulin.

In the Examples of the present invention (Clinical Examples 4 and 5), the combination of LysB29(Nε-hexadecandioyl-γ-Glu) des(B30) human insulin and IAsp was investigated with respect to the clinical effect with administration at different meal times.

We have surprisingly found that a beneficial glycaemic control (as defined herein) can be achieved by administering the combination of the present invention at the same time or around the time of the largest meal, typically from a short while before, such as about 30 minutes before, or up to a short while afterwards, such as about 30 minutes afterwards.

Preparative Examples 1 to 37 are derived from EP2275439 and are presented for information purposes as they provide background information concerning the present invention.

Clinical Examples 1 to 4 are derived from PCT/EP2011/068870 and are presented for information purposes as they provide background information concerning the present invention.

In the Pharmacological Studies Examples we present assays (I), (II) and (III). These assays are useful for determining properties about insulin-like compounds. Results are presented for some insulin-like compounds that are suitable for use as the first insulin-like compounds in the combination of the present invention.

In the Hydrophobicity Studies Example we present hydrophobicity data for some insulin-like compounds that are suitable for use as the first insulin-like compounds in the combination of the present invention.

PREPARATIVE EXAMPLES

Preparative Example 1

Synthesis of $N^{\epsilon B29}$—($N^{\alpha}$—(HOOC(CH₂)₁₄CO)-γ-Glu) des(B30) Human Insulin A preparation method of this compound is described in example 1 of the patent application WO2005/012347, which is incorporated herein by reference.

Preparative Example 2

Synthesis of NεB29-(Nα—(HOOC(CH2)16CO)-γ-Glu) des(B30) Human Insulin

A preparation method of this compound is described in example 2 of the patent application WO2005/012347, which is incorporated herein by reference.

Preparative Example 3

Synthesis of $N^{\epsilon B29}$—($N^{\alpha}$—(HOOC(CH₂)₁₆CO)-γ-Glu-N-(γ-Glu)) des(B30) Human Insulin A preparation method of this compound is described in example 3 of the patent application WO2005/012347, which is incorporated herein by reference.

Preparative Example 4

Synthesis of $N^{\epsilon B29}$—($N^{\alpha}$—(HOOC(CH₂)₁₄CO)-γ-L-Glu) des(B30) Human Insulin A preparation method of this compound is described in example 4 of the patent application WO2005/012347, which is incorporated herein by reference.

Preparative Example 5

Synthesis of $N^{\epsilon B29}$—($N^{\alpha}$—(HOOC(CH₂)₁₆CO)-γ-L-Glu) des(B30) Human Insulin A preparation method of this compound is described in example 5 of the patent application WO2005/012347, which is incorporated herein by reference.

Preparative Example 6

Synthesis of $N^{\epsilon B29}$—(N-(L-Asp-OC(CH₂)₁₆CO)-γ-L-Glu) des(B30) Human Insulin A preparation method of this compound is described in example 6 of the patent application WO2005/012347, which is incorporated herein by reference.

Preparative Example 7

Synthesis of $N^{\epsilon B29}$—(N-(L-Glu-OC(CH$_2$)$_{14}$CO-γ-L-Glu) des(B30) Human Insulin O456

A preparation method of this compound is described in example 7 of the patent application WO2005/012347, which is incorporated herein by reference.

Preparative Example 8

Synthesis of $N^{\epsilon B29}$—(N-(L-Glu-OC(CH$_2$)$_{14}$CO—) des(B30) Human Insulin A preparation method of this compound is described in example 8 of the patent application WO2005/012347, which is incorporated herein by reference.

Preparative Example 9

Synthesis of $N^{\epsilon B29}$—(N—HOOC(CH$_2$)$_{16}$CO-α-L-Glu)-N-(β-L-Asp) des(B30) Human Insulin A preparation method of this compound is described in example 9 of the patent application WO2005/012347, which is incorporated herein by reference.

Preparative Example 10

Synthesis of $N^{\epsilon B29}$—(N—HOOC(CH$_2$)$_{15}$CO-γ-L-Glu) des(B30) Human Insulin A preparation method of this compound is described in example 10 of the patent application WO2005/012347, which is incorporated herein by reference.

Preparative Example 11

Synthesis of $N^{\epsilon B29}$—(N-(Gly-OC(CH$_2$)$_{13}$CO-γ-L-Glu) des(B30) Human Insulin A preparation method of this compound is described in example 11 of the patent application WO2005/012347, which is incorporated herein by reference.

Preparative Example 12

Synthesis of $N^{\epsilon B29}$—(N-(L-Sar-OC(CH$_2$)$_{13}$CO-γ-L-Glu) des(B30) Human Insulin A preparation method of this compound is described in example 12 of the patent application WO2005/012347, which is incorporated herein by reference.

Preparative Example 13

Synthesis of $N^{\epsilon B29}$—(N—HOOC(CH$_2$)$_{16}$CO-α-L-Asp)-N-(β-L-Asp) des(B30) Human Insulin A preparation method of this compound is described in example 13 of the patent application WO2005/012347, which is incorporated herein by reference.

Preparative Example 14

Synthesis of $N^{\epsilon B29}$—(N-(Gly-OC(CH$_2$)$_{14}$CO-γ-L-Glu) des(B30) Human Insulin A preparation method of this compound is described in example 14 of the patent application WO2005/012347, which is incorporated herein by reference.

Preparative Example 15

Synthesis of $N^{\epsilon B29}$—(N—HOOC(CH$_2$)$_{14}$CO-β-L-Asp) des(B30) Human Insulin A preparation method of this compound is described in example 15 of the patent application WO2005/012347, which is incorporated herein by reference.

Preparative Example 16

Synthesis of $N^{\epsilon B29}$—(N—HOOC(CH$_2$)$_{16}$CO-β-L-Asp) des(B30) Human Insulin A preparation method of this compound is described in example 16 of the patent application WO2005/012347, which is incorporated herein by reference.

Preparative Example 17

Synthesis of $N^{\epsilon B29}$—(N-(Gly-OC(CH$_2$)$_{16}$CO-γ-L-Glu) des(B30) Human Insulin A preparation method of this compound is described in example 17 of the patent application WO2005/012347, which is incorporated herein by reference.

Preparative Example 18

Synthesis of $N^{\epsilon B29}$—(N—(HOOC(CH$_2$)$_{14}$CO-ε-L-LysCO—) des(B30) Human Insulin A preparation method of this compound is described in example 18 of the patent application WO2005/012347, which is incorporated herein by reference.

Preparative Example 19

Synthesis of $N^{\epsilon B29}$—(N—HOOC(CH$_2$)$_{16}$CO-α-L-Glu) des(B30) Human Insulin A preparation method of this compound is described in example 19 of the patent application WO2005/012347, which is incorporated herein by reference.

Preparative Example 20

Synthesis of $N^{\epsilon B29}$—(N—HOOC(CH$_2$)$_{16}$CO-α-L-Asp) des(B30) Human Insulin A preparation method of this compound is described in example 20 of the patent application WO2005/012347, which is incorporated herein by reference.

Preparative Example 21

Synthesis of $N^{\epsilon B29}$—(N—HOOC(CH$_2$)$_{15}$CO-β-L-Asp) des(B30) Human Insulin A preparation method of this compound is described in example 21 of the patent application WO2005/012347, which is incorporated herein by reference.

Preparative Example 22

Synthesis of $N^{\epsilon B29}$—(N—HOOC(CH$_2$)$_{16}$CO-γ-D-Glu) des(B30) Human Insulin A preparation method of this compound is described in example 22 of the patent application WO2005/012347, which is incorporated herein by reference.

Preparative Example 23

Synthesis of $N^{\epsilon B29}$—(N—HOOC(CH$_2$)$_{16}$CO-δ-L-Aad) des(B30) Human Insulin A preparation method of this compound is described in example 23 of the patent application WO2005/012347, which is incorporated herein by reference.

Preparative Example 24

Synthesis of $N^{\epsilon B29}$—(N—HOOC(CH$_2$)$_{13}$CO-β-L-Asp) des(B30) Human Insulin A preparation method of this compound is described in example 24 of the patent application WO2005/012347, which is incorporated herein by reference.

Preparative Example 25

Synthesis of $N^{\epsilon B29}$—(N—HOOC(CH$_2$)$_{13}$CO-β-L-Glu) des(B30) Human Insulin A preparation method of this compound is described in example 25 of the patent application WO2005/012347, which is incorporated herein by reference.

Preparative Example 26

Synthesis of $N^{\epsilon B29}$—(N—HOOC(CH$_2$)$_{14}$CO-β-D-Asp) des(B30) Human Insulin A preparation method of this compound is described in example 26 of the patent application WO2005/012347, which is incorporated herein by reference.

Preparative Example 27

Synthesis of $N^{\epsilon B29}$—(N—HOOC(CH$_2$)$_{16}$CO-β-D-Asp) des(B30) Human Insulin A preparation method of this compound is described in example 27 of the patent application WO2005/012347, which is incorporated herein by reference.

Preparative Example 28

Synthesis of $N^{\epsilon B29}$—(N—HOOC(CH$_2$)$_{14}$CO-IDA) des(B30) Human Insulin A preparation method of this compound is described in example 28 of the patent application WO2005/012347, which is incorporated herein by reference.

Preparative Example 29

Synthesis of $N^{\epsilon B29}$—[N—(HOOC(CH$_2$)$_{16}$CO)—N-(carboxymethyl)-β-Ala] des(B30) Human Insulin A preparation method of this compound is described in example 29 of the patent application WO2005/012347, which is incorporated herein by reference.

Preparative Example 30

Synthesis of $N^{\epsilon B29}$—[N—(HOOC(CH$_2$)$_{16}$CO)—N-(2-carboxyethyl)-Gly] des(B30) Human Insulin A preparation method of this compound is described in example 30 of the patent application WO2005/012347, which is incorporated herein by reference.

Preparative Example 31

Synthesis of $N^{\epsilon B29}$—[N—(HOOC(CH$_2$)$_{14}$CO)—N-(carboxyethyl)-Gly] des(B30) Human Insulin A preparation method of this compound is described in example 31 of the patent application WO2005/012347, which is incorporated herein by reference.

Preparative Example 32

Synthesis of $N^{\epsilon B29}$—[N—(HOOC(CH$_2$)$_{14}$CO)—N-(carboxymethyl)-β-Ala] des(B30) Human Insulin A preparation method of this compound is described in example 32 of the patent application WO2005/012347, which is incorporated herein by reference.

Preparative Example 33

Synthesis of $N^{\epsilon B29}$—[$N^{\alpha}$—(HOOC(CH$_2$)$_{11}$)NHCO(CH$_2$)$_3$CO)-γ-L-Glu] des(B30) Human Insulin A preparation method of this compound is described in example 33 of the patent application WO2005/012347, which is incorporated herein by reference.

Preparative Example 34

Synthesis of $N^{\epsilon B29}$—[$N^{\alpha}$—(HOOC(CH$_2$)$_{11}$)NHCO(CH$_2$)$_2$CO)-γ-L-Glu] des(B30) Human Insulin A preparation method of this compound is described in example 34 of the patent application WO2005/012347, which is incorporated herein by reference.

Preparative Example 35

Synthesis of $N^{\epsilon B29}$—[$N^{\alpha}$—(HOOC(CH$_2$)$_{16}$CO)]-Gly-γ-L-Glu des(B30) Human Insulin A preparation method of this compound is described in example 35 of the patent application WO2005/012347, which is incorporated herein by reference.

Preparative Example 36

Synthesis of $N^{\epsilon B29}$—[N—(HOOC(CH$_2$)$_{14}$CO)—N-(2-carboxyethyl)-β-Ala] des B30 Human Insulin A preparation method of this compound is described in example 36 of the patent application WO2005/012347, which is incorporated herein by reference.

Preparative Example 37

Synthesis of $N^{\epsilon B29}$—[N—(HOOC(CH$_2$)$_{16}$CO)—N-(2-carboxyethyl)-β-Ala] des B30 Human Insulin A preparation method of this compound is described in example 37 of the patent application WO2005/012347, which is incorporated herein by reference.

Pharmacological Studies

Assay (I)

Insulin Receptor Binding of the Insulin Derivatives of the Invention

The affinity of the insulin-like compounds for use in the present invention for the human insulin receptor was determined by a SPA assay (Scintillation Proximity Assay) microtiter plate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 μl of a 1:5000 diluted purified recombinant human insulin receptor—exon 11, an amount of a stock solution of A14 Tyr[$^{125}$I]-human insulin corresponding to 5000 cpm per 100 μl of reagent mix, 12 μl of a 1:1000 dilution of F12 antibody, 3 ml of SPA-beads and binding buffer to a total of 12 ml. A total of 100 μl was then added and a dilution series is made from appropriate samples. To the dilution series was then added 100 μl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

Preparation of Monoclonal mIR Antibodies

Specific antibodies (F12) were produced by monoclonal technique: RBF mice were immunized by injecting 50 μg of purified mIR in FCA subcutaneously followed by two injections with 20 μg of mIR in FIA. High responder mice were boosted intravenously with 25 μg of mIR and the spleens were harvested after 3 days. Spleen cells were fused with the myeloma Fox cell line (Köhler, G & Milstein C. (1976), European J. Immunology, 6:511-19; Taggart R T et al (1983), Science 219:1228-30). Supernatants were screened for antibody production in a mIR specific ELISA. Positive wells were cloned and tested in Western blotting.

TABLE 1

| Product | Receptor binding (% of human insulin) |
|---|---|
| Human insulin | 100 |
| $N^{\epsilon B29}$—(N—HOOC(CH$_2$)$_{14}$CO-γ-Glu) des(B30) human insulin | 26 |
| $N^{\epsilon B29}$—(N—HOOC(CH$_2$)$_{16}$CO-γ-Glu) des(B30) human insulin | 9.2 |
| $N^{\epsilon B29}$—(N—HOOC(CH$_2$)$_{16}$CO-γ-Glu-N-(γ-Glu) des(B30) human insulin | 11 |
| $N^{\epsilon B29}$—(N-(Asp-OC(CH$_2$)$_{16}$CO)-γ-Glu) des(B30) human insulin | 13 |
| $N^{\epsilon B29}$—(N-(Glu-OC(CH$_2$)$_{14}$CO-γ-Glu) des(B30) human insulin | 13 |
| $N^{\epsilon B29}$—(N-(Glu-OC(CH$_2$)$_{14}$CO—) des(B30) human insulin | 9.4 |
| $N^{\epsilon B29}$—(N—HOOC(CH$_2$)$_{16}$CO-α-Glu)-N-(β-Asp) des(B30) human insulin | 11 |
| $N^{\epsilon B29}$—(N-(Gly-OC(CH$_2$)$_{13}$CO-γ-Glu) des(B30) human insulin | 22 |
| $N^{\epsilon B29}$—(N-(Sar-OC(CH$_2$)$_{13}$CO-γ-Glu) des(B30) human insulin | 20 |
| $N^{\epsilon B29}$—(N—HOOC(CH$_2$)$_{16}$CO-α-L-Asp)-N-(β-L-Asp) des(B30) human insulin | 14 |
| $N^{\epsilon B29}$—(N-(Gly-OC(CH$_2$)$_{14}$CO-γ-Glu) des(B30) human insulin | 32 |
| $N^{\epsilon B29}$—(N—HOOC(CH$_2$)$_{15}$CO-γ-L-Glu) des(B30) human insulin | 4 |
| $N^{\epsilon B29}$—(N—HOOC(CH$_2$)$_{14}$CO-β-L-Asp) des(B30) human insulin | 16 |
| $N^{\epsilon B29}$—(N—HOOC(CH$_2$)$_{14}$CO-β-D-Asp) des(B30) human insulin | 37 |
| $N^{\epsilon B29}$—(N—HOOC(CH$_2$)$_{13}$CO-β-L-Glu) des(B30) human insulin | 15 |
| $N^{\epsilon B29}$—(N—HOOC(CH$_2$)$_{13}$CO-β-L-Asp) des(B30) human insulin | 11 |
| $N^{\epsilon B29}$—(N—HOOC(CH$_2$)$_{16}$CO-δ-L-Aad) des(B30) human insulin | 7 |
| $N^{\epsilon B29}$—(N—HOOC(CH$_2$)$_{16}$CO-γ-D-Glu) des(B30) human insulin | 13 |
| $N^{\epsilon B29}$—(N—HOOC(CH$_2$)$_{15}$CO-β-L-Asp) des(B30) human insulin | 5.4 |
| $N^{\epsilon B29}$—(N—HOOC(CH$_2$)$_{16}$CO-α-L-Asp) des(B30) human insulin | 13 |
| $N^{\epsilon B29}$—(N—HOOC(CH$_2$)$_{16}$CO-α-L-Glu) des(B30) human insulin | 16 |
| $N^{\epsilon B29}$—(N—(HOOC(CH$_2$)$_{14}$CO-ε-L-LysCO—) des(B30) human insulin | 5.7 |
| $N^{\epsilon B29}$—(N—HOOC(CH$_2$)$_{16}$CO-β-L-Asp) des(B30) human insulin | 11 |
| $N^{\epsilon B29}$—(N-(Gly-OC(CH$_2$)$_{16}$CO-γ-L-Glu) des(B30) human insulin | 9.1 |
| $N^{\epsilon B29}$—[N—(HOOC(CH$_2$)$_{16}$CO)—N-(carboxymethyl)-β-Ala] des(B30) human insulin | 9.4 |
| $N^{\epsilon B29}$—[$N^{\alpha}$—(HOOC(CH$_2$)$_{11}$)NHCO(CH$_2$)$_3$CO)-γ-L-Glu] des(B30) human insulin | 46 |

Assay (II)

Potency of the Insulin Derivatives of the Invention Relative to Human Insulin

Sprague Dawley male rats weighing 238-383 g on the experimental day were used for the clamp experiment. The rats had free access to feed under controlled ambient conditions and were fasted overnight (from 3 pm) prior to the clamp experiment.

Experimental Protocol

The rats were acclimatized in the animal facilities for at least 1 week prior to the surgical procedure. Approximately 1 week prior to the clamp experiment Tygon catheters were inserted under halothane anaesthesia into the jugular vein (for infusion) and the carotid artery (for blood sampling) and exteriorised and fixed on the back of the neck. The rats were given Streptocilin vet. (Boehringer Ingelheim; 0.15 ml/rat, i.m.) post-surgically and placed in an animal care unit (25°

C.) during the recovery period. In order to obtain analgesia, Anorphin (0.06 mg/rat, s.c.) was administered during anaesthesia and Rimadyl (1.5 mg/kg, s.c.) was administered after full recovery from the anaesthesia (2-3 h) and again once daily for 2 days.

The clamp technique employed was adapted from (1). At 7 am on the experimental day overnight fasted (from 3 pm the previous day) rats were weighed and connected to the sampling syringes and infusion system (Harvard 22 Basic pumps, Harvard, and Perfectum Hypodermic glass syringe, Aldrich) and then placed into individual clamp cages where they rested for ca. 45 min before start of experiment. The rats were able to move freely on their usual bedding during the entire experiment and had free access to drinking water. After a 30 min basal period during which plasma glucose levels were measured at 10 min intervals, the insulin derivative to be tested and human insulin (one dose level per rat, n=6-7 per dose level) were infused (i.v.) at a constant rate for 300 min. Plasma glucose levels were measured at 10 min intervals throughout and infusion of 20% aqueous glucose was adjusted accordingly in order to maintain euglyceamia. Samples of re-suspended erythrocytes were pooled from each rat and returned in about ½ ml volumes via the carotid catheter.

On each experimental day, samples of the solutions of the individual insulin derivatives to be tested and the human insulin solution were taken before and at the end of the clamp experiments and the concentrations of the peptides were confirmed by HPLC. Plasma concentrations of rat insulin and C-peptide as well as of the insulin derivative to be tested and human insulin were measured at relevant time points before and at the end of the studies. Rats were killed at the end of experiment using a pentobarbital overdose.

Test compounds and doses: Insulin-like compounds for use in the present invention to be tested were diluted from a stock solution containing 97 μM of the insulin derivative in 5 mM phosphate pH 7.7. The final concentration in the solution ready for use was 0.45 μM of the insulin derivative, 5 mM of phosphate, 100 mM of sodium chloride, 0.007% of polysorbate 20. The pH was 7.7 and the i.v. infusion rate was 15 and 20 pmol·min$^{-1}$ kg$^{-1}$.

A stock solution of human insulin that was used as reference compound was formulated in a similar medium and infused i.v. at 6, 15 or 30 pmol·min$^{-1}$ kg$^{-1}$.

Both stock solutions were stored at −20° C. and thawed overnight at 4° C. before use. The solutions were gently turned upside down several times 15 min before they were transferred to the infusion syringes.

Assay (III)

Determination in Pigs of $T_{50\%}$ of the Insulin Derivatives of the Invention $T_{50\%}$ is the time when 50% of an injected amount of the A14 Tyr[$^{125}$I] labelled derivative of an insulin-like compound for use in the present invention to be tested has disappeared from the injection site as measured with an external γ-counter.

The principles of laboratory animal care were followed, Specific pathogen-free LYYD, non-diabetic female pigs, cross-breed of Danish Landrace, Yorkshire and Duroc, were used (Holmenlund, Haarloev, Denmark) for pharmacokinetic and pharmacodynamic studies. The pigs were conscious, 4-5 months of age and weighing 70-95 kg. The animals were fasted overnight for 18 h before the experiment.

Formulated preparations of insulin-like compounds for use in the present invention labelled in Tyr$^{A14}$ with $^{125}$I were injected sc. in pigs as previously described (Ribel, U., Jørgensen, K, Brange, J, and Henriksen, U. The pig as a model for subcutaneous insulin absorption in man. Serrano-Rios, M and Lefèbvre, P. J. 891-896. 1985. Amsterdam; New York; Oxford, Elsevier Science Publishers. 1985 (Conference Proceeding)).

At the beginning of the experiments a dose of 60 nmol of the insulin-like compounds for use in the present invention (test compound) and a dose of 60 nmol of insulin detemir (both $^{125}$I labelled in Tyr A14) were injected at two separate sites in the neck of each pig.

The disappearance of the radioactive label from the site of sc. injection was monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it was possible to measure continuously the disappearance of radioactivity from a subcutaneous depot for several days using cordless portable device (Scancys Laboratorieteknik, Værløse, DK-3500, Denmark). The measurements were performed at 1-min intervals, and the counted values were corrected for background activity.

In Table 3, the column "test/detemir" shows the $T_{50\%}$ found for each of the compounds tested ("test") and the $T_{50\%}$ found for insulin detemir ("detemir") in the same experiment.

TABLE 2

| Insulin derivative | Potency relative to human insulin |
| --- | --- |
| 0454 N$^{εB29}$—(N—HOOC(CH$_2$)$_{14}$CO-γ-Glu) des(B30) human insulin | >50% |
| 0456 N$^{εB29}$—(N—HOOC(CH$_2$)$_{16}$CO-γ-Glu) des(B30) human insulin | >50% |
| 0459 N$^{εB29}$—(N—HOOC(CH$_2$)$_{16}$CO-γ-Glu-N-(γ-Glu) des(B30) human insulin | >50% |
| 0467 N$^{εB29}$—(N—HOOC(CH$_2$)$_{14}$CO-β-L-Asp) des(B30) human insulin | >50% |
| 0471 N$^{εB29}$—(N-(Gly-OC(CH$_2$)$_{14}$CO-γ-Glu) des(B30) human insulin | >50% |
| 0477 N$^{εB29}$—(N—HOOC(CH$_2$)$_{14}$CO-β-L-Asp) des(B30) human insulin | >50% |

TABLE 3

| Insulin derivative | $T_{50\%}$, hours test/detemir |
| --- | --- |
| 0454 N$^{εB29}$—(N—HOOC(CH$_2$)$_{14}$CO-γ-Glu) des(B30) human insulin | 9.0/9.5 |
| 0456 N$^{εB29}$—(N—HOOC(CH$_2$)$_{16}$CO- γ-Glu) des(B30) human insulin | 10.6/9.7 |
| 0459 N$^{εB29}$—(N—HOOC(CH$_2$)$_{16}$CO-γ-Glu-N-(γ-Glu) des(B30) human insulin | 7.8/7.4 |
| 0460 N$^{εB29}$—(N-(Asp-OC(CH$_2$)$_{16}$CO)-γ-Glu) des(B30) human insulin | 3.5/7.4 |
| 0463 N$^{εB29}$—(N-(Asp-OC(CH$_2$)$_{16}$CO—) des(B30) human insulin | 4.1/7.4 |
| 0466 N$^{εB29}$—(N—HOOC(CH$_2$)$_{16}$CO-α-Glu)-N-(β-Asp) des(B30) human insulin | 8.7/9.1 |

Hydrophobicity Studies

Hydrophobicity Data on Insulin-Like Compounds of the Invention.

The hydrophobicity (hydrophobic index) of the insulin-like compounds relative to human insulin, $k'_{rel}$, was measured on a LiChrosorb RP18 (5 µm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least $2t_0$ by varying the ratio between the A and B solutions. $k'_{rel}=(t_{derivative}-t_0)/(t_{human}-t_0)$. $k'_{rel}$ found for a number of insulin derivatives according to the invention are given in Table 4.

TABLE 4

| Insulin derivative | $k'_{rel}$ |
|---|---|
| 0454 $N^{\epsilon B29}$—(N—HOOC(CH$_2$)$_{14}$CO-γ-Glu) des(B30) human insulin | 0.87 |
| 0456 $N^{\epsilon B29}$—(N—HOOC(CH$_2$)$_{16}$CO-γ-Glu) des(B30) human insulin | 1.15 |
| 0458 $N^{\epsilon B29}$—(N—HOOC(CH$_2$)$_8$CO-γ-Glu) des(B30) human insulin | 0.45 |
| 0459 $N^{\epsilon B29}$—(N—HOOC(CH$_2$)$_{16}$CO-γ-Glu-N-(γ-Glu) des(B30) human insulin | 1.17 |
| 0460 $N^{\epsilon B29}$—(N-(Asp-OC(CH$_2$)$_{16}$CO)-γ-Glu) des(B30) human insulin | 0.70 |
| 0461 $N^{\epsilon B29}$—(N-(Glu-OC(CH$_2$)$_{14}$CO-γ-Glu) des(B30) human insulin | 0.33 |
| 0462 $N^{\epsilon B29}$—(N-(Glu-OC(CH$_2$)$_{14}$CO—) des(B30) human insulin | 1.17 |
| 0466 $N^{\epsilon B29}$—(N—HOOC(CH$_2$)$_{16}$CO-α-Glu)-N-(β-Asp) des(B30) human insulin | 1.11 |
| 0468 $N^{\epsilon B29}$—(N-(Gly-OC(CH$_2$)$_{13}$CO-γ-Glu) des(B30) insulin | 0.58 |
| 0469 $N^{\epsilon B29}$—(N-(Sar-OC(CH$_2$)$_{13}$CO-γ-Glu) des(B30) insulin | 0.63 |
| 0470 $N^{\epsilon B29}$—(N—HOOC(CH$_2$)$_{16}$CO-α-Glu)-N-(AspAsp) des(B30) human insulin | 1.07 |
| 0471 $N^{\epsilon B29}$—(N-(Gly-OC(CH$_2$)$_{14}$CO-γ-Glu) des(B30) human insulin | 0.88 |
| 0467 $N^{\epsilon B29}$—(N—HOOC(CH$_2$)$_{15}$CO-γ-L-Glu) des(B30) human insulin | 1.13 |
| 0477 $N^{\epsilon B29}$—(N—HOOC(CH$_2$)$_{14}$CO-β-L-Asp) des(B30) human insulin | 0.69 |
| 0449 $N^{\epsilon B29}$—(N—HOOC(CH$_2$)$_{13}$CO-β-L-Glu) des(B30) human insulin | 0.54 |
| 0517 $N^{\epsilon B29}$—(N—HOOC(CH$_2$)$_{13}$CO-β-L-Asp) des(B30) human insulin | 0.47 |
| 0516 $N^{\epsilon B29}$—(N—HOOC(CH$_2$)$_{16}$CO-δ-L-Aad) des(B30) human insulin | 0.84 |
| 0501 $N^{\epsilon B29}$—(N—HOOC(CH$_2$)$_{16}$CO-γ-D-Glu) des(B30) human insulin | 1.4 |
| 0492 $N^{\epsilon B29}$—(N—HOOC(CH$_2$)$_{15}$CO-β-L-Asp) des(B30) human insulin | 1.09 |
| 0489 $N^{\epsilon B29}$—(N—HOOC(CH$_2$)$_{16}$CO-α-L-Asp) des(B30) human insulin | 1.49 |
| 0487 $N^{\epsilon B29}$—(N—HOOC(CH$_2$)$_{16}$CO-α-L-Glu) des(B30) human insulin | 1.51 |
| 0483 $N^{\epsilon B29}$—(N-(HOOC(CH$_2$)$_{14}$CO-ε-L-LysCO—) des(B30) human insulin | 0.90 |
| 0481 $N^{\epsilon B29}$—(N—HOOC(CH$_2$)$_{16}$CO-β-L-Asp) des(B30) human insulin | 1.54 |
| 0482 $N^{\epsilon B29}$—(N-(Gly-OC(CH$_2$)$_{16}$CO-γ-L-Glu) des(B30) insulin | 1.57 |
| 0511 $N^{\epsilon B29}$—[N—(HOOC(CH$_2$)$_{16}$CO)—N-(carboxymethyl)-β-Ala] des(B30) human insulin | 1.13 |
| 0478 $N^{\epsilon B29}$—[N$^\alpha$—(HOOC(CH$_2$)$_{11}$)NHCO(CH$_2$)$_3$CO)-γ-L-Glu] des(B30) human insulin | 0.42 |

Clinical Studies—Clinical Examples 1-4

Clinical Example 1

Steady State Clamp—Investigating Activity Profile and Duration of Action of LysB29(Nε-hexadecandioyl-γ-Glu) des(B30) Human Insulin.

Methodology

The investigation was performed as a randomised, double-blind, single centre, two-period cross over trial to compare the activity profiles of LysB29(Nε-hexadecandioyl-γ-Glu) des(B30) human insulin and insulin glargine (IGlar) in subjects with type 1 diabetes.

Subjects were randomised to different sequences of subcutaneous (s.c.) multiple-dose once daily administration of LysB29(Nε-hexadecandioyl-γ-Glu) des(B30) human insulin and IGlar. The doses were either 0.57 U/kg or 0.85 U/kg of LysB29(Nε-hexadecandioyl-γ-Glu) des(B30) human insulin and 0.4 U/kg or 0.6 U/kg IGlar. The subjects were treated for 8 days for each dosing period. There was a washout period lasting 10-20 days between the two dosing periods.

At the last day of each dosing period subjects received a controlled intravenous infusion of glucose and human soluble insulin (Actrapid®) for 8-4 hours prior to trial drug administration in order to keep the blood glucose concentration stable at a level of 100 mg/dL (5.5 mmol/L), i.e. an euglycaemic clamp with a target blood glucose level of 100 mg/dL (5.5 mmol/L) was initiated. The euglycaemic clamp was terminated at 42 hours post-dosing but earlier if blood glucose levels increased to concentrations above 200 mg/dL (11.1 mmol/L) with no glucose infusion during the last 30 min.

Blood samples for measurement of serum LysB29(Nε-hexadecandioyl-γ-Glu) des(B30) human insulin/plasma IGlar, and blood glucose were drawn before dosing and for up to 146 hours after dosing.

Standard safety assessments were performed.

Number of Subjects 21 subjects completed the trial.

Diagnosis and Main Criteria for Inclusion

Male or female subjects with type 1 diabetes (≥12 months) aged 18-69 years (inclusive), with glycosylated haemoglobin (HbA$_{1c}$)≤10% and normally treated with insulin (≤1.2 U/kg/day). Subjects should have been treated with insulin ≥12 months and have a body mass index (BMI) of 18-28 kg/m$^2$ (inclusive) and a fasting C-peptide <0.3 nmol/L.

Test Product, Dose and Mode of Administration

Multiple doses of 0.57 U/kg or 0.85 U/kg of LysB29(Nε-hexadecandioyl-γ-Glu) des(B30) human insulin, 600 nmol/ml, LysB29(Nε-hexadecandioyl-γ-Glu) des(B30) human insulin, delivered in 3 ml FlexPen® (100 DU/ml) cartridge using NovoFine® 30G, 8 mm needles.

Duration of Treatment

Multiple doses of LysB29(Nε-hexadecandioyl-γ-Glu) des(B30) human insulin and IGlar were administered using during two different dosing periods lasting 8 days (optionally +1-5 days) at intervals of 10-20 days.

Reference Therapy, Dose and Mode of Administration

Multiple doses (0.4 U/Ig or 0.6 U/kg) of IGlar (Lantus®), 100 IU/mL, 600 nmol/mL delivered in 3.0 mL 3 mL Optiset® cartridges and injected s.c. in the thigh using PenFine® 31G, 8 mm.

Criteria for Evaluation—Efficacy

Pharmacodynamics:

Glucose infusion rate (GIR) during a euglycaemic clamp for 42 hours during the 8$^{th}$ and last dosing day.

Blood glucose concentrations.

Pharmacokinetics:
Serum LysB29(Nε-hexadecandioyl-γ-Glu) des(B30) human insulin/plasma IGlar concentrations for 144 hours following a single dose of either LysB29(Nε-hexadecandioyl-γ-Glu) des(B30) human insulin or IGlar.

Primary Endpoint:
AUCGIR(0-24 h), the area under the curve (AUC) of the GIR curve from 0 to 24 hours Key Secondary Endpoints:
Blood glucose level during euglycaemic clamp period
Pharmacokinetics (tmax, terminal half-life)

Demography of Trial Population
The 35 male and 7 female subjects with type 1 diabetes were aged 40 years on average, respectively, mean weight was 75 kg, mean HbA1c was 7.8%, and they had a mean diabetes duration of 21 years.

Key Results
The AUCGIR(0-24 h) for LysB29(Nε-hexadecandioyl-γ-Glu) des(B30) human insulin, did not capture the total insulin action, since pronounced levels of GIR were still present at he 24 hour time point. GIR levels at 24 hours were approximately 2.0 and 3.0 mg/kg/min for LysB29(Nε-hexadecandioyl-γ-Glu) des(B30) human insulin after the low or high dose, respectively. The corresponding values for insulin glargine were approximately 0.8 and 1.8 mg/kg/min.

Mean GIRmax was higher for IGlar (5.6 and 4.2 mg/kg/min) than for LysB29(Nε-hexadecandioyl-γ-Glu) des(B30) human insulin (4.68 and 4.02 mg/kg/min, respectively), after the highest dose but GIRmax was equal after the lower doses (3.07 mg/kg/min).

Mean GIR Time to GIRmax was longer for LysB29(Nε-hexadecandioyl-γ-Glu) des(B30) human insulin (13.2 hours and 6.1 for low and high dose respectively) than for IGlar (5.0 and 4.1 hours for low and high dose, respectively)

Mean peak to trough ranges were less for LysB29(Nε-hexadecandioyl-γ-Glu) des(B30) human insulin than after insulin glargine. The values were 1.0 and 0.7 mg/kg/min after the low and high dose, respectively. For insulin glargine the corresponding values were 1.6 and 1.1 mg/kg/min.

Average time to loss of glucose control was longer for LysB29(Nε-hexadecandioyl-γ-Glu) des(B30) human insulin than for glargine at both dose levels. This occurred after approximately 40 hours after the low LysB29(Nε-hexadecandioyl-γ-Glu) des(B30) human insulin dose and no significant loss of glucose control (defined as an increase of blood glucose of more than a 10 mg/dl) was seen at the 42 hours time point after the high LysB29(Nε-hexadecandioyl-γ-Glu) des(B30) human insulin dose. After insulin glargine dosing the loss of glucose control occurred after approximately 24 hours and 26 hours when administering the low and high dose, respectively.

The mean time to the maximum concentration (Cmax) was shorter for insulin glargine than for LysB29(Nε-hexadecandioyl-γ-Glu) des(B30) human insulin. For insulin glargine the values were 7.2 and 6.4 hours whereas the values for LysB29(Nε-hexadecandioyl-γ-Glu) des(B30) human insulin were 9.2 and 10.1 hours after the middle and high dose, respectively.

The mean terminal half-life was 25.2 hours (95% CI 23 to 28 hours) for LysB29(Nε-hexadecandioyl-γ-Glu) des(B30) human insulin and 13.9 hours (95% CI 13 to 15) hours for IGlar.

Key Safety Results
In general, multiple-dose administration of LysB29(Nε-hexadecandioyl-γ-Glu) des(B30) human insulin and IGlar, respectively, was well tolerated in subjects with type 1 diabetes.

Key Conclusions
LysB29(Nε-hexadecandioyl-γ-Glu) des(B30) human insulin appeared to have a flatter and more protracted action profile and a longer duration of action compared with IGlar as evidenced by the GIR profile characteristics. The data show that LysB29(Nε-hexadecandioyl-γ-Glu) des(B30) human insulin has a lower GIRmax at a comparable dose, longer time to GIRmax at both dose levels and less peak to trough range. The duration of action of LysB29(Nε-hexadecandioyl-γ-Glu) des(B30) human insulin under the present circumstances was approximately 40 hours or longer. The data show that LysB29(Nε-hexadecandioyl-γ-Glu) des(B30) human insulin has the ability to control blood glucose for a longer period. The conclusions based on activity data (pharmacodynamics) are supported by the pharmacokinetic data (longer time to Cmax and longer terminal half-life).

Clinical Example 2

Investigating the Clinical Effect of LysB29(Nε-hexadecandioyl-γ-Glu) des(B30) Human Insulin Administered Once Daily with Varying Intervals.

Key Methodological Elements and Results
The trial was designed to assess the feasibility, efficacy, safety and tolerability of LysB29(Nε-hexadecandioyl-γ-Glu) des(B30) human insulin (600 nmol/mL) for the treatment of subjects with type 2 diabetes once daily with varying injection intervals (flexible injection). The treatment consisted of administration of insulin with or without metformin and/or sufonylurea and/or pioglitazone, in subjects with type 2 diabetes failing on insulin treatment or oral antidiabetic (OAD) treatment or the combination of insulin and OAD treatment. The feasibility of varying injection intervals (i.e. flexible injection) with LysB29(Nε-hexadecandioyl-γ-Glu) des(B30) human insulin was investigated by having participating subjects inject in the morning (between waking up and breakfast) on Mondays, Wednesdays and Fridays, while injecting in the evening (between evening meal and bedtime) on Tuesdays, Thursdays, Saturdays and Sundays as shown in Table 5.

TABLE 5

Dosing regime for flexible injection

| | Mondays | Tuesdays | Wednesdays | Thursdays | Fridays | Saturdays | Sundays |
|---|---|---|---|---|---|---|---|
| Time of administration | Morning[1] | Evening[2] | Morning | Evening | Morning | Evening | Evening |

[1]Morning is defined as between waking up and breakfast
[2]Evening is defined as between evening meal and bedtime Primary Objective To assess glucose control with respect to HbA1c after 26 weeks of treatment with LysB29(Nε-hexadecandioyl-γ-Glu) des(B30) human insulin once daily with varying injection intervals (flexible injection), LysB29(Nε-hexadecandioyl-γ-Glu) des(B30) human insulin once daily given with the evening meal or insulin glargine once daily given at the same time each day (according to the approved label), all in combination with metformin and/or sulfonylurea and/or pioglitazone in subjects with type 2 diabetes failing on insulin treatment or oral antidiabetic (OAD) treatment or the combination of insulin and OAD treatment.

Materials and Methods

The trial was performed in subjects with type 2 diabetes, previously treated with one or more of the oral antidiabetic agents: metformin, sulfonylurea, pioglitazone or with any basal insulin treatment or the combination of the OADs specified and any basal insulin treatment. At randomisation, subjects continued their OAD treatment (if any) while adding, starting or switching to basal insulin LysB29(Nε-hexadecandioyl-γ-Glu) des(B30) human insulin once daily with varying injection intervals or LysB29(Nε-hexadecandioyl-γ-Glu) des(B30) human insulin once daily with the evening meal or insulin glargine once daily at the same time each day (according to label).

A total of 687 subjects with type 2 diabetes, age of 56 years, mean duration of diabetes of 10.6 years, mean BMI of 29.6 kg/m$^2$, mean FPG of 8.9 mmol/L, and mean HbA$_{1c}$ of 8.4% were randomised (1:1:1) to receive once-daily LysB29(Nε-hexadecandioyl-γ-Glu) des(B30) human insulin given with varying injection intervals (229 subjects) or once-daily LysB29(Nε-hexadecandioyl-γ-Glu) des(B30) human insulin given with the evening meal (228 subjects) or once-daily insulin glargine (230 subjects), alone or in combination with metformin and/or SU and/or Pioglitazone, for a treatment period of 26 weeks.

The specific combinations of OAD and insulin treatment prior to randomisation can be seen in Table 12.

The insulin types used prior to randomisation to the study insulin products are shown in Table 6.

In Table 7 the OAD(s) used prior to and during the experiment are shown.

TABLE 6

Insulin at Screening—Summary—Full Analysis Set

| | IDeg OD FF | | IDeg OD | | IGlar OD | | Total | |
|---|---|---|---|---|---|---|---|---|
| | N | (%) | N | (%) | N | (%) | N | (%) |
| Number of Subjects | 229 | | 228 | | 230 | | 687 | |
| Basal insulin | 96 | (41.9) | 96 | (42.1) | 96 | (41.7) | 288 | (41.9) |
| IDet | 19 | (8.3) | 21 | (9.2) | 21 | (9.1) | 61 | (8.9) |
| IGlar | 43 | (18.8) | 41 | (18.0) | 30 | (13.0) | 114 | (16.6) |
| NPH insulin | 34 | (14.8) | 34 | (14.9) | 45 | (19.6) | 113 | (16.4) |
| Bolus insulin | | | | | 1 | (0.4) | 1 | (0.1) |
| IAsp | | | | | 1 | (0.4) | 1 | (0.1) |
| Premix | | | 1 | (0.4) | | | 1 | (0.1) |

N: Number of Subjects
%: Proportion of Subjects
Subjects can use more than one type of insulin within each group
Insulin NPH: Neutral Protamine Hagedorn

TABLE 7

OAD Treatment Type at Baseline and End of Trial

| | IDeg | | | | IGlar | | | |
|---|---|---|---|---|---|---|---|---|
| | Baseline | | End of Trial | | Baseline | | End of Trial | |
| Trial (wks) | N | (%) | N | (%) | N | (%) | N | (%) |
| 3668 (26) FF | | | | | | | | |
| Biguanide | 207 | (90.4) | 206 | (90.0) | 211 | (91.7) | 212 | (92.2) |
| Metformin | 207 | (90.4) | 206 | (90.0) | 211 | (91.7) | 212 | (92.2) |
| DPP-4 inhibitor | | | | | 1 | (0.4) | 1 | (0.4) |
| Sitagliptin | | | | | 1 | (0.4) | 1 | (0.4) |
| Glinide | 10 | (4.4) | 10 | (4.4) | 8 | (3.5) | 7 | (3.0) |
| Repaglinide | 10 | (4.4) | 10 | (4.4) | 8 | (3.5) | 7 | (3.0) |
| Sulphonylurea | 159 | (69.4) | 156 | (68.1) | 157 | (68.3) | 155 | (67.4) |
| Glibenclamide | 55 | (24.0) | 54 | (23.6) | 57 | (24.8) | 55 | (23.9) |
| Gliclazide | 43 | (18.8) | 41 | (17.9) | 39 | (17.0) | 39 | (17.0) |
| Glimepiride | 56 | (24.5) | 56 | (24.5) | 54 | (23.5) | 54 | (23.5) |
| Glipizide | 5 | (2.2) | 5 | (2.2) | 7 | (3.0) | 7 | (3.0) |
| Thiazolidinedione | 13 | (5.7) | 12 | (5.2) | 17 | (7.4) | 16 | (7.0) |
| Pioglitazone | 13 | (5.7) | 12 | (5.2) | 16 | (7.0) | 15 | (6.5) |
| Rosiglitazone | | | | | 1 | (0.4) | 1 | (0.4) |
| 3668 (26) | | | | | | | | |
| Biguanide | 205 | (89.9) | 205 | (89.9) | | | | |
| Metformin | 205 | (89.9) | 205 | (89.9) | | | | |
| Glinide | 14 | (6.1) | 13 | (5.7) | | | | |
| Repaglinide | 14 | (6.1) | 13 | (5.7) | | | | |
| Sulphonylurea | 136 | (59.6) | 136 | (59.6) | | | | |
| Glibenclamide | 51 | (22.4) | 50 | (21.9) | | | | |
| Gliclazide | 37 | (16.2) | 37 | (16.2) | | | | |
| Glimepiride | 44 | (19.3) | 44 | (19.3) | | | | |
| Glipizide | 4 | (1.8) | 4 | (1.8) | | | | |
| Glyburide | | | 1 | (0.4) | | | | |
| Thiazolidinedione | 17 | (7.5) | 17 | (7.5) | | | | |
| Pioglitazone | 17 | (7.5) | 17 | (7.5) | | | | |

Ideg—LysB29(Nε-hexadecandioyl-γ-Glu) des(B30) human insulin
IGlar—insulin glargine,
FF: Fixed injection
End of Trial: a subject's last trial visit excluding the follow-up visit IGlar (3579, 3672, 3586, 3668) and Sita (3580) A subject can be on more than one OAD Efficacy Results HbA$_{1c}$ HbA1c at end of trial and change in HbA1c from baseline to end of trial are given in Table 8.

The confidence interval of the treatment contrast when comparing LysB29(Nε-hexadecandioyl-γ-Glu) des(B30) human insulin given with varying injection intervals with the other treatment groups was within the non-inferiority limit 0.4), which is within the non-inferiority limit accepted by the FDA (Guidance for Industry Diabetes Mellitus: Developing Drugs and Therapeutic Biologics for Treatment and Prevention, draft Guidance, U.S. Department of Health and Human Services Food and Drug Administration Center for Drug Evaluation and Research (CDER) February 2008) Thus, the group receiving LysB29(Nε-hexadecandioyl-γ-Glu) des(B30) human insulin given with varying injection intervals was similar to the other two treatment groups with respect to mean changes in HbA$_{1c}$ from baseline to end of treatment (Table 8 and Table 9).

TABLE 8

Mean HbA1c after 26 Weeks of Treatment

|  | LysB29(Nε-hexadecandioyl-γ-Glu) des(B30) human insulin Once Daily Flexible Injection[2] | LysB29(Nε-hexadecandioyl-γ-Glu) des(B30) human insulin Once daily with the evening meal | Insulin glargine Once daily Same time each day |
|---|---|---|---|
| HbA1c (%) after 26 weeks of treatment[1] | 7.2 | 7.3 | 7.1 |
| Mean Change from Baseline (% points)[1] | −1.28 | −1.07 | −1.26 |

[1]Arithmetic means.
[2]Flexible injection is as defined in Table 5.

TABLE 9

ANOVA[1] of HbA1c after 26 Weeks of Treatment

|  | LysB29(Nε-hexadecandioyl-γ-Glu) des(B30) human insulin Once Daily Flexible Injection[2] |
|---|---|
| Treatment Difference vs. Insulin Glargine Once daily Same time each day (HbA1c % points [95% confidence interval]) | 0.04 [−0.12; 0.20] |
| Treatment Difference vs. LysB29(Nε-hexadecandioyl-γ-Glu) des(B30) human insulin Once daily with the evening meal (HbA1c % points [95% confidence interval]) | −0.13 [−0.29; 0.03] |

[1]Results from ANOVA with treatment, anti-diabetic therapy at screening, sex, region, age and baseline HbA1c as explanatory variables.
[2]Flexible injection is as defined in Table 5.

Hypoglycaemia

Only six severe hypoglycaemic events were reported during the trial cf. Table 10.

TABLE 10

Overview of Hypoglycaemia

| Hypoglycaemic episodes[1] | LysB29(Nε-hexadecandioyl-γ-Glu) des(B30) human insulin Once Daily Flexible Injection[5] | | | Insulin glargine Once daily Same time each day | | | LysB29(Nε-hexadecandioyl-γ-Glu) des(B30) human insulin Once daily with the evening meal | | |
|---|---|---|---|---|---|---|---|---|---|
|  | N[2] | (%)[3] | E[4] | N | (%) | E | N | (%) | E |
| Severe | 1 | (0.4) | 2 | 2 | (0.9) | 2 | 2 | (0.9) | 2 |
| Documented Symptomatic | 149 | (64.8) | 841 | 124 | (54.9) | 770 | 139 | (60.7) | 803 |
| Asymptomatic | 162 | (70.4) | 879 | 159 | (70.4) | 991 | 161 | (70.3) | 892 |
| Probable Symptomatic | 20 | (8.7) | 30 | 15 | (6.6) | 29 | 18 | (7.9) | 32 |
| Relative | 27 | (11.7) | 53 | 24 | (10.6) | 35 | 26 | (11.4) | 78 |
| Unclassifiable | 12 | (5.2) | 15 | 7 | (3.1) | 11 | 7 | (3.1) | 8 |

[1]Hypoglycaemic episodes defined as: severe = hypoglycaemic episode where food, glucagon or i.v. glucose had to be administered to the subject by another person because of severe central nervous system dysfunction associated with the hypoglycaemic episode, Documented Symptomatic = non-severe episode with subjective symptoms and plasma glucose value below 3.9 mmol/L, Asymptomatic = non-severe episode and plasma glucose value below 3.9 mmol/L and no symptoms, Probable Symptomatic = non-severe episode with no plasma glucose value but with subjective symptoms, Relative = non-severe episode with subjective symptoms and a plasma glucose value above or equal to 3.9 mmol/L.
[2]N: number of subjects.
[3]%: percentage of subjects.
[4]E: number of events.
[5]Flexible injection is as defined in Table 5.

Insulin Dose

TABLE 11

Mean[1] Daily Insulin Dose after 26 Weeks of Treatment

|  | LysB29(Nε-hexadecandioyl-γ-Glu) des(B30) human insulin Once daily Flexible injection[2] | LysB29(Nε-hexadecandioyl-γ-Glu) des(B30) human insulin Once daily with the evening meal | Insulin glargine Once daily Same time each day |
|---|---|---|---|
| Daily Dose (U/kg) | 0.55 | 0.52 | 0.52 |

[1]Arithmetic mean.
[2]Flexible injection is as defined in Table 5.

Conclusions

It was surprisingly found that using LysB29(Nε-hexadecandioyl-γ-Glu) des(B30) human insulin, which has a long duration of action and a peak-less and stable activity profile, subjects with type 2 diabetes were sufficiently regulated with once daily dosing administered with varying injection intervals alone or in combination with OAD treatment.

In subjects with type 2 diabetes failing treatment with OAD and/or insulin 26 weeks treatment with LysB29(Nε-hexadecandioyl-γ-Glu) des(B30) human insulin given flexibly (with varying injection intervals) with or without metformin and/or sulfonylurea and/or pioglitazone, resulted in comparable (non-inferior) glycaemic control and comparable incidence of hypoglycaemic episodes to that observed for LysB29(Nε-hexadecandioyl-γ-Glu) des(B30) human insulin given with the evening meal and to the glycaemic control and the incidence of hypoglycaemic episodes observed for insulin glargine given once daily at the same time each day (according to the approved label).

Clinical Example 3

Investigating the Clinical Effect of LysB29(Nε-hexadecandioyl-γ-Glu) des(B30) Human Insulin Administered Once Daily with Varying Intervals.

Key Methodological Elements and Results

The trial was designed to assess the feasibility, efficacy, safety and tolerability of LysB29(Nε-hexadecandioyl-γ-Glu)

des(B30) human insulin (600 nmol/mL) for the treatment of subjects with type 1 diabetes once daily with varying injection intervals (flexible injection). The treatment consisted of administration of basal insulin (LysB29(Nε-hexadecandioyl-γ-Glu) des(B30) human insulin or insulin glargine) in combination with separate injections of bolus insulin, (AspB28 human insulin). The feasibility of varying injection intervals (i.e. flexible injection) with LysB29(Nε-hexadecandioyl-γ-Glu) des(B30) human insulin was investigated by having participating subjects inject in the morning (between waking up and breakfast) on Mondays, Wednesdays and Fridays, while injecting in the evening (between evening meal and bedtime) on Tuesdays, Thursdays, Saturdays and Sundays as shown in Table 12.

TABLE 12

Dosing regime for flexible injection

|  | Mondays | Tuesdays | Wednesdays | Thursdays | Fridays | Saturdays | Sundays |
|---|---|---|---|---|---|---|---|
| Time of administration | Morning[1] | Evening[2] | Morning | Evening | Morning | Evening | Evening |

[1]Morning is defined as between waking up and breakfast
[2]Evening is defined as between evening meal and bedtime Primary Objective To assess glucose control with respect to HbA1c after 26 weeks of treatment with LysB29(Nε-hexadecandioyl-γ-Glu) des(B30) human insulin once daily with varying injection intervals (flexible injection), LysB29(Nε-hexadecandioyl-γ-Glu) des(B30) human insulin once daily given with the evening meal or insulin glargine once daily given at the same time each day (according to the approved label), all in combination with AspB28 human insulin in subjects with type 1 diabetes.

Materials and Methods

The trial was performed in subjects with type 1 diabetes, previously treated with insulin for at least 12 months. At randomisation, subjects switched to basal insulin LysB29(Nε-hexadecandioyl-γ-Glu) des(B30) human insulin once daily with varying injection intervals or LysB29(Nε-hexadecandioyl-γ-Glu) des(B30) human insulin once daily with the evening meal or insulin glargine once daily at the same time each day (according to label) all in combination with AspB28 human insulin.

A total of 490 subjects with type 1 diabetes, age of 56 years, mean duration of diabetes of 10.6 years, mean BMI of 29.6 kg/m$^2$, mean FPG of 8.9 mmol/L, and mean HbA$_{1c}$ of 8.4% were randomised (1:1:1) to receive once-daily LysB29(Nε-hexadecandioyl-γ-Glu) des(B30) human insulin given with varying injection intervals (164 subjects) or once-daily LysB29(Nε-hexadecandioyl-γ-Glu) des(B30) human insulin given with the evening meal (165 subjects) or once-daily insulin glargine, given according to label, (161 subjects) for a treatment period of 26 weeks.

The specific insulin treatment prior to randomisation can be seen in Table 6. The insulin types used prior to randomisation to the study insulin products are shown in Table 7.

Efficacy Results

HbA$_{1c}$

HbA1c at end of trial and change in HbA1c from baseline to end of trial are given in Table 13. The confidence interval of the treatment contrast when comparing LysB29(Nε-hexadecandioyl-γ-Glu) des(B30) human insulin given with varying injection intervals with the other treatment groups was within the non-inferiority limit of 0.4 (Table 14).

TABLE 13

Mean HbA$_{1c}$ after 26 Weeks of Treatment

|  | LysB29(Nε-hexadecandioyl-γ-Glu) des(B30) human insulin Once Daily Flexible Injection[2] | LysB29(Nε-hexadecandioyl-γ-Glu) des(B30) human insulin Once daily with the evening meal | Insulin glargine Once daily Same time each day |
|---|---|---|---|
| HbA$_{1c}$ (%) after 26 weeks of treatment[1] | 7.31 | 7.30 | 7.14 |
| Mean Change from Baseline (% points)[1] | −0.40 | −0.41 | −0.57 |

[1]Arithmetic means.
[2]Flexible injection is as defined in Table 5.

TABLE 14

ANOVA[1] of HbA$_{1c}$ after 26 Weeks of Treatment

|  | LysB29(Nε-hexadecandioyl-γ-Glu) des(B30) human insulin Once Daily Flexible Injection[2] |
|---|---|
| Treatment Difference vs. Insulin Glargine Once daily Same time each day (HbA1c % points [95% confidence interval]) | 0.17 [0.04; 0.30] |
| Treatment Difference vs. LysB29(Nε-hexadecandioyl-γ-Glu) des(B30) human insulin Once daily with the evening meal (HbA1c % points [95% confidence interval]) | 0.01 [−0.13; 0.14] |

[1]Results from ANOVA with treatment, anti-diabetic therapy at screening, sex, region, age and baseline HbA1c as explanatory variables.
[2]Flexible injection is as defined in Table 5.

Hypoglycaemia

Table 15 shows the hypoglycaemic events that were reported during the trial.

TABLE 15

Overview of Hypoglycaemia

| Hypoglycaemic episodes[1] | LysB29(Nε-hexadecandioyl-γ-Glu) des(B30) human insulin Once Daily Flexible Injection[5] | | | Insulin glargine Once daily Same time each day | | | LysB29(Nε-hexadecandioyl-γ-Glu) des(B30) human insulin Once daily with the evening meal | | |
|---|---|---|---|---|---|---|---|---|---|
| | N[2] | (%)[3] | E[4] | N | (%) | E | N | (%) | E |
| Severe | 17 | (10.4) | 25 | 16 | (9.9) | 37 | 21 | (12.7) | 28 |
| Documented Symptomatic | 154 | (93.9) | 7471 | 153 | (95.0) | 7964 | 161 | (97.6) | 9467 |
| Asymptomatic | 134 | (81.7) | 3982 | 131 | (81.4) | 3978 | 139 | (84.2) | 3763 |
| Probable Symptomatic | 26 | (15.9) | 64 | 24 | (14.9) | 124 | 28 | (17.0) | 171 |
| Relative | 9 | (5.5) | 36 | 7 | (4.3) | 11 | 10 | (6.1) | 20 |
| Unclassifiable | 90 | (54.9) | 682 | 87 | (54.0) | 805 | 94 | (57.0) | 871 |

[1]Hypoglycaemic episodes defined as: severe = hypoglycaemic episode where food, glucagon or i.v. glucose had to be administered to the subject by another person because of severe central nervous system dysfunction associated with the hypoglycaemic episode, Documented Symptomatic = non-severe episode with subjective symptoms and plasma glucose value below 3.9 mmol/L, Asymptomatic = non-severe episode and plasma glucose value below 3.9 mmol/L and no symptoms, Probable Symptomatic = non-severe episode with no plasma glucose value but with subjective symptoms, Relative = non-severe episode with subjective symptoms and a plasma glucose value above or equal to 3.9 mmol/L.
[2]N: number of subjects.
[3]%: percentage of subjects.
[4]E: number of events.
[5]Flexible injection is as defined in Table 5.

Insulin Dose

TABLE 16

Mean[1] Daily Insulin Dose after 26 Weeks of Treatment

| | LysB29(Nε-hexadecandioyl-γ-Glu) des(B30) human insulin Once daily Flexible injection[2] | Insulin glargine Once daily Same time each day | LysB29(Nε-hexadecandioyl-γ-Glu) des(B30) human insulin Once daily with the evening meal |
|---|---|---|---|
| Daily Basal Insulin Dose (U/kg) | 0.42 | 0.42 | 0.38 |
| Daily Prandial Insulin Dose (U/kg) | 0.35 | 0.42 | 0.33 |

[1]Arithmetic mean.
[2]Flexible injection is as defined in Table 5.

Conclusions

It was surprisingly found that using LysB29(Nε-hexadecandioyl-γ-Glu) des(B30) human insulin, which has a long duration of action and a peak-less and stable activity profile, subjects with type 1 diabetes were sufficiently regulated with once daily dosing administered with varying injection intervals in combination with bolus insulin.

In subjects with type 1 diabetes 26 weeks treatment with LysB29(Nε-hexadecandioyl-γ-Glu) des(B30) human insulin given flexibly (with varying injection intervals) in combination with AspB28 human insulin, resulted in non-inferior glycaemic control and comparable incidence of hypoglycaemic episodes to that observed for LysB29(Nε-hexadecandioyl-γ-Glu) des(B30) human insulin given with the evening meal and to the glycaemic control and the incidence of hypoglycaemic episodes observed for insulin glargine given once daily at the same time each day (according to the approved label).

Clinical Example 4

Investigating the Clinical Effect of the Co-Formulated Combination Product of LysB29(Nε-hexadecandioyl-γ-Glu) des(B30) Human Insulin and AspB28 Human Insulin Administered in Relation to Meals with the Option to Change between Meals from Day to Day during the Treatment Period.

Key Methodological Elements and Results

The trial was designed to assess the feasibility, efficacy, safety and tolerability of combination product of LysB29 (Nε-hexadecandioyl-γ-Glu) des(B30) human insulin and AspB28 human insulin (600 nmol/mL) for the treatment of subjects with type 1 diabetes once daily given in relation to a meal with the option to change from day to day the injection time for the combination product of LysB29(Nε-hexadecandioyl-γ-Glu) des(B30) human insulin and AspB28 human insulin to a different meal. The treatment consisted of the administration of the combination product of LysB29 (Nε-hexadecandioyl-γ-Glu) des(B30) human insulin and AspB28 human insulin at one meal and Asp28 human insulin given in relation to remaining insulin-requiring meals in subjects with type 1 diabetes.

Primary Objective

To assess glucose control with respect to HbA1c after 26 weeks of treatment with combination product of LysB29 (Nε-hexadecandioyl-γ-Glu) des(B30) human insulin and AspB28 human insulin in relation to a selected meal (with the option of varying the meal from day to day) or insulin detemir once daily (with the option to optimise to twice daily in not optimally controlled), both treatment arms in combination with Asp28 human insulin with remaining insulin-requiring meals in subjects with type 1 diabetes.

Materials and Methods

The trial was performed in subjects with type 1 diabetes having been diagnosed at least one year prior to entering the trial with an $HbA_{1c}$ between 7 and 10%. At randomisation, subjects were allocated to either of two basal insulin products:
1. the combination of LysB29(Nε-hexadecandioyl-γ-Glu) des(B30) human insulin and AspB28 human insulin once daily with any meal (varying injection time from day to day) or
2. insulin detemir once daily (or twice daily) at the same time each day (according to label). Both treatment arms received AspB28 human insulin as meal time insulin at remaining meals.

A total of 548 subjects with type 1 diabetes, age of 41 years, mean duration of diabetes of 17 years, mean BMI of 26.4 kg/m$^2$, mean FPG of 10.5 mmol/L, and mean HbA$_{1c}$ of 8.3% were randomised (2:1 in favour of the combination of LysB29(Nε-hexadecandioyl-γ-Glu) des(B30) human insulin and AspB28 human insulin for a treatment period of 26 weeks.

Efficacy Results

HbA$_{1c}$

The confidence interval of the treatment contrast when comparing LysB29(Nε-hexadecandioyl-γ-Glu) des(B30) human insulin and AspB28 human insulin with the other treatment group was within the non-inferiority limit of 0.4. The two groups were therefore similar with respect to mean changes in HbA$_{1c}$ from baseline to end of treatment (statistical analysis Table 17).

TABLE 17

Treatment difference between treatment groups in HbA1c (%) at end of trial

|  | LysB29(Nε-hexa-decandioyl-γ-Glu) des(B30) human insulin and AspB28 human insulin |
| --- | --- |
| Treatment Difference vs. insulin detemir[1] (HbA1c % points [95% confidence intervals]) | −0.05 [−0.18; 0.08] |

[1]Results from ANOVA with treatment, anti-diabetic therapy at screening, sex, region, age and baseline HbA1c as explanatory variables Hypoglycaemia Hypoglycaemic episodes were registered during the trial according to the definitions of American Diabetes Association, cf. Table 18.

TABLE 18

Overview of Hypoglycaemia. Randomisation was 2:1 (LysB29(Nε-hexadecandioyl-γ-Glu) des(B30) human insulin and AspB28 human insulin:insulin detemir)

| Hypoglycaemic episodes[1] | LysB29(Nε-hexadecandioyl-γ-Glu) des(B30) human insulin and AspB28 human insulin | | | Insulin Detemir | | |
| --- | --- | --- | --- | --- | --- | --- |
| | N[2] | (%)[3] | E[4] | N | (%) | E |
| Severe | 35 | 9.7 | 56 | 22 | 12.2 | 35 |
| Documented Symptomatic | 319 | 88.1 | 9670 | 156 | 86.7 | 5126 |
| Asymptomatic | 270 | 74.6 | 4032 | 137 | 76.1 | 1804 |
| Probable Symptomatic | 71 | 19.6 | 234 | 40 | 22.2 | 149 |
| Relative | 42 | 11.6 | 108 | 17 | 9.4 | 33 |
| Unclassifiable | 105 | 29.0 | 395 | 50 | 27.8 | 241 |

[1]Hypoglycaemic episodes defined as: severe = hypoglycaemic episode where food, glucagon or i.v. glucose had to be administered to the subject by another person because of severe central nervous system dysfunction associated with the hypoglycaemic episode, Documented Symptomatic = non-severe episode with subjective symptoms and plasma glucose value below 3.9 mmol/L, Asymptomatic = non-severe episode and plasma glucose value below 3.9 mmol/L and no symptoms, Probable Symptomatic = non-severe episode with no plasma glucose value but with subjective symptoms, Relative = non-severe episode with subjective symptoms and a plasma glucose value above or equal to 3.9 mmol/L.
[2]N: number of subjects.
[3]%: percentage of subjects.
[4]E: number of events.

Insulin Dose

TABLE 19

Mean[1] Total Daily Insulin Dose after 26 Weeks of Treatment

|  | LysB29(Nε-hexa-decandioyl-γ-Glu) des(B30) human insulin and AspB28 human insulin + AspB28 human insulin | Insulin Detemir + AspB28 human insulin |
| --- | --- | --- |
| Daily Dose (U/kg) | 0.86 | 1.00 |

[1]Arithmetic mean.

Conclusions

It was surprisingly found that the basal component of the combination product, LysB29(Nε-hexadecandioyl-γ-Glu) des(B30) human insulin, which has a long duration of action and a peak-less and stable activity profile, enabled subjects to be sufficiently regulated with once daily dosing even when varying the injection intervals as a result of changing the meal at which injection of the combination product was administered.

In subjects with type 1 diabetes insulin 26 weeks treatment with LysB29(Nε-hexadecandioyl-γ-Glu) des(B30) human insulin combined with AspB28 human insulin given once daily in relation to a selected meal (with the option of varying the injection time to a different meal from day to day) resulted in comparable (non-inferior) glycaemic control to that of insulin detemir given twice daily according to label, both treatment were combined with AspB28 human insulin for the remaining meals. The combination of LysB29 (Nε-hexadecandioyl-γ-Glu) des(B30) human insulin resulted in lower insulin use and a lower incidence of hypoglycaemic episodes compared to that observed for insulin detemir.

Clinical Studies—Clinical Example 5

Investigating the Clinical Effect of IDegAsp (LysB29(Nε-hexadecandioyl-γ-Glu) des(B30) Human Insulin and AspB28 Human Insulin) Administered at the Largest Meal.

Introduction

In this detailed Clinical Study, IDegAsp (Insulin degludec/insulin as part) is administered to patients with Type 2 diabetes at the largest meal of the day. The results presented herein are from a randomized controlled, Phase 3 Trial. The discussion herein is based on actual measurements. However, in some places we discuss estimated rates (e.g. those obtained from a suitable statistical model.

Definition of Analysis Sets

The following analysis sets were defined in accordance with the ICH-E9 guidance:

Full Analysis Set (FAS): included all randomised subjects. In exceptional cases, subjects from the FAS could be eliminated. In such cases, the elimination was to be justified and documented. The statistical evaluation of the FAS was to follow the intention-to-treat principle and subjects were to contribute to the evaluation 'as randomised'.

Per Protocol (PP) Analysis Set: included subjects without any major protocol violations that may have affected the primary endpoint. Moreover, subjects must have been exposed to the investigational product or its comparator for more than 12 weeks and were to have a valid assessment necessary for deriving the primary endpoint. Subjects in the PP set were to contribute to the evaluation 'as treated'.

Safety Analysis Set: included all subjects who received at least one dose of the investigational product or its comparator. Subjects in the safety set were to contribute to the evaluation 'as treated'.

Randomised subjects who were lost to follow-up and where no exposure information of the investigational product or its comparator was available after randomisation were to be handled as unexposed. All OADs were regarded as non-investigational products.

Before data were released for statistical analysis, a blinded review of all data was to take place to identify protocol deviations that may potentially have affected the results. This review was to be performed without revealing which trial product the subjects were assigned to. The blinding of the trial products was to be maintained for everyone involved in defining the analysis sets until data were released for statistical analysis. Furthermore, extreme values and outliers were to be identified by the statistician during programming and data review according to ICH-E930, using a fake randomisation.

Subjects who were exposed to trial products <12 weeks and who did not have a valid assessment of $HbA_{1c}$ after randomisation were excluded from the PP analysis, as were subjects who violated the selection criteria in the trial. The decision to exclude any subject or observation from the statistical analysis was the joint responsibility of the blinded members of the study group. The subjects or observations to be excluded and the reason for their exclusion were to be documented and signed by all parties, prior to database release. The documentation was to be stored together with the remaining trial documentation.

Statistical Analyses

Primary Endpoint

The primary endpoint was change from baseline in $HbA_{1c}$ (%) after 26 weeks of treatment.

Statistical Analysis

Change from baseline in $HbA_{1c}$ after 26 weeks of treatment was analysed using an analysis of variance (ANOVA) method with treatment, antidiabetic therapy at screening and sex as fixed factors, and age and baseline $HbA_{1c}$ as covariates. The antidiabetic therapy at screening was a factor with the following two levels: 1. SU and/or glinides and 2: Other.

The model was to be fitted to all the data simultaneously (all treatment groups) and from this model the relevant treatment differences were to be estimated.

Non-inferiority was considered confirmed if the upper bound of the two-sided 95% CI was below or equal to 0.4% or equivalent if the p-value for the one-sided test of $$H_0: D>0.4\% \text{ against } H_A: D\leq 0.4\%,$$

was less than or equal to 2.5%, where D is the mean treatment difference (investigational product minus comparator).

If non-inferiority was confirmed, the superiority of the investigational product over comparator was to be investigated. Superiority was considered confirmed if the upper bound of the two-sided 95% CI, which was calculated using the FAS, was below 0%. The PP analysis was considered supportive here.

Sensitivity Analysis

The following sensitivity analyses were to be performed using the FAS only.

All observed $HbA_{1c}$ measurements available post randomisation at scheduled measurement times were also to be analysed in a linear mixed model using an unstructured residual covariance matrix (if possible). This approach relies on the assumption that data are missing at random according to the taxonomy defined by Rubin (1976 Biometrika vol 63(3) pp 581-592). The results were compared to the results of the LOCF method for dealing with missing data. Any marked difference concerning treatment differences between the missing at random approach and the LOCF approach was to be commented upon in the CTR.

Change in $HbA_{1c}$ from baseline was also analysed using a model with only treatment as fixed factor and baseline $HbA_{1c}$ as covariate to assess the sensitivity of the results to inclusion/exclusion of fixed factors and covariates.

Confirmatory Secondary Endpoints

Provided non-inferiority was confirmed for the primary endpoint, a number of confirmatory secondary endpoints were to be tested to confirm superiority of the investigational product over the comparator.

The confirmatory secondary endpoints are given below together with the direction of the test for superiority. The order of the endpoints defined the testing sequence.

1. Prandial PG increment at dinner after 26 weeks of treatment (90 minutes after start of dinner as measured by SMPG)

Superiority was considered confirmed if the 95% CI for the treatment difference (investigational product minus comparator) was entirely below zero.

2. Responder without hypoglycaemic episodes ($HbA_{1c}<7.0\%$ at end-of-trial and no severe or minor episodes during the last 12 weeks of treatment including only subjects exposed for at least 12 weeks)

Superiority was considered confirmed if the 95% CI for the odds ratio (investigational product/comparator) was entirely above one.

3. Number of treatment-emergent nocturnal (00:01-05:59 a.m.) severe or minor hypoglycaemic episodes
   Superiority was considered confirmed if the 95% CI for the relative risk (investigational product/comparator) was entirely below one.
4. Change from baseline in body weight after 26 weeks of treatment
   Superiority was considered confirmed if the 95% CI for the treatment difference (investigational product minus comparator) was entirely below zero.
   Prandial Plasma Glucose Increment at Dinner
   Prandial PG increment at dinner of the day (where insulin was injected) was derived from the 9-point SMPG profile as the difference between PG values available before dinner and 90 minutes after dinner.
   The endpoint after 26 weeks of treatment was analysed using an ANOVA method with treatment, antidiabetic therapy at screening and sex as fixed factors, and age and PG increment at baseline as covariates.
   Responder without Hypoglycaemic Episodes
   Responder without hypoglycaemic episodes is a dichotomous endpoint (responder/non-responder) that is defined based on whether a subject has met the ADA $HbA_{1c}$ target at end-of-trial ($HbA_{1c}$<7%) without treatment-emergent severe or minor hypoglycaemic episodes during the last 12 weeks of treatment. Severe hypoglycaemic episodes are defined according to the ADA classification while minor hypoglycaemic episodes (PG<3.1 mmol/L) is an additional group. A hypoglycaemic episode is defined as treatment-emergent if the onset of the episode is on or after the first day of exposure to randomised treatment and no later than 7 days after the last day of randomised treatment. The endpoint was only defined for subjects that had been exposed to the investigational product or its comparator for at least 12 weeks.
   Responder analysis was based on a logistic regression model using treatment, antidiabetic therapy at screening and sex as fixed factors, and age and baseline $HbA_{1c}$ as covariates.
   Number of Nocturnal Treatment-Emergent Severe or Minor Hypoglycaemic Episodes
   This counting endpoint is defined as the sum of treatment-emergent nocturnal severe and minor hypoglycaemic episodes. Any episode that had time of onset between 00:01 and 05:59 a.m. (both included) was to be considered nocturnal.
   The number of nocturnal hypoglycaemic episodes was analysed using a negative binomial regression model with a log-link function and the logarithm of the time period in which a hypoglycaemic episode was considered treatment-emergent as offset. The model included treatment, antidiabetic therapy at screening and sex as fixed factors and age as covariate.
   Change from Baseline in Body Weight
   Change from baseline in body weight after 26 weeks of treatment was analysed using an ANOVA method with treatment, antidiabetic therapy at screening and sex as fixed factors, and age and baseline body weight as covariates.
   Supportive Secondary Endpoints
   $HbA_{1c}$ Responder Endpoints
   Dichotomous endpoints (responder/non-responder) were defined based on whether a subject had met a specific target—e.g. at least the ADA $HbA_{1c}$ target ($HbA_{1c}$<7%). Another example of a target is the International Diabetes Federation $HbA_{1c}$ target ($HbA_{1c}$≤6.5%).
   Additional dichotomous endpoints were defined based on whether those treatment targets at end of trial were achieved without hypoglycaemic episodes in the last 12 weeks of treatment considering severe episodes only, and severe and minor episodes together. The endpoints were only defined for subjects that had been exposed for at least 12 weeks.
   The responder endpoints were analysed separately based on a logistic regression model using treatment, antidiabetic therapy at screening and sex as fixed factors, and age and baseline $HbA_{1c}$ as covariates.
   Fasting Plasma Glucose
   Change from baseline in FPG was analysed using an ANOVA method with treatment, antidiabetic therapy at screening and sex as fixed factors, and age and baseline FPG as covariates.
   Self-Measured Plasma Glucose
   Self-measured plasma glucose was measured in terms of the 9-point SMPG profiles and 1-point SMPG profiles used for insulin dose adjustments.
   9-Point Profile (SMPG)
   The 9-point profile (SMPG) included measurements before and 90 minutes after start of breakfast, lunch and main evening meal, measurements prior to bedtime and at 4 a.m., and before breakfast the following day.
   The endpoints from the 9-point (SMPG) profiles were
   9-point profile (SMPG)
   Mean of the 9-point profile (SMPG)
   Fluctuation in 9-point profile (SMPG)
   Prandial PG increments
   Changes between nocturnal SMPG measurements
   The mean of the 9-point profile (SMPG) is defined as the area under the profile divided by the measurement time and is calculated using the trapezoidal method. The fluctuation in the 9-point profile (SMPG) is defined as $$\frac{1}{T}\int_0^T |PG(t) - \overline{PG}| dt$$

where T, PG(t) and $\overline{PG}$ denotes the length of the profile, the PG value at time t and the mean of the profile, respectively.
   Prandial PG increment for each meal was derived from the 9-point profile (SMPG) as the difference between PG values available 90 minutes after meal and before meal. Mean prandial PG increment over all meals was derived as the mean of all available meal increments.
   Change between nocturnal PG was assessed by considering the differences between PG values available prior bedtime, at 4 a.m. and the before breakfast value the following day: (4 a.m. PG value minus prior bedtime PG value), (before breakfast PG value minus prior bedtime PG value) and (before breakfast PG value minus 4 a.m. PG value).
   A mixed effect model was fitted to the 9-point profile (SMPG) data. The model included treatment, time, interaction between treatment and time, antidiabetic therapy at screening and sex as fixed factors, age as covariate and subject as random effect. From the model, mean profile by treatment and relevant treatment differences were estimated and explored.
   Mean and fluctuation in the 9-point profile (SMPG), prandial PG increment and nocturnal PG endpoints were analysed separately using an ANOVA method with treatment, antidiabetic therapy at screening and sex as fixed factors, and age and the relevant baseline value as covariates. Fluctuation in the 9-point profile (SMPG) was logarithmically transformed before analysis.

Safety Endpoints

The following safety endpoints were to be assessed:

AEs

Laboratory assessments clinical evaluations

Hypoglycaemic Episodes

Hypoglycaemic episodes were to be recorded by subjects in their trial diaries throughout the trial. The information collected was to include PG before treating the episode and whether the subject was able to treat himself/herself. Information on last meal and dose was also to be collected. This information was used to classify an episode according to the ADA definition (severe, documented symptomatic, asymptomatic, probable symptomatic and relative).

A hypoglycaemic episode was to be defined as treatment-emergent if the onset of the episode was on or after the first day of exposure to randomised treatment and no later than 7 days after the last day of randomised treatment.

The summaries of treatment-emergent hypoglycaemic episodes were made by displaying the following:

the number of subjects with at least one episode the percentage of subjects with at least one episode the number of episodes and the episode rate per 100 PYE separate summaries by severity:

all episodes nocturnal episodes using both the ADA definition and the additional minor category.

The nocturnal period was considered as the period between 00:01 and 05:59 a.m. (both included). A hypoglycaemic episode that had time of onset during this period was to be considered nocturnal.

The number of hypoglycaemic episodes was analysed using a negative binomial regression model with a log-link function and the logarithm of the time period in which a hypoglycaemic episode was considered treatment-emergent as offset. The model was to include treatment, antidiabetic therapy at screening and sex as fixed factors, and age as covariate. To the extent that data allowed, separate analyses were to be performed for severe episodes and severe or minor episodes, considering all episodes and nocturnal episodes separately.

Additional Trial Information

The following Tabulated information presents additional information about the specific trial conducted.

TABLE 20

Treatment Regimen

|  | IDegAsp | IGlar |
|---|---|---|
| Frequency | OD | OD |
| Injection Time | Largest Meal[3] | According to Label[1] |
| Starting Dose | 10 U | 10 U |
| Device | Flexpen ® | Solostar ® |
| Additional Antidiabetic Therapy | ≤2 OADs[2] | ≤2 OADs[2] |

[1]Before breakfast or before bedtime (once a day at the same time every day)
[2]SU/glinides and DPP-IV inhibitors discontinued at randomisation
[3]Subjects choose injection time at time of randomisation

TABLE 21

Main Recruitment Criteria

| Diagnosis | Type 2 diabetes | For ≥6 months |
|---|---|---|
| Daily Insulin Use | Insulin naive | |
| Previous Treatment | 1 or more OADs | For ≥3 months |

TABLE 21-continued

Main Recruitment Criteria

| $HbA_{1c}$ | 7-10% |
|---|---|
| Body Mass Index | ≤35 kg/m$^2$ |
| Age | ≥20 years |

TABLE 22

Baseline Information

| Subject Characteristics | IDegAsp | IGlar | Total |
|---|---|---|---|
| # FAS | 147 | 149 | 296 |
| Sex (% men) | 61 | 66 | 64 |
| Age* (years) | 60 | 61 | 61 |
| Diabetes Duration* (years) | 11 | 12 | 12 |
| Body Weight* (kg) | 66 | 66 | 66 |
| BMI* (kg/m$^2$) | 25.2 | 25.0 | 25.1 |
| $HbA_{1c}$* (%) | 8.3 | 8.5 | 8.4 |
| FPG Central Lab.* (mmol/l) | 9.0 | 9.1 | 9.0 |

*Arithmetic mean

TABLE 23

OAD at Screening
Number of Subjects

|  | IDegAsp | IGlar | Total |
|---|---|---|---|
| Metformin[1] | 8 | 5 | 13 |
| SU/Glinides[1] | 21 | 16 | 37 |
| Metformin + SU/Glinides[2] | 30 | 35 | 65 |
| Others | 88 | 93 | 181 |

[1]Monotherapy
[2]Two OADs

Numbers Derived from Listing of Concomitant Medication

TABLE 24

Antidiabetic Therapy at Screening: Stratification by SU/Glinides or Others
Number of Subjects

|  | IDegAsp | IGlar | Total |
|---|---|---|---|
| SU and/or glinides | 125 | 125 | 250 |
| Others | 22 | 24 | 46 | stratification is used for even distribution in treatment arms

Numbers Derived from Listing of Concomitant Medication

Trial Conduct

TABLE 25

Disposition of Subjects
Number of Subjects

|  | IDegAsp | IGlar | Total |
|---|---|---|---|
| Randomised | 147 | 149 | 296 (100%) |
| Exposed | 147 | 149 | 296 (100%) |
| Completed* | 137 | 137 | 274 (92.6%) |

*Completed: last scheduled treatment visit performed

Number of Subjects in Analysis Sets

TABLE 26

| Number of Subjects | | | |
|---|---|---|---|
| | IDegAsp | IGlar | Total |
| FAS | 147 | 149 | 296 |
| PP Analysis Set | 141 | 140 | 281 |
| Safety Set | 147 | 149 | 296 |

FAS: Full Analysis Set
PP: Per Protocol

TABLE 27

| Exposure to Trial Insulin | | | |
|---|---|---|---|
| | IDegAsp | IGlar | Total |
| Number of Exposed Subjects | 147 | 149 | 296 |
| Patient Years of Exposure | 70.0 | 70.2 | 140.2 |

Results for Clinical Example 5

The results for Example 5 are presented in the attached Figures. The results are further discussed herein.

$HbA_{1c}$—Primary Endpoint

Figure 2:
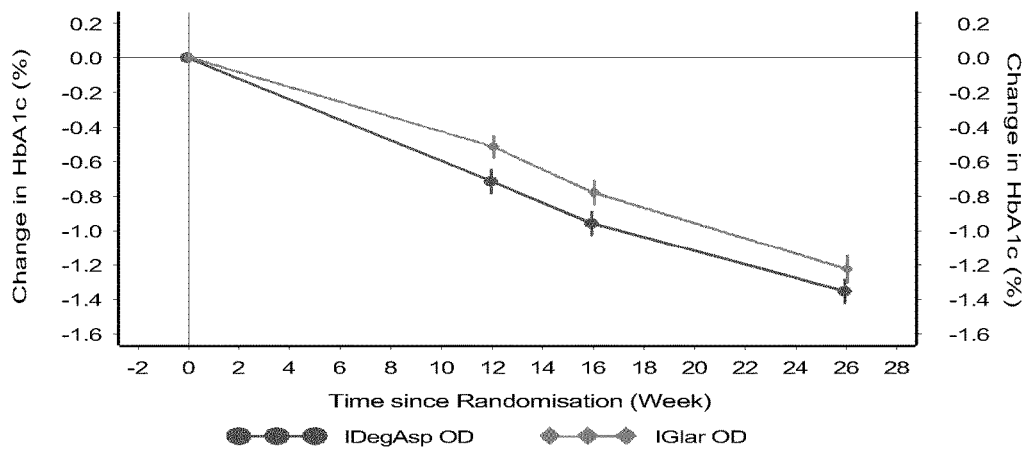
FIG. 2 shows a graph.

The primary objective of this trial was to confirm the efficacy of IDegAsp in controlling glycaemic with respect to change from baseline in $HbA_{1c}$ after 26 weeks of treatment. IDegAsp improved glycaemic control to a greater extent in the study population as compared to IGlar. Mean $HbA_{1c}$ decreased throughout the trial in both the treatment groups; see the results presented in FIGS. 1 and 2, in particular the results presented in FIG. 1.

After 26 weeks of treatment, the observed mean HbA1c was 7.0% with IDegAsp and 7.3% with IGlar. The observed mean change from baseline to end-of-trial was −1.35%-points and −1.22%-points in the IDegAsp and IGlar group, respectively.

IDegAsp effectively improved glycaemic control (non-inferior to IGlar) and subsequent testing confirmed superiority to IGlar in lowering HbA1c. Both non-inferiority and superiority was confirmed as the upper limit of the 95% CI for the estimated treatment difference was <0.

The estimated mean reduction in HbA1c was −1.61%-points with IDegAsp and −1.33%-points with IGlar, with an estimated mean difference (IDegAsp-IGlar) of −0.28%-points, [−0.46; −0.10]95% CI after 26 weeks of treatment; see Table 28.

TABLE 28

| HbA1c (%) after 26 Weeks of Treatment - Primary Statistical Analysis - Full Analysis Set | | | | |
|---|---|---|---|---|
| | FAS | N | Estimate | SE | 95% CI |
| HbA1c (%) | | | | | |
| LSMeans | | | | | |
| IDegAsp OD | 147 | 147 | 6.81 | 0.08 | |
| IGlar OD | 149 | 149 | 7.09 | 0.08 | |
| Change from Baseline | | | | | |
| LSMeans | | | | | |
| IDegAsp OD | 147 | 147 | −1.61 | 0.08 | |
| IGlar OD | 149 | 149 | −1.33 | 0.08 | |

TABLE 28-continued

| HbA1c (%) after 26 Weeks of Treatment - Primary Statistical Analysis - Full Analysis Set | | | | |
|---|---|---|---|---|
| | FAS | N | Estimate | SE | 95% CI |
| Treatment Contrast | | | | | |
| IDegAsp OD − IGlar OD | | | −0.28 | | [−0.46; −0.10] |

N = Number of subjects contributing to analysis,
CI = Confidence Interval,
SE = Standanard Error of the Mean
The response and change from baseline in the response after 26 weeks of treatment is analysed using an ANOVA method with treatment, antidiabetic treatment at screening and sex as fixed effects, and age and baseline response as covariates.
Missing data is imputed using last observation carried forward.

The primary efficacy analysis was based on both the FAS and the PP analysis set, where the PP analysis was considered as supportive evidence. The result of the analysis using the PP analysis set supported the result from the primary analysis; see Table 29.

The results of the primary analysis were also supported by two additional sensitivity analyses, one based on a simple model, including only HbA1c at baseline as covariate, and one based on a repeated measurement model.

TABLE 29

| $HbA_{1c}$ (%) after 26 Weeks of Treatment - Statistical Sensitivity Analysis - PP Analysis Set | | | | |
|---|---|---|---|---|
| | PP | N | Estimate | SE | 95% CI |
| HbA1c (%) | | | | | |
| LSMeans | | | | | |
| IDegAsp OD | 141 | 141 | 6.70 | 0.07 | |
| IGlar OD | 140 | 140 | 6.95 | 0.07 | |
| Change from Baseline | | | | | |
| LSMeans | | | | | |
| IDegAsp OD | 141 | 141 | −1.71 | 0.07 | |
| IGlar OD | 140 | 140 | −1.46 | 0.07 | |
| Treatment Contrast | | | | | |
| IDegAsp OD − IGlar OD | | | −0.25 | | [−0.41; −0.10] |

N = Number of subjects contributing to analysis,
CI = Confidence Interval,
SE = Standanard Error of the Mean
The response and change from baseline in the response after 26 weeks of treatment is analysed using an ANOVA method with treatment, antidiabetic treatment at screening and sex as fixed effects, and age and baseline response as covariates.
Missing data is imputed using last observation carried forward.

Responders for $HbA_{1c}$

At the end of trial, the observed proportion of subjects who achieved the ADA target of $HbA_{1c}$<7.0% was 58.5% with IDegAsp and 40.3% with IGlar (see Table 30). The observed proportion of responders achieving the $HbA_{1c}$ target of <7.0% was numerically higher in the IDegAsp group compared to the IGlar group at all time points (Weeks 12, 16 and 26).

The observed proportion of subjects who attained the stricter IDF target of $HbA_{1c} \leq 6.5\%$ was 33.3% of subjects treated with IDegAsp and 19.5% of subjects treated with IGlar; see Table 30.

TABLE 30

Responder for HbA$_{1c}$ at End-of-trial - Summary - Full Analysis Set

|  | IDegAsp OD N (%) | IGlar OD N (%) | Total N (%) |
|---|---|---|---|
| Number of Subjects | 147 | 149 | 296 |
| HbA1c < 7.0% (ADA) Visit 28 (Week 26) (LOCF) | | | |
| N | 147 (100.0) | 149 (100.0) | 296 (100.0) |
| Yes | 86 (58.5) | 60 (40.3) | 146 (49.3) |
| No | 61 (41.5) | 89 (59.7) | 150 (50.7) |
| HbA1C <= 6.5% (IDF) Visit 28 (Week 26) (LOCF) | | | |
| N | 147 (100.0) | 149 (100.0) | 296 (100.0) |
| Yes | 49 (33.3) | 29 (19.5) | 78 (26.4) |
| No | 98 (66.7) | 120 (80.5) | 218 (73.6) |

N = Number of Subjects

The estimated odds of achieving the target of HbA$_{1c}$<7% was approximately two times higher with IDegAsp than with IGlar (estimated treatment odds ratio (IDegAsp/IGlar) was 2.10 [1.26; 3.52]95% CI), see Table 31. As the 95% CI for the odds ratio (IDegAsp/IGlar) did not include 1, this difference was statistically significant; see Table 31.

TABLE 31

Responder for HbA$_{1c}$ at End-of-trial - Statistical Analysis - Full Analysis Set

|  | FAS | N | Estimate | 95% CI |
|---|---|---|---|---|
| HbA1c < 7.0% | | | | |
| LSMeans, Odds | | | | |
| IDegAsp OD | 147 | 147 | 2.38 | |
| IGlar OD | 149 | 149 | 1.13 | |
| Treatment Odds Ratio | | | | |
| IDegAsp OD/IGlar OD | | | 2.10 | [1.26; 3.52] |
| HbA1c <= 6.5% | | | | |
| LSMeans, Odds | | | | |
| IDegAsp OD | 147 | 147 | 0.84 | |
| IGlar OD | 149 | 149 | 0.38 | |
| Treatment Odds Ratio | | | | |
| IDegAsp OD/IGlar OD | | | 2.20 | [1.20; 4.02] |

N = Number of subjects contributing to analysis,
CI = Confidence Interval
The binary endpoint is analysed in a Logistic Regression Model using a logit link.
The model includes treatment, antidiabetic treatment at screening and sex as fixed effects, and age and baseline HbA$_{1c}$ as covariates.
Missing data is imputed using last observation carried forward.
End of Trial: a subject's last end of trial visit excluding the follow-up visit.

In line with this, the estimated odds of achieving the target of HbA$_{1c}$≤6.5% at end of trial was also approximately two times higher with IDegAsp than with IGlar, as the lower limit of the 95% CI for the estimated odds ratio (IDegAsp/IGlar odds ratio: 2.20 [1.20; 4.02]$_{95\% CI}$) was >1, see Table 31.

Subjects Achieving HbA$_{1c}$ Targets without Hypoglycaemia

In all, a numerically higher proportion of subjects treated with IDegAsp (43.3%) than IGlar (25.0%) achieved the HbA$_{1c}$ target <7% without confirmed hypoglycaemic episodes during the last 12 weeks of treatment; see Table 32.

TABLE 32

Responder for HbA1c at End-of-trial without Hypoglycaemia - Summary - Full Analysis Set

|  | IDegAsp OD N (%) | IGlar OD N (%) | Total N (%) |
|---|---|---|---|
| Number of Subjects | 147 | 149 | 296 |
| HbA1c < 7.0% w/o Confirmed Hypo. Visit 28 (Week 26) (LOCF) | | | |
| N | 141 (100.0) | 140 (100.0) | 281 (100.0) |
| Yes | 61 (43.3) | 35 (25.0) | 96 (34.2) |
| No | 80 (56.7) | 105 (75.0) | 185 (65.8) |
| HbA1c <= 6.5% w/o Confirmed Hypo. Visit 28 (Week 26) (LOCF) | | | |
| N | 141 (100.0) | 140 (100.0) | 281 (100.0) |
| Yes | 36 (25.5) | 22 (15.7) | 58 (20.6) |
| No | 105 (74.5) | 118 (84.3) | 223 (79.4) |

N = Number of Subjects
Responder for HbA$_{1c}$ without hypoglycaemia: subject meeting the HbA$_{1c}$ target at the end of trial without treatment-emergent hypoglycaemia during the last 12 weeks of trt. Endpoint is only defined for subjects exposed for at least 12 trt. weeks. End of Trial: a subject's last end of trial visit excluding the follow-up visit. Confirmed hypoglycaemia: subject unable to treat himself/herself and/or have a recorded PG < 3.1 mmol/L (56 mg/dL)

The proportion of subjects achieving HbA$_{1c}$<7% at the end of the trial without episodes of confirmed hypoglycaemia was specified as a confirmatory secondary endpoint.

The statistical analysis confirmed that IDegAsp was superior to IGlar in terms of a higher proportion of subjects achieving HbA$_{1c}$<7% without confirmed hypoglycaemic episodes, as the lower limit of the 95% CI for the estimated odds ratio (IDegAsp/IGlar) was >1. The estimated odds of achieving this target was approximately two times higher with IDegAsp compared to IGlar, (odds ratio 2.21 [1.25; 3.92]$_{95\% CI}$); see Table 33.

TABLE 33

HbA$_{1c}$ < 7.0% at End-of-trial without Confirmed Hypoglycaemia -Confirmatory Statistical Analysis - Full Analysis Set

|  | FAS | N | Estimate | 95% CI |
|---|---|---|---|---|
| HbA1c < 7.0% w/o Confirmed Hypo | | | | |
| LSMeans, Odds | | | | |
| IDegAsp OD | 147 | 141 | 1.09 | |
| IGlar OD | 149 | 140 | 0.49 | |
| Treatment Odds Ratio | | | | |
| IDegAsp OD/IGlar OD | | | 2.21 | [1.25; 3.92] |

N = Number of subjects contributing to analysis,
CI = Confidence Interval.
The endpoint is analysed in a Logistic Regression Model using a logit link, including treatment, antidiabetic treatment at screening and sex as fixed effects, and age and baseline HbA$_{1c}$ as covariates. Missing data is imputed using LOCF. HbA$_{1c}$ < 7.0% w/o Hypo: A subject exposed for at least 12 weeks, who meets HbA$_{1c}$ target w/o hypoglycaemia during last 12 weeks of treatment or within 7 days from last randomised treatment. End of Trial: a subject's last end of trial visit excluding the follow-up visit. Confirmed hypo.: subject unable to treat himself/herself and/or have a recorded PG < 3.1 mmol/L (56 mg/dL).

The estimated odds (IDegAsp/IGlar) of achieving the more stringent target HbA$_{1c}$≤6.5% without episodes of confirmed hypoglycaemia was 1.78 [0.90; 3.51]$_{95\% CI}$. No statistical significant difference was observed between the treatment groups as the 95% CI for the estimated odds ratio (IDegAsp/IGlar) included 1.

In accordance to the pre-planned statistical analyses, the proportion of subjects achieving the target HbA$_{1c}$<7% or HbA$_{1c}$≤6.5% without severe hypoglycaemia were performed. There were no episodes of severe hypoglycaemia reported for this trial.

The following Primary Statistical Analysis for $HbA_{1c}$ at Week 26 confirms the superiority of the combination of the present invention.

TABLE 34

| Analysis Set | Estimated difference [CI95%] |
|---|---|
| FAS | −0.28 [−0.46; −0.10] |

Table 34 contains an extract from Table 28.

Summary of Clinical Example 5

In this example, IDegAsp is administered to patients with Type 2 diabetes inadequately controlled with oral drugs. The results presented herein are from a randomized controlled, Phase 3 Trial.

Background and Aims

Insulin degludec (IDeg) is a new basal insulin that forms soluble multi-hexamers upon s.c. injection, resulting in an ultra-long and consistent glucose-lowering effect. Insulin degludec/insulin as part (IDegAsp) is a soluble co-formulation of IDeg (70%) and insulin as part (30%) that provides both mealtime and basal insulin coverage. We investigated the efficacy and safety of IDegAsp in insulin-nave adults with type 2 diabetes inadequately controlled on oral antidiabetic drugs (OADs) in a phase 3, 26-week, open-label, treat-to-target trial.

Materials and Methods

Participants (mean: 60.5 years old; $HbA_{1c}$ 8.4%; fasting plasma glucose [FPG] 9.0 mmol/L; BMI 25.1 kg/m$^2$; duration of diabetes 11.7 years) were randomised to once-daily injections of IDegAsp (n=147) or insulin glargine (IGlar; n=149), both with/without up to 2 OADs (excluding sulphonylureas, dipeptidyl peptidase-4 inhibitors and glinides).

IDegAsp was injected before the largest meal of the day at the discretion of each participant (and maintained throughout the trial); IGlar was injected at the same time each day according to label. Both insulins were titrated to an FPG<5 mmol/L.

Results

After 26 weeks, mean $HbA_{1c}$ was 7.0% with IDegAsp and 7.3% with IGlar.

Analysis of change in $HbA_{1c}$ from baseline to end-of-trial demonstrated that IDegAsp was superior to IGlar (estimated treatment difference (ETD) IDegAsp-IGlar: −0.28%-points [−0.46; −0.10]$_{95\% \ CI}$, p<0.001). At end-of-trial, a greater proportion of subjects achieved $HbA_{1c}$<7.0% with IDegAsp (58.5%) vs. IGlar (40.3%). Mean FPG was similar for IDegAsp and IGlar (5.7 vs. 5.6 mmol/L; ETD IDegAsp-IGlar: 0.15 mmol/L [−0.29; 0.60], p=NS).

No severe hypoglycaemia was reported.

Confirmed hypoglycaemia (PG<3.1 mmol/L) was reported for 44% of subjects in both groups; IDegAsp was associated with a numerically lower (27%) rate of confirmed hypoglycaemia than IGlar (estimated rate ratio (ERR) IDegAsp/IGlar: 0.73 [0.50; 1.08] p=NS).

A significantly greater proportion of subjects achieved $HbA_{1c}$<7.0% at end-of-trial (without confirmed hypoglycaemia in the last 12 weeks of treatment) with IDegAsp compared to IGlar (43% vs. 25%; Odds Ratio 2.21 [1.25; 3.92], p=0.003).

The rate of nocturnal confirmed hypoglycaemia (confirmed hypoglycaemia with onset between 00:01-05:59 h) was numerically lower (by 25%) with IDegAsp than IGlar (RR: 0.75 [0.34; 1.64], p=NS).

Mean daily insulin doses were similar between groups at the end-of-trial (IDegAsp: 28 U; IGlar: 29 U) as were increases in body weight from baseline (0.7 kg for both groups). Overall rates of adverse events were similar between groups with no treatment-specific pattern or clustering.

Conclusion

IDegAsp dosed once daily with the largest meal of the day provided superior long-term glycaemic control with similar FPG to IGlar at a numerically lower rate of overall and nocturnal hypoglycaemia.

Thus, superior glycaemic control was achieved with a once-daily administration of IDegAsp vs. IGlar in subjects with Type 2 Diabetes that are inadequately controlled with oral drugs.

Discussion and Overall Conclusions

Background Information

Insulin analogues have been developed that more closely mimic endogenous insulin secretion as compared with human insulin preparations and are now an established part of diabetes management. IDegAsp is the first soluble ready-to-use insulin that comprises both a basal insulin component (IDeg) and a bolus insulin component (IAsp). In the present trial, insulin-nave subjects with type 2 diabetes mellitus inadequately controlled with OADs alone, were chosen to investigate the use of IDegAsp for initiation of insulin treatment as IDegAsp offers ultra-long-acting basal coverage with additional prandial coverage of one meal.

The trial was conducted to confirm the efficacy and safety of treatment with IDegAsp OD as monotherapy or in combination with up to 2 OADs, when glucose levels are no longer controlled by OADs alone in subjects with type 2 diabetes mellitus. The primary objective was to confirm the efficacy of IDegAsp OD±OADs in controlling glycaemic with respect to change from baseline in $HbA_{1c}$ after 26 weeks of treatment. Baseline characteristics were similar in the two treatment arms and approximately 93% of subjects completed the trial.

As in any open-label trial, there may be a risk of an underlying reporting bias. In general, investigators are likely to be more alert when treating subjects with a new medical entity such as IDegAsp and subjects may also be more hesitant towards a new treatment. This could influence the reporting of AEs and hypoglycaemia.

Glycaemic Control

IDegAsp was superior to IGlar in terms of lowering $HbA_{1c}$ with a clinically relevant difference of 0.28%-points after 26 weeks of treatment. After 26 weeks of treatment, the observed mean $HbA_{1c}$ was reduced to 7.0% in IDegAsp as compared to 7.3% in the IGlar group. The estimated reduction in $HbA_{1c}$ was −1.61%-points with IDegAsp and −1.33%-points with IGlar. The estimated odds of achieving the ADA target of $HbA_{1c}$<7% with or without confirmed hypoglycaemia was approximately two times higher with IDegAsp compared to IGlar, highlighting the fact that the treatment with the combination of an ultra-long-acting basal insulin with additional prandial coverage at the main meal provides superior glucose control without compromising safety. In addition, the estimated odds of achieving the IDF target of $HbA_{1c}$<6.5% was also approximately two times higher with IDegAsp compared to IGlar.

The FPG reduction was similar in both the treatment groups after 26 weeks of treatment but was achieved with a lower risk of both nocturnal and overall confirmed hypoglycaemic episodes in the subjects receiving IDegAsp.

Both IDegAsp and IGlar treatments resulted in overall reductions in the SMPG profiles and treatment with IDegAsp resulted in a lower prandial increment at the main evening meal and across all meals compared with IGlar. The superior glucose lowering effect of IDegAsp seen after the main evening meal reflects the benefit of the prandial coverage of IDegAsp. There were not more hypoglycaemic events in the IDegAsp group compared to the IGlar group after the main evening meal. This supports the advantage of letting the patients choose the time of dosing depending on when they have their largest meal. That IDegAsp is superior in controlling postprandial glucose excursions compared with IGlar without compromising the FPG control, suggests that the insulin degludec to insulin as part ratio of IDegAsp is appropriate for this group of subjects.

Insulin Doses and Titration

Initiation of IDegAsp at 10 U OD appeared safe with only few hypoglycaemic episodes reported during the first 4 weeks of insulin administration.

The mean daily insulin doses followed the same pattern in the IDegAsp and IGlar groups throughout the trial. After 26 weeks of treatment, the mean insulin doses were 28 U (0.41 U/kg) and 29 U (0.41 U/kg) in the IDegAsp and IGlar groups, respectively.

All subjects in both treatment groups were titrated based on prebreakfast SMPG regardless of injection time. Subject compliance and a close adherence to the titration algorithm were indicated in both treatment groups as the mean differences between the prescribed dose and the actual dose and between the titration algorithm dose and the prescribed dose, respectively, were close to 0 U (mean difference [prescribed dose—titration algorithm dose] was between −2 U and −1 U) throughout the trial.

The prandial component of IDegAsp resulted in lower post evening meal and bedtime glucose values, thus reducing the need for basal insulin coverage during the night, so the basal component of IDegAsp (70% insulin degludec) is adequate to achieve the same average FPG values as with IGlar.

Hypoglycaemia

The observed rate of confirmed hypoglycaemic episodes was numerically lower with IDegAsp compared to IGlar.

One of the greatest concerns for subjects with diabetes mellitus is the risk of hypoglycaemic episodes occurring during sleep.[33,34] Treatment with IDegAsp resulted in a numerically lower rate of nocturnal confirmed hypoglycaemic episodes compared to IGlar while maintaining a superior glucose lowering effect after 26 weeks of treatment. The more stable and flat action profile of the basal component of IDegAsp makes it possible for the subjects to reach the glycaemic target without compromising safety. No episodes of severe or nocturnal severe hypoglycaemia were reported during this trial in either treatment group.

There was no clustering of hypoglycaemic episodes observed at any time point during the trial.

Safety and Tolerability

Overall, treatment with IDegAsp was well tolerated in this study and the AE profile of IDegAsp was in accordance with the safety profile seen in the complete IDegAsp development programme where no unexpected safety signals were identified. IDegAsp remains a safe, well-tolerated and efficacious treatment.

Overall Conclusions

The results of this confirmatory, randomised, controlled, 26-week trial demonstrate the efficacy and safety of IDegAsp versus IGlar, both administered once daily±oral antidiabetic drugs in insulin-naïve subjects with type 2 diabetes mellitus. IDegAsp effectively improves glycaemic control as measured by HbA1c and the data confirm superiority to IGlar with respect to lowering HbA1c and lowering prandial plasma glucose increment at dinner. IDegAsp is superior to IGlar in getting a larger proportion of subjects to $HbA_{1c}$ target <7% without confirmed hypoglycaemia. IDegAsp and IGlar result in a similar reduction in FPG. IDegAsp is associated with a numerically lower rate of confirmed hypoglycaemia and nocturnal confirmed hypoglycaemia than IGlar. Body weight increases slightly in both treatment groups. In this trial, no safety issues are identified with IDegAsp.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A method for treating diabetes mellitus comprising:
    administering to a subject in need thereof, during or around the time of the largest meal of the day for said subject, a pharmaceutically acceptable combination comprising LysB29(Nε-hexadecandioyl-γ-Glu) des (B30) human insulin and $Asp^{B28}$ human insulin;
    wherein the ratio of the combination administered is selected from about 90/10%, about 85/15%, about 80/20%, about 70/30%, about 60/40%, about 50/50%, about 40/60%, about 30/70%, or about 10/90%;
    wherein said combination is administered in an amount to achieve a beneficial glycaemic control in said subject as determined by the levels of $HbA_{1c}$ in said subject;
    wherein said beneficial glycaemic control by said combination is superior to any glycaemic control achieved by an equivalent dose of insulin glargine (IGlar) in said subject as determined by the levels of $HbA_{1c}$ in said subject after administration of IGlar to said subject;
    wherein said beneficial glycaemic control by said combination comprises decreasing the levels of $HbA_{1c}$ in said subject to about 7 or less; and
    wherein said decrease in levels of $HbA1_c$ is achieved in about 26 weeks or less.

2. A method according to claim 1 wherein the combination is a fixed-dose or single formulation.

3. A method according to claim 1 wherein the combination comprises separate formulations concomitantly or sequentially administered.

4. A method according to claim 2 wherein the ratio of LysB29(Nε-hexadecandioyl-γ-Glu) des(B30) human insulin to $Asp^{B28}$ human insulin is about 70/30%.

5. A method according to claim 3 wherein the ratio of LysB29(Nε-hexadecandioyl-γ-Glu) des(B30) human insulin to $Asp^{B28}$ human insulin is about 70/30%.

* * * * *